United States Patent
Lang et al.

(10) Patent No.: US 9,289,153 B2
(45) Date of Patent: *Mar. 22, 2016

(54) JOINT AND CARTILAGE DIAGNOSIS, ASSESSMENT AND MODELING

(75) Inventors: Philipp Lang, Lexington, MA (US); Daniel Steines, Lexington, MA (US); Eugene J. Alexander, San Clemente, CA (US); Thomas P. Andriacchi, Los Altos Hills, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 517 days.

This patent is subject to a terminal disclaimer.

(21) Appl. No.: 11/410,515

(22) Filed: Apr. 25, 2006

(65) Prior Publication Data

US 2007/0015995 A1    Jan. 18, 2007

Related U.S. Application Data

(63) Continuation-in-part of application No. 09/953,373, filed on Sep. 14, 2001, now Pat. No. 7,184,814, and a continuation-in-part of application No. 09/882,363, filed on Jun. 15, 2001, application No. 11/415,515, (Continued)

(51) Int. Cl.
| | |
|---|---|
| A61B 5/05 | (2006.01) |
| A61B 5/055 | (2006.01) |
| A61B 5/103 | (2006.01) |
| A61B 5/00 | (2006.01) |
| G01R 33/50 | (2006.01) |

(Continued)

(52) U.S. Cl.
CPC .............. *A61B 5/055* (2013.01); *A61B 5/1038* (2013.01); *A61B 5/4514* (2013.01); *A61B 5/4528* (2013.01); *G01R 33/50* (2013.01); *G01R 33/56* (2013.01); *G06T 7/0012* (2013.01); *G06T 7/0081* (2013.01); *A61B 5/1075* (2013.01); *A61B 5/7257* (2013.01); *G01R 33/5608* (2013.01); *G06T 2207/10088* (2013.01); *G06T 2207/20141* (2013.01); *G06T 2207/30008* (2013.01)

(58) Field of Classification Search
USPC .................... 600/407, 437, 410, 413, 416
See application file for complete search history.

(56) References Cited

U.S. PATENT DOCUMENTS

| | | | |
|---|---|---|---|
| 4,936,862 A | 6/1990 | Walker et al. | |
| 5,303,148 A * | 4/1994 | Mattson et al. | ............... 600/437 |

(Continued)

OTHER PUBLICATIONS

"Computer-aided Planning of Patellofemoral Joint OA Surgery: Developing Physical models from Patient MRI" Miccai, Oct. 11-13, 1998; Cohen et al.*

Reddy et al., "Triple Quantum Sodium Imaging of Articular Cartilage," Magnetic Resonance in Imaging, vol. 38, pp. 279-284 (Feb. 1997).

*Primary Examiner* — Joel F Brutus
(74) *Attorney, Agent, or Firm* — Sunstein Kann Murphy & Timbers LLP

(57) ABSTRACT

Methods are disclosed for assessing the condition of a cartilage in a joint and assessing cartilage loss, particularly in a human knee. The methods include converting an image such as an MRI to a three dimensional map of the cartilage. The cartilage map can be correlated to a movement pattern of the joint to assess the affect of movement on cartilage wear. Changes in the thickness of cartilage over time can be determined so that therapies can be provided. The amount of cartilage tissue that has been lost, for example as a result of arthritis, can be estimated.

13 Claims, 21 Drawing Sheets

Related U.S. Application Data which is a continuation-in-part of application No. 10/764,010, filed on Jan. 22, 2004, which is a continuation of application No. 09/662,224, filed on Sep. 14, 2000, now Pat. No. 7,239,908, said application No. 09/882,363 is a continuation of application No. PCT/US99/30265, filed on Dec. 16, 1999, said application No. 09/662,224 is a continuation-in-part of application No. PCT/US99/30265.

(60) Provisional application No. 60/232,637, filed on Sep. 14, 2000, provisional application No. 60/232,639, filed on Sep. 14, 2000, provisional application No. 60/112,989, filed on Dec. 16, 1998.

(51) Int. Cl.
*G01R 33/56* (2006.01)
*G06T 7/00* (2006.01)
*A61B 5/107* (2006.01)

(56) References Cited

U.S. PATENT DOCUMENTS

| | | | |
|---|---|---|---|
| 5,360,446 A * | 11/1994 | Kennedy | 128/898 |
| 5,554,190 A * | 9/1996 | Draenert | 128/898 |
| 5,571,205 A * | 11/1996 | James | 623/24 |
| 5,682,886 A * | 11/1997 | Delp et al. | 600/407 |
| 6,001,895 A * | 12/1999 | Harvey et al. | 523/113 |
| 6,126,690 A * | 10/2000 | Ateshian et al. | 623/22.4 |
| 6,132,468 A * | 10/2000 | Mansmann | 623/20.16 |
| 6,816,607 B2 | 11/2004 | O'Donnell et al. | |
| 7,796,791 B2 | 9/2010 | Tsougarakis et al. | |
| 7,799,077 B2 | 9/2010 | Lang et al. | |
| 2002/0027970 A1* | 3/2002 | Chapman et al. | 378/62 |
| 2003/0236473 A1 | 12/2003 | Dore et al. | |
| 2006/0052795 A1 | 3/2006 | White | |
| 2006/0069318 A1 | 3/2006 | Keaveny et al. | |
| 2007/0118243 A1 | 5/2007 | Schroeder et al. | |
| 2008/0058945 A1 | 3/2008 | Hajaj et al. | |

* cited by examiner

 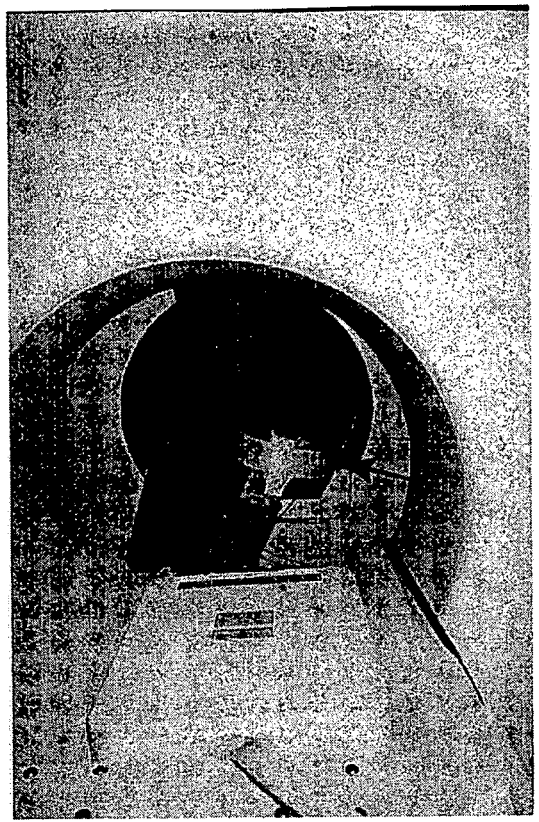
FIG. 9A  FIG. 9B
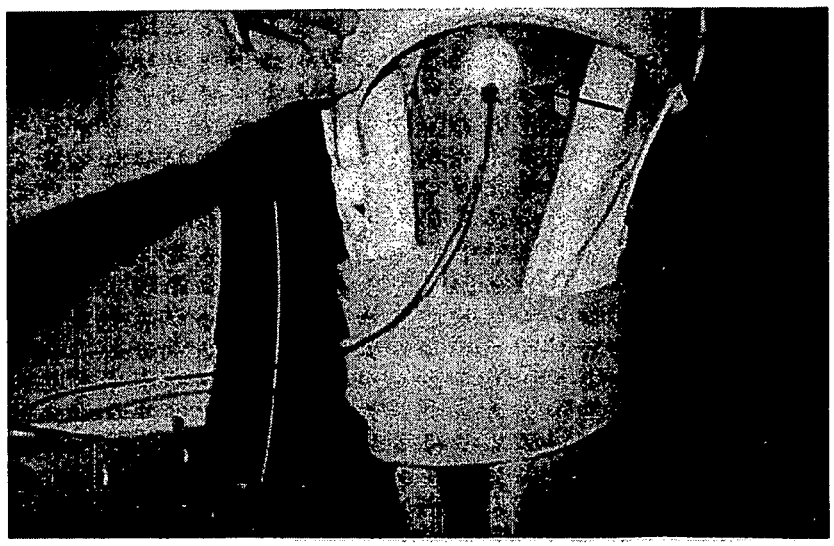
FIG. 9C

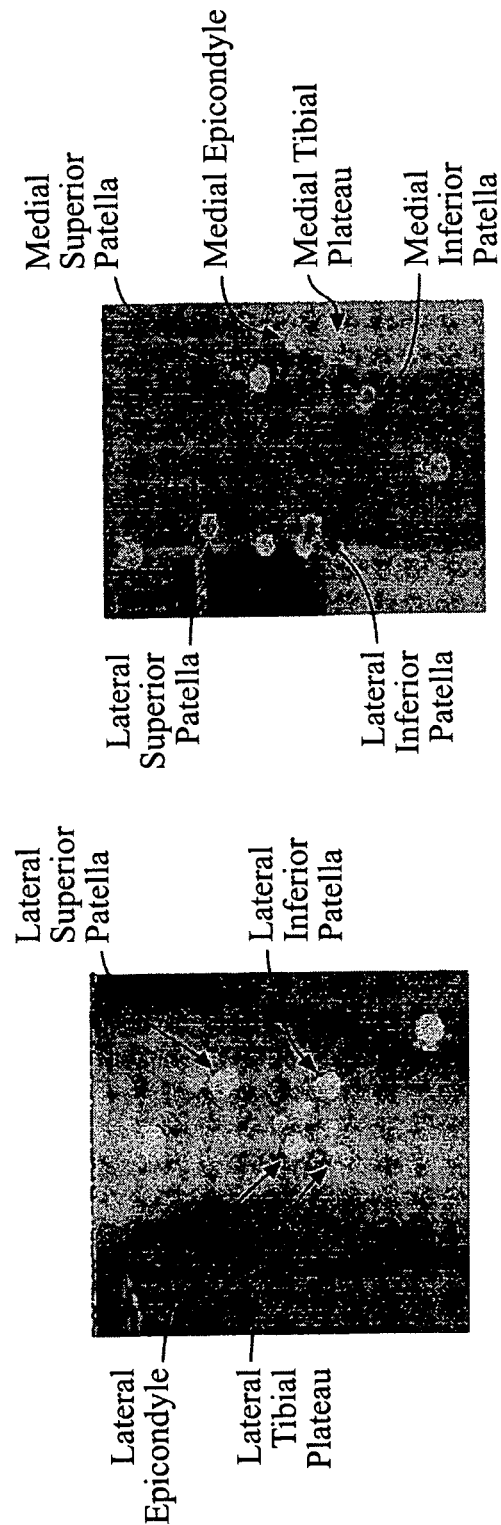

JOINT AND CARTILAGE DIAGNOSIS, ASSESSMENT AND MODELING

CROSS REFERENCE TO RELATED APPLICATIONS

This application is a continuation in part of U.S. patent application Ser. No. 09/953,373, entitled "Assessing the Condition of a Joint and Assessing Cartilage Loss," filed Sep. 14, 2001, which in turn claims the benefit of U.S. Patent Application No. 60/232,637 and 60/232,639, both filed on Sep. 14, 2000. Each of the above-described patent applications is hereby incorporated by reference, in its entirety. U.S. patent application Ser. No. 09/953,373 is also a continuation in part of U.S. patent application Ser. No. 09/882,363, entitled "Assessing the Condition of a Joint and Preventing Damage," filed Jun. 15, 2001. This application is also a continuation in part of U.S. patent application Ser. No. 10/764,010, entitled "Assessing the Condition of a Joint and Devising Treatment," filed Jan. 22, 2004, which in turn is a continuation of U.S. patent application Ser. No. 09/662,224, entitled "Assessing the Condition of a Joint and Devising Treatment," filed Sep. 14, 2000. U.S. patent application Ser. No. 09/882,363 is a continuation of and U.S. patent application Ser. No. 09/662,224 is a continuation-in-part of PCT/US99/30265, entitled "Assessing the Condition of a Joint and Preventing Damage," filed Dec. 16, 1999, which in turn claims the benefit of U.S. Provisional Application Ser. No. 60/112,989, filed Dec. 16, 1998.

This invention was supported in part by a National Institute of Health Grant No. PAR-97-014, and the government may have rights in this invention.

TECHNICAL FIELD

This invention relates to assessing the condition of a joint and the use of the assessment in aiding in prevention of damage to the joint or treatment of diseased cartilage in the joint.

BACKGROUND ART

Osteoarthritis is the most common condition to affect human joints as well as a frequent cause of locomotor pain and disability. More particularly, osteoarthritis (OA) of the knee occurs in a substantial portion of the population over the age of fifty.

In spite of its societal impact and prevalence, however, there is a paucity of information on the factors that cause osteoarthritis to progress more rapidly in some individuals and not in others. Previously considered a "wear and tear" degenerative disease with little opportunity for therapeutic intervention, osteoarthritis is now increasingly viewed as a dynamic process with potential for new pharmacologic and surgical treatment modalites such as cartilage transplantation, osteochondral allo- or autografting, osteotomies and tibial corticotomies with angular distraction.

However, the appropriate deployment and selection of treatment interventions for OA is dependent on the development of better methods for the assessment of the condition of a patient's joint and the degeneration process.

There is, therefore, a need for improved methods for examining the factors that influence as well as quantification of the progression of the disease.

Magnetic resonance imaging (MRI) is an accurate non-invasive imaging technique for visualization of articular cartilage in osteoarthritis, particularly in knees. However, current MRI techniques cannot provide information on the relationship between the location of the cartilage loss and variations in the load bearing areas during the walking cycle. This information is important since it has been shown that dynamic loads during walking are related to the progression of knee OA. Thus, the ability to locate cartilage defects or areas of cartilage thinning relative to the load bearing areas of the knee could be valuable in evaluating factors influencing the progression of osteoarthritis.

REFERENCES

1. Alexander E J: Estimating the motion of bones from markers on the skin [Doctoral Dissertation]. University of Illinois at Chicago; 1998.
2. Alexander E J, Andriacchi T P: Correcting for deformation in skin-based marker systems. Proceedings of the 3rd Annual Gait and Clinical Movement Analysis Meeting, San Diego, Calif., 1998.
3. Alexander E J, Andriacchi T P: Internal to external correspondence in the analysis of lower limb bone motion. Proceedings of the 1999 ASME Summer Bioengineering Conference, Big Sky, Mont., 1999.
4. Alexander E J, Andriacchi T P: State estimation theory in human movement analysis. Proceedings of the 1998 ASME International Mechanical Engineering Congress, 1998.
5. Alexander E J, Andriacchi T P, Lang P K: Dynamic functional imaging of the musculoskeletal system. ASME Winter International Congress and Exposition, Nashville, Tenn., 1999.
6. Alexander E J, Andriacchi T P, Naylor D L: Optimization techniques for skin deformation correction. International Symposium on 3-D Human Movement Conference, Chattanooga, Tenn., 1998.
7. Allen P R, Denham R A, Swan A V: Late degenerative changes after meniscectomy: factors affecting the knee after operations. J Bone Joint Surg 1984; 66B: 666-671.
8. Alley M T, Shifrin R Y, Pelc N J, Herfkens R J: Ultrafast contrast-enhanced three dimensional MR angiography: state of the art. Radiographics 1998; 18: 273-285.
9. Andriacchi T P: Dynamics of knee malalignment. Orthop Clin North Am 1994; 25: 395-403.
10. Andriacchi T P, Alexander E J, Toney M K, Dyrby C O, Sum J: A point cluster method for in vivo motion analysis: applied to a study of knee kinematics. J Biomech Eng 1998; 120(12): 743-749.
11. Andriacchi T P, Lang P, Alexander E, Hurwitz D: Methods for evaluating the progression of osteoarthritis. J Rehab Res Develop 2000; 37, 2: 163-170.
12. Andriacchi T P, Sen K, Toney M K, Yoder D: New developments in musculoskeletal testing. Proceedings of the Canadian Society of Biomechanics, 1994.
13. Andriacchi T P, Strickland A B: Gait analysis as a tool to assess joint kinetics biomechanics of normal and pathological human articulating joints. Nijhoff, Series E 1985; 93: 83-102.
14. Andriacchi T P, Toney M K: In vivo measurement of six-degrees-of-freedom knee movement during functional testing. Transactions of the Orthopedic Research Society 1995: 698.
15. Beaulieu C F, Hodge D K, Bergman A G: Glenohumeral relationships during physiological shoulder motion and stress testing: initial experience with open MRI and active scan-plane registration. Radiology 1999: accepted for publication.

16. Beaulieu C F, Hodge D K, Thabit G, Lang P K, Bergman A G: Dynamic imaging of glenohumeral instability with open MRI. Int. Society for Magnetic Resonance in Medicine, Sydney, Australia, 1998.
17. Benedetti M G, Cappozzo A: Anatomical landmark definition and identification in computer aided movement analysis in a rehabilitation context II (Internal Report). U Degli Studi La Sapienza 1994: 1-31.
18. Bergman A G, Beaulieu C F, Pearle A D, et al.: Joint motion: assessment by upright interactive dynamic near-real time MR imaging. Radiological Society of North America, 83rd Scientific Assembly and Annual Meeting, Chicago, Ill., 1997.
19. Biswal S, Hastie T, Andriacchi T, Bergman G, Dillingham M F, Lang P: The rate of progressive cartilage loss at the knee is dependent on the location of the lesion: a longitudinal MRI study in 43 patients. Arthritis & Rheumatism 2000: submitted for publication.
20. Bobic V: Arthoscopic osteochondral autograft transplantation in anterior cruciate ligament reconstruction: a preliminary clinical study. Knee Surg Sports Traumatol Arthrosc 1996; 3 (4): 262-264.
21. Boe S, Hansen H: Arthroscopic partial meniscectomy in patients aged over 50. J Bone Joint Surg 1986; 68B: 707.
22. Bregler. C, Hertzmann A, Biermann H: Recovering non-rigid 3D shape from image streams. Proc. IEEE Conference on Computer Vision and Pattern Recognition 2000: in press.
23. Brittberg M, Lindahl A, Homminga G, Nilsson A, Isaksson O, Peterson L: A critical analysis of cartilage repair. Acta Orthop Scand 1997; 68 (2) 186-191.
24. Brittberg M, Lindahl A, Nilsson A, Ohlsson C, Isaksson O, Peterson L: Treatment of deep cartilage defects in the knee with autologous chondrocyte transplantation. N Engl J Med 1994; 331 (14): 889-895.
25. Broderick L S, Turner D A, Renfrew D L, Schnitzer T J, Huff J P, Harris C: Severity of articular cartilage abnormality in patients with osteoarthritis: evaluation with fast spin-echo MR vs arthroscopy. AJR 1994; 162: 99-103.
26. Butts K, Pauly J M, Kerr A B, Bergman A G, Beaulieu C F: Real-Time MR imaging of joint motion on an open MR imaging scanner. Radiological Society of North America, 83rd Scientific Assembly and Annual Meeting, Chicago, Ill., 1997.
27. Cohen Z A, McCarthy D M, Kwak, S D, Legrand P, Fogarasi F, Ciaccio E J, Ateshian G A: Knee cartilage topography, thickness, and contact areas from MRI: in-vitro calibration and in-vivo measurements. Osteoarthritis and Cartilage 1999; 7: 95-109.
28. Daniel B, Butts K, Glover G, Herfkens R: Breast cancer: gadolinium-enhanced MR imaging with a 0.5 T open imager and three-point Dixon technique. Radiology 1998; 207 (1): 183-190.
29. Disler D G: Fat-suppressed three-dimensional spoiled gradient-recalled MR imaging: assessment of articular and physeal hyaline cartilage. AJR 1997; 169: 1117-1123.
30. Disler D G, McCauley T R, Kelman C G, et al.: Fat-suppressed three-dimensional spoiled gradient-echo MR imaging of hyaline cartilage defects in the knee: comparison with standard MR imaging and arthroscopy. AJR 1996; 167: 127-132.
31. Disler D G, McCauley T R, Wirth C R, Fuchs M D: Detection of knee hyaline cartilage defects using fat-suppressed three-dimensnional spoiled gradient-echo MR imaging: comparison with standard MR imaging and correlation with arthrosocpy. AJR 1995; 165: 377-382.
32. Doherty M, Hutton C, Bayliss M T: Osteoarthritis. In: Maddison P J, Isenberg D A, Woo P, et al., eds. Oxford Textbook of Rheumatology, vol 1. Oxford, N.Y., Tokyo: Oxford University Press, 1993; 959-983.
33. Dougados M, Gueguen A, Nguyen M, et al.: Longitudinal radiologic evaluation of osteoarthritis of the knee. J Rheumatol 1992; 19: 378-384.
34. Du Y P, Parker D L, Davis W L: Vessel enhancement filtering in three-dimensional MR angiography. J Magn Res Imaging 1995; 5: 151-157.
35. Du Y P, Parker D L, Davis W L, Cao G: Reduction of partial-volume artifacts with zero-filled interpolation in three-dimensional MR angiography. J Magn Res Imaging 1994; 4: 733-741.
36. Dumoulin C L, Souza S P, Darrow R D: Real-time position monitoring of invasive devices using magnetic resonance. Magn Reson Med 1993; 29: 411-5.
37. Dyrby C O: The three-dimensional kinematics of knee joint motion: functional differences in two populations [Master's Thesis]. University of Illinois at Chicago; 1998.
38. Eckstein F, Westhoff J, Sittek H, et al.: In vivo reproducibility of three-dimensional cartilage volume and thickness measurements with MR imaging. AJR 1998; 170(3): 593-597.
39. Elting J J, Hubbell J C: Unilateral frame distraction: proximal tibial valgus osteotomy for medial gonarthritis. Contemp Orthop 1993; 27(6): 522-524.
40. Falcao A X, Udupa J K, Samarasekera S, Sharma S: User-steered image segmentation paradigms: Live wire and live lane. Graphical Models and Image Processing 1998; 60: 233-260.
41. Felson D T, Zhang Y, Anthony J M, Naimark A, Anderson J J: Weight loss reduces the risk for symptomatic knee osteoarthritis in women: the Framingham study. Ann Intern Med 1992; 116: 535-539.
42. Garrett J C: Osteochondral allografts for reconstruction of articular defects of the knee. Instr Course Lect 1998; 47: 517-522.
43. Ghosh S, Newitt D C, Majumdar S: Watershed segmentation of high resolution articular cartilage image. International Society for Magnetic Resonance in Medicine, Philadelphia, 1999.
44. Gouraud H: Continuous shading of curved surfaces. IEEE Trans on Computers 1971; C-20(6).
45. Gray A: Modern Differential Geometry of Curves and Surfaces. 1993: CRC Press, Inc.
46. Hargreaves B A, Gold G E, Conolly S M, Nishimura D G: Technical considerations for DEFT imaging. International Society for Magnetic Resonance in Medicine, Sydney, Australia, Apr. 17-24, 1998.
47. Hargreaves B A, Gold G E, Lang P K, Bergman G, Conolly S M, Nishimura D G: Imaging of articular cartilage using driven equilibrium. International Society for Magnetic Resonane in Medicine, Sydney, Australia, Apr. 17-24, 1998.
48. Hayes C, Conway W: Evaluation of articular cartilage: radiographic and cross-sectional imaging techniques. Radiographics 1992; 12: 409428.
49. Henkelman R M, Stanisz G, Kim J, Bronskill M: Anisotropy of NMR properties of tissues. Magn Res Med 1994; 32: 592-601.
50. Hoppenfeld S, Huton R: Physical Examination of the Knee. In: Hoppenfeld S, ed. Physical Examination of the Spine and Extremities: Appleton-Century-Crofts/Prentice-Hall, 1976; 171-196.

51. Hyhlik-Durr A, Faber S, Burgkart R, et al.: Precision of tibial cartilage morphometry with a coronal water-excitation MR sequence. European Radiology 2000; 10 (2): 297-303.
52. Irarrazabal P, Nishimura D G: Fast three-dimensional magnetic resonance imaging. Mag Res Med 1995; 33: 656-662.
53. Johnson F, Leitl S, Waugh W: The distribution of load across the knee. A comparison of static and dynamic measurements. J Bone Joint Surg 1980; 62B: 346-349.
54. Johnson T S: In vivo contact kinematics of the knee joint: Advancing the point cluster technique. Ph.D. thesis, University of Minnesota 1999.
55. Johnson T S, Andriacchi T P, Laurent M: Development of a knee wear method based on prosthetic in vivo slip velocity. Transactions of the Orthopedic Research Society, 46th Annual Meeting, March, 2000.
56. LaFortune M A, Cavanagh P R, Sommer H J, Kalenak A: Three dimensional kinematics of the human knee during walking. J. Biomechanics 1992; 25: 347-357.
57. Lang P, Alexander E, Andriacchi T: Funcional joint imaging: a new technique integrating MRI and biomotion studies. International Society for Magnetic Resonance in Medicine, Denver, Apr. 18, 2000-Apr. 24, 2000, 2000.
58. Lang P, Biswal S, Dillingham M, Bergman G, Hastie T, Andriacchi T: Risk factors for progression of cartilage loss: a longitudinal MRI study. European Society of Musculoskeletal Radiology, 6th Annual Meeting, Edinburgh, Scotland, 1999.
59. Lang P, Hargreaves B A, Gold G, et al.: Cartilage imaging: comparison of driven equilibrium with gradient-echo, SPGR, and fast spin-echo sequences. International Society for Magnetic Resonance in Medicine, Sydney, Australia, Apr. 17-24, 1998.
60. Ledingham J, Regan M, Jones A, Doherty. M: Factors affecting radiographic progression of knee osteoarthritis. Ann Rheum Dis. 1995; 54: 53-58.
61. Lorensen W E, Cline H E: Marching cubes: a high resolution 3d surface construction algorithm. Comput Graph 1987; 21: 163-169.
62. Losch A, Eckstein F, Haubner M, Englmeier K H: A non-invasive technique for 3-dimensional assessment of articular cartilage thickness based on MRI part 1: development of a computational method. Magn Res Imaging 1997; 15, 7: 795-804.
63. Lu T W, O'Connor J J: Bone position estimation from skin marker co-ordinates using globals optimisation with joint constraints. J Biomechanics 1999; 32: 129-134.
64. Lucchetti L, Cappozzo A, Cappello A, Della Croce U: Skin movement artefact assessment and compensation in the estimation of knee-joint kinematics. J Biomechanics 1998; 31: 977-984.
65. Lynch J A, Zaim S, Zhao J, Stork A, Genant H K: Cartilage segmentation of 3D MRI scans of the osteoarritic knee combining user knowledge and active contours. Proc. SPIE 3979 Medical Imaging, San Diego, February 2000.
66. Maki J H, Johnson G A, Cofer G P, MacFall J R: SNR improvement in NMR microscopy using DEFT. J Mag Res 1988.
67. Meyer C H, Pauly J M, Macovski A, Nishimura D G: Simultaneous spatial and spectral selective excitation. Magn Res Med 1990; 15: 287-304.
68. Mollica Q, Leonardi W, Longo G, Travaglianti G: Surgical treatment of arthritic varus knee by tibial corticotomy and angular distraction with an external fixator. Ital J Orthop Traumatol 1992; 18 (1): 17-23.
69. Nizard R S: Role of tibial osteotomy in the treatment of medial femorotibial osteoarthritis. Rev Rhum Engl Ed 1998; 65 (7-9): 443-446.
70. Noll D C, Nishimura D, Macovski A: Homodyne detection in magnetic resonance imaging. IEEE Trans Med Imag 10 1991; 10 (2): 154-163.
71. Ogilvie-Harris D J, Fitsialos D P: Arthroscopic management of the degenerative knee. Arthroscopy 1991; 7: 151-157.
72. Pearle A, Bergman A G, Daniels B, et al.: Use of an external MR-tracking coil for active scan plane registration during dynamic musculoskeletal MR imaging in a vertically open MRT unit. American Roentgen Ray Society, San Francisco, Calif., 1998.
73. Pearle A D, Daniel B L, Bergman A G: Joint motion in an open MR unit using MR tracking. JMRI 1999; 10 (10): 1566-1576.
74. Peterfy C, van Dijke C, Lu Y, et al.: Quantification of the volume of articular cartilage in the metacarpophalangeal joints of the hand: accuracy and precision of three-dimensional MR imaging. AJR 1995; 165: 371-375.
75. Peterfy C G, Majumdar S, Lang P, van Dijke C, Sack K, Genant H K: MR imaging of the arthritic knee: improved discrimination of cartilage, synovium, and effusion with pulsed saturation transfer and fat-suppressed T1-weighted sequences. Radiology 1994; 191(2): 413-419.
76. Peterfy C G, van Dijke C F, Janzen D L, et al.: Quantification of articular cartilage in the knee with pulsed saturation transfer subtraction and fat-suppressed MR imaging: optimization and validation. Radiology 1994; 192(2): 485-491.
77. Piplani M A, Disler D G, McCauley T R, Holmes T J, Cousins J P: Articular cartilage volume in the knee: semi-automated determination from three-dimensional reformations of MR images. Radiology 1996; 198: 855-859.
78. Potter H G, Linklater J M, Allen A A, Hannafm J A, Haas S B: Magnetic resonance imaging of articular cartilage in the knee: an evaluation with use of fast-spin-echo imaging. J Bone Joint Surg 1998; 80-A(9): 1276-1284.
79. Prodromos C C, Andriacchi T P, Galante J O: A relationship between gait and clinical changes following high tibial osteotomy. J Bone Joint Surg 1985; 67A: 1188-1194.
80. Radin E L, Burr D B, Caterson B, Fyhrie D, Brown T D, Boyd R D: Mechanical determinants of osteoarthrosis. Sem Arthr Rheum 1991; 21(3): 12-21.
81. Radin E L, Burr D B, Fyhrie D: Characteristics of joint loading as it applies to osteoarthrosis. In: Mow V C, Woo S-Y, Ratcliffe T, eds. Symposium on Biomechanics of Diarthrodial Joints, vol 2. New York, N.Y.: Springer-Verlag, 1990; 437-451.
82. Recht M P, Piraino D W, Paletta G A, Schils J P, Belhobek G H: Accuracy of fat-suppressed three-dimensional spoiled gradient-echo FLASH MR imaging in the detection of patellofemoral articular cartilage abnormalities. Radiology 1996; 198: 209-212.
83. Recht M P, Resnick D: MR imaging of articular cartilage: current status and future directions. AJR 1994; 163: 283-290.
84. Ritter M A, Faris P M, Keating E M, Meding J B: Postoperative alignment of total knee replacement. Clin Orthop 1994; 299: 153-156.
85. Saito T, Toriwaki J-I: New algorithms for Euclidean distance transformation of an n-dimensional digitized picture with applications. Pattern Recognition 1994; 27 (11): 1551-1565.

86. Schipplein O D, Andriacchi T P: Interaction between active and passive knee stabilizers during level walking. J Orthop Res 1991; 9: 113-119.
87. Schouten J S A G, van den Ouweland F A, Valkenburg H A: A 12 year follow up study in the general population on prognostic factors of cartilage loss in osteoarthritis of the knee. Ann Rheum Dis 1992; 51: 932-937.
88. Sharif M, George E, Shepstone L, et al.: Serum hyaluronic acid level as a predictor of disease progression in osteoarhritis of the knee. Arthritis Rheum 1995; 38: 760-767.
89. Sharma L, D. E. H, Thonar E J M A, et al.: Knee adduction moment, serum hyaluronic acid level, and disease severity in medial tibiofemoral osteoarthritis. Arthritis and Rheumatism 1998; 41(7): 1233-40.
90. Shoup R R, Becker E D: The driven equilibrium Fourier transform NMR technique: an experimental study. J Mag Res 1972; 8.
91. Slemenda C, Mazzuca S, Brandt K, Katz B: Lower extremity lean tissue mass and strength predict increases in pain and in functional impairment in knee osteoarthritis. Arthritis Rheum 1996; 39(suppl): S212.
92. Slemenda C, Mazzuca S, Brandt K, Katz B: Lower extremity strength, lean tissue mass and bone density in progression of knee osteoarthritis. Arthritis Rheum 1996; 39(suppl): S169.
93. Solloway S, Hutchinson C E, Waterton J C, Taylor C J: The use of active shape models for making thickness measurements of articular cartilage from MR images. Mag Res Med 1997; 37:943-952.
94. Spoor C W, Veldpas F E: Rigid body motion calculated from spatial coordinates of markers. J Biomechanics 1980; 13: 391-393.
95. Stamrnmberger T, Eckstein F, Englmeier K H, Reiser M: Determination of 3D cartilage thickness data from MR imaging: computational method and reproducibility in the living. Mag Res Med 1999; 41: 529-536.
96. Stammberger T, Eckstein F, Michaelis M, Englmeier K H, Reiser M: Interobserver reproducibility of quantitative cartilage measurements: Comparison of B-spline snakes and manual segmentation. Mag Res Imaging 1999; 17:1033-1042.
97. Steines D, Berger F, Cheng C, Napel S, Lang P: 3D thickness maps of articular cartilage for quantitative assessment of osteoarthritis. To be presented at ACR 64th Annual Scientific Meeting, Philadelphia, October 2000.
98. Steines D, Cheng C, Wong A, Berger F, Napel S, Lang P: Segmentation of osteoarthritic femoral cartilage from MR images. CARS—Computer-Assisted Radiology and Surgery, p. 578-583, San Francisco, 2000.
99. Steines D, Napel S, Lang P: Measuring volume of articular cartilage defects in osteoarthritis using MRI. To be presented at ACR 64th Annual Scientific Meeting, Philadelphia, October 2000.
100. Stevenson S, Dannucci G A, Sharkey N A, Pool R R: The fate of articular cartilage after transplantation of fresh and cryopreserved tissue-antigen-matched and mismatched osteochondral allografts in dogs. J Bone Joint Surg 1989; 71 (9): 1297-1307.
101. Tieschky M, Faber S, Haubner M, et al.: Repeatability of patellar. cartilage thickness patterns in the living, using a fat-suppressed magnetic resonance imaging sequence with short acquisition time and three-dimensional data processing. J Orthop Res 1997; 15(6): 808-813.
102. Tomasi C, Kanade T: Shape and motion from image streams under orthography—a factorization method. Proc Nat Acad Sci 1993; 90(21): 9795-9802.
103. Tsai J, Ashjaee S, Adalsteinsson E, et al.: Application of a flexible loop-gap resonator for MR imaging of articular cartilage at 3.0 T. International Society for Magnetic Resonance in Medicine, Denver, Apr. 18, 2000-Apr. 24, 2000, 2000.
104. Wang J W, Kuo K N, Andriacchi T P, Galante J O: The influence of walking mechanics and time on the results of proximal tibial osteotomy. J Bone Joint Surg 1990; 72A: 905-909.
105. Waterton J C, Solloway S, Foster J E, Keen M C, Gandy S, Middleton B J, Maciewicz R A, Watt I, Dieppe P A, Taylor C J: Diurnal variation in the femoral articular cartilage of the knee in young adult humans. Mag Res Med 2000, 43: 126-132.
106. Woolf S D, Chesnick F, Frank J, Lim K, Balaban R: Magnetization transfer contrast: MR imaging of the knee. Radiology 1991; 179: 623-628.
107. Worring M, Smeulders A W M: Digital curvature estimation. CVGIP: Image Understanding, 1993. 58(3): p. 366-382.
108. Yan C H: Measuring changes in local volumetric bone density: new approaches to quantitative computed tomography, Ph.D. thesis, 1998, Dept. of Electrical Engineering, Stanford University
109. Yao L, Gentili A, Thomas A: Incidental magnetization transfer contrast in fast spin-echo imaging of cartilage. J Magn Reson Imaging 1996; 6 (1): 180-184.
110. Yao L, Sinha S, Seeger L: MR imaging of joints: analytic optimization of GRE techniques at 1.5 T. AJR 1992; 158 (2): 339-345.
111. Yasuda K, T. M, Tsuchida T, Kameda K: A 10 to 15 year follow up observation of high tibial osteotomy in medial compartment osteoarthritis. Clin Orthop 1992; 282: 186-195.
112. Kass M, Witkin A, Terzopoulos D: Snakes: Active contour models. Int J Comput Vision 1988; 1:321-331
113. Falcao A X, Udupa J K, Samarasekera S, Sharma S, Hirsch B E, Lotufo R A: User-steered image segmentation paradigms: Live wire and live lane. GMIP 1998; 60, 233-260
114. Steines, D., et al., Segmentation of osteoarthritic femoral cartilage using live wire, ISMRM Eight Scientific Meeting, Denver Colo., 2000

SUMMARY OF THE INVENTION

This invention relates to assessing the condition of a joint of a mammal, particularly a human subject, using the assessment to treat and monitor the subject as needed for cartilage degeneration problems. While the numerous aspects of the invention are useful for joints generally, they are particularly suited for dealing with the human knee. Some aspects related the static images and degeneration patterns of a cartilage, while others relate to the interaction of such images and patterns to provide a better means of assessing the condition of a cartilage.

One aspect of this invention is a method for assessing the condition of a cartilage. The method comprises obtaining an image of a cartilage, (preferably a magnetic resonance image), converting the image to a three-dimensional degeneration pattern, and evaluating the degree of degeneration in a volume of interest of the cartilage. By performing this method at an initial time T, and a later time $T_2$, one can determine the change in the volume of interest and evaluate what steps to take for treatment.

Another aspect of this invention is a method of estimating the loss of cartilage in a joint. The method comprises obtaining a three-dimensional map of the cartilage at an initial time and calculating the thickness or regional volume of a region thought to contain degenerated cartilage so mapped at the initial time, obtaining a three-dimensional map of the cartilage at a later time, and calculating the thickness or regional volume of the region thought to contain degenerated cartilage so mapped at the later time, and determining the loss in thickness or regional volume of the cartilage between the later and initial times. The 3D map may be a thickness map, a biochemical map or a combination.

Another aspect of the invention is a method for assessing the condition of cartilage in a joint of a human, which method comprises electronically transferring an electronically-generated image of a cartilage of the joint from a transferring device to a receiving device located distant from the transferring device; receiving the transferred image at the distant location; converting the transferred image to a degeneration pattern of the cartilage; and transmitting the degeneration pattern to a site for analysis.

Another aspect of the invention is a method for determining the volume of cartilage loss in a region of a cartilage defect of a cartilage in joint of a mammal. The method comprises (a) determining the thickness, $D_N$, of the normal cartilage near the cartilage defect; (b) obtaining the thickness of the cartilage defect, $D_D$, of the region; (c) subtracting $D_D$ from $D_N$ to give the thickness of the cartilage loss, $D_L$; and (d) multiplying the $D_L$ value times the area of the cartilage defect, $A_D$, to give the volume of cartilage loss.

Still another aspect of the invention is a method of estimating the change of a region of cartilage in a joint of a mammal over time. The method comprises (a) estimating the width or area or volume of a region of cartilage at an initial time $T_1$, (b) estimating the width or area or volume of the region of cartilage at a later time $T_2$, and (c) determining the change in the width or area or volume of the region of cartilage between the initial and the later times.

Still another aspect of the invention is a method of estimating the loss of cartilage in a joint. The method comprises (a) defining a 3D object coordinate system of the joint at an initial time, $T_1$; (b) identifying a region of a cartilage defect within the 3D object coordinate system; (c) defining a volume of interest around the region of the cartilage defect whereby the volume of interest is larger than the region of cartilage defect, but does not encompass the entire articular cartilage; (d) defining the 3D object coordinate system of the joint at a second timepoint, $T_2$; (e) placing the identically-sized volume of interest into the 3D object coordinate system at timepoint $T_2$ using the object coordinates of the volume of interest at timepoint $T_1$; (f) and measuring any differences in cartilage volume within the volume of interest between timepoints $T_1$, and $T_2$.

Another aspect of this invention is a method for providing a biochemically-based map of joint cartilage. The method comprises measuring a detectable biochemical component throughout the cartilage, determining the relative amounts of the biochemical component throughout the cartilage; mapping the amounts of the biochemical component through the cartilage; and determining the areas of cartilage deficit by identifying the areas having an altered amount of the biochemical component present.

Once a map is obtained, it can be used in assessing the condition of a cartilage at an initial time and over a time period. Thus, the biochemical map may be used in the method aspects of the invention in a manner similar to the cartilage thickness map.

Another aspect of this invention is a method for assessing the condition of cartilage in a joint from a distant location. The method comprises electronically transferring an electronically-generated image of a cartilage of the joint from a transferring device to a receiving device located distant from the transferring device; receiving the transferred image at the distant location; converting the transferred image to a degeneration pattern of the cartilage; and transmitting the degeneration pattern to a site for analysis.

Another aspect of the invention is a kit for aiding in assessing the condition of cartilage in a joint of a mammal, which kit comprises a software program, which when installed and executed on a computer reads a cartilage degeneration pattern presented in a standard graphics format and produces a computer readout showing a cartilage thickness map of the degenerated cartilage.

Another aspect of this invention is a method for assessing the condition of a subject's cartilage in a joint, the method comprises obtaining a three dimensional biochemical representation of the cartilage, obtaining a morphological representation of the cartilage, and merging the two representations, and simultaneously displaying the merged representations on a medium. The merged representations are then used to assess the condition of a cartilage, estimate the loss of cartilage in a joint, determining the volume of cartilage loss in a region of cartilage defect, or estimating the change of a region of cartilage at a particular point in time or over a period of time.

A method for correlating cartilage image data, bone image data, and opto-electrical image data for the assessment of the condition of a joint, which method comprises (a) obtaining the bone image data of the joint with a set of skin reference markers positioned in externally near the joint, (b) obtaining the opto-electrical image data of the joint with a set of skin reference markers positioned in the same manner as (a), and (c) using the skin reference markers to correlate the images obtained in (a) and (b) with each other, wherein each skin reference marker is detectable in the bone data and the opto-electrical data. The method also can be used to further evaluate cartilage image data that is obtained using a similarly positioned set of skin reference markers.

Another aspect of the invention is a skin reference marker that comprises (a) a material detectable by an imaging technique; (b) a container for holding the material, (c) a material that causes the container to adhere to the skin of a human, and (d) a reflective material placed on the surface of the container.

Another aspect of the invention is a biochemical map of a cartilage that comprises a three-dimensional representation of the distribution of the amount of the biochemical component throughout the cartilage.

Another aspect of the invention is a method for providing a biochemically-based map of joint cartilage of a mammal, wherein the joint comprises cartilage and associated bones on either side of the joint, which method comprises (a) measuring a detectable biochemical component throughout the cartilage; (b) determining the relative amounts of the biochemical component throughout the cartilage; (c) mapping the amounts of the biochemical component in three dimensions through the cartilage; and (d) determining the areas of abnormal joint cartilage by identifying the areas having altered amounts of the biochemical component present.

Another aspect of the invention is a method for deriving the motion of bones about a joint from markers placed on the skin, which method comprises (a) placing at least three external markers on the patient's limb segments surrounding the joint, (b) registering the location of each marker on the patient's limb while the patient is standing completely still and while moving the limb, (c) calculating the principal axis, principal moments and deformation of rigidity of the cluster of markers, and (d) calculating a correction to the artifact induced by the motion of the skin markers relative to the underlying bone.

Another aspect of the invention is a system for assessing the condition of cartilage in a joint of a human, which system comprises (a) a device for electronically transferring a cartilage degeneration pattern for the joint to a receiving device located distant from the transferring device; (b) a device for receiving the cartilage degeneration pattern at the remote location; (c) a database accessible at the remote location for generating a movement pattern for the joint of the human wherein the database includes a collection of movement patterns of human joints, which patterns are organized and can be accessed by reference to characteristics such as type of joint, gender, age, height, weight, bone size, type of movement, and distance of movement; (d) a device for generating a movement pattern that most closely approximates a movement pattern for the human patient based on the characteristics of the human patient; (e) a device for correlating the movement pattern with the cartilage degeneration pattern; and (f) a device for transmitting the correlated movement pattern with the cartilage degeneration pattern back to the source of the cartilage degeneration pattern.

A method for assessing the condition of the knee joint of a human patient, wherein the knee joint comprises cartilage and associated bones on either side of the joint, which method comprises (a) obtaining the patient's magnetic resonance imaging (MRI) data of the knee showing at least the bones on either side of the joint, (b) segmenting the MRI data from step (a), (c) generating a geometrical representation of the bone of the joint from the segmented MRI data, (d) assessing the patient's gait to determine the load pattern or the cartilage contact pattern of the articular cartilage in the joint during the gait assessment, and (e) correlating the load pattern or cartilage contact pattern obtained in step (d) with the geometrical representation obtained in step (c).

Another aspect of the invention is a method of assessing the rate of degeneration of cartilage in the joint of a mammal, wherein the joint comprises cartilage and the bones on either side of the cartilage, which method comprises. (a) obtaining a cartilage degeneration pattern of the joint that shows an area of greater than normal degeneration, (b) obtaining a movement pattern of the joint that shows where the opposing cartilage surfaces contact, (c) comparing the cartilage degeneration pattern with the movement pattern of the joint, and (d) determining if the movement pattern shows contact of one cartilage surface with a portion of the opposing cartilage surface showing greater than normal degeneration in the cartilage degeneration pattern.

Another aspect of the invention is a method for monitoring the treatment of a degenerative joint condition in a mammal, wherein the joint comprises cartilage and accompanying bones on either side of the joint, which method comprises (a) comparing the movement pattern of the joint with the cartilage degeneration pattern of the joint; (b) determining the relationship between the movement pattern and the cartilage degeneration pattern; (c) treating the mammal to minimize further degeneration of the joint condition; and (d) monitoring the treatment to the mammal.

Still another aspect of the invention is a method of assessing the condition of a joint in a mammal, wherein the joint comprises cartilage and accompanying bones on either side of the joint, which method comprises (a) comparing the movement pattern of the joint with the cartilage degeneration pattern of the joint; and (b) determining the relationship between the movement pattern and the cartilage degeneration pattern.

Another aspect of the invention is a method of assessing a joint disease that includes obtaining an electronic image of a joint. The image is electronically evaluated to obtain at least one of volume, area, thickness, curvature, geometry, shape, biochemical contents, signal intensity and relaxation time of normal and/or diseased tissue. One or more axes related to the joint is determined.

In related embodiments of the invention, the axis determined may be an anatomic axis and/or a biomechanical axis. Obtaining the electronic image may include performing an MRI, a CT, a spiral CT, an ultrasound and/or an x-ray. Obtaining the electronic image may include using a contrast agent. At least one of a cast, physical model and/or mold may be created of all or portions of said joint. The method may further include guiding a treatment as a function of said electronically evaluating and said determining an axis. The guiding may include optimizing the alignment of a treatment, such as optimizing biomechanical forces applied to the joint.

Another aspect of the invention is a method of assessing a joint disease. The method includes obtaining an electronic image of a joint. The image is electronically evaluated to obtain at least one of volume, area, thickness, curvature, geometry, shape, biochemical contents, signal intensity and relaxation time of normal and/or diseased tissue. At least one of a cast, a physical model, and a mold is created of all or a portion of the joint. One or more movement patterns of the joint is evaluated.

In related embodiments of the invention, evaluation of the movement pattern includes testing the joint in at least one or more flexion angles and/or extension angles, at least one or more abduction angles, at least one or more adduction angles and/or at least one or more rotation angles.

Yet another aspect of the invention is a method of assessing a joint disease that includes obtaining an electronic image of a joint. The image is electronically evaluated to obtain at least one of volume, area, thickness, curvature, geometry, shape, biochemical contents, signal intensity and relaxation time of normal and/or diseased cartilage. A cast, physical model, and/or a mold is created of all or a portion of said joint.

Still another aspect of the invention is a method of assessing a joint disease that includes obtaining an electronic image of a joint. The image is electronically evaluated to obtain at least one of volume, area, thickness, curvature, geometry, shape, biochemical contents, signal intensity and relaxation time of normal and/or diseased cartilage and subchondral bone. A cast, a physical model, and/or a mold is created of all or a portion of said joint.

Another aspect of the invention is a method of assessing a joint disease that includes obtaining an electronic image of a joint. The image is electronically evaluated to obtain at least one of volume, area, thickness, curvature, geometry, shape, biochemical contents, signal intensity or relaxation time of the joint. Cartilage or subchondral bone associated with the joint is segmented. A cast, physical model, and/or mold of all or a portion of said joint is created.

In related embodiments, the segmention includes using at least one of an active contour algorithm, a livewire algorithm, thresholding, a seed growing algorithm, a texture based algorithm and a model based segmentation algorithm.

In accordance with another aspect of the invention, an articular repair system to treat a mammalian with joint disease including arthritis is presented. The articular repair system has a shape that substantially follows the physical shape of the joint.

In related embodiments of the invention, the physical shape of the joint is determined by the shape of articular cartilage, the subchondral bone, and/or the shape of articular cartilage and subchondral bone. The articular repair system may be metallic. The articular repair system may replace all or portions of one or more articular surfaces. The articular repair system may substantially conform to a tibia, a femur, an acetabulum, or a femoral head. The physical shape may be one or more portions of a tibia or femur, including one or more underlying convexities or concavities.

In accordance with another aspect of the invention, an articular repair system to treat a mammalian with joint disease including arthritis is presented. The articular repair system has a thickness that substantially matches the thickness of the articular cartilage.

In accordance with still another aspect of the invention, a method of assessing cartilage disease or damage in a joint of a living subject is presented. The joint includes cartilage and/or accompanying bone on either side of the joint. The method includes (a) obtaining a three-dimensional volumetric representation of cartilage of said joint demonstrating volume or thickness or biochemical contents or relaxation time of both normal and diseased or damaged cartilage of said joint, and (b) electronically estimating thickness or area or volume of lost cartilage tissue relative to expected cartilage tissue in absence of disease or damage. The representation is used to devise a treatment for damaged or diseased cartilage and/or bone.

In related embodiments of the invention, the thickness, area or volume of said cartilage tissue that has been lost is obtained by determining a margin between said diseased or damaged cartilage and the normal cartilage in the three-dimensional map. The margin may be determined by measuring changes in the thickness of said normal and said diseased cartilage, the biochemical content of said normal and said diseased cartilage, and/or in the relaxation time of the normal and the diseased cartilage. The method may be carried out at an initial time $T_1$ and at a later time $T_2$ and said determination includes a determination of amount of cartilage lost between $T_1$ and $T_2$. The amount of cartilage tissue lost may be determined as thickness or area or volume or content in one or more biochemical components of said cartilage tissue lost. The thickness, area, volume, or content of said cartilage tissue lost may be obtained by determining a margin between diseased or damaged cartilage and normal cartilage. The change in the diseased cartilage or the cartilage tissue lost may be determined without matching data obtained at $T_1$ and $T_2$.

Yet another aspect of the invention is a method of assessing cartilage disease or damage in a joint of a living subject is presented. The joint includes cartilage and/or bone on either side of the joint. The method includes obtaining a three-dimensional volumetric representation of cartilage of the joint. The volumetric representation includes information on volume, thickness, curvature, shape and/or relaxation time of both normal and damaged cartilage of said joint. A volume of interest smaller than the articular cartilage surface is electronically placed in or around an area of diseased or damaged cartilage. The representation is used to devise a treatment for damaged or diseased cartilage or bone.

Still another aspect of the invention is a method of assessing cartilage disease or damage in a joint of a living subject. The joint includes cartilage and/or bone on either side of the joint. The method includes obtaining a three-dimensional dataset of the articular cartilage that includes information on volume, thickness, biochemical contents and/or relaxation time of said cartilage. A subregion that is smaller than the entire articular surface is electronically evaluated. A quantitative measurement is performed of volume, thickness, biochemical contents and/or relaxation time of the cartilage in the subregion. The representation is used to devise a treatment for damaged or diseased cartilage or bone.

Another aspect of the invention is a method of assessing articular damage in a joint of a living subject. The joint includes cartilage and/or bone on either side of the joint. The method includes obtaining a three-dimensional dataset of the joint that includes information on volume, thickness, shape, biochemical contents and/or relaxation time of the cartilage and/or bone. The cartilage and/or said bone is segmented. The segmentation is used to devise a treatment for damaged or diseased cartilage or bone. The method may further include transferring the dataset to a remote site.

Still another aspect of the invention is a method of assessing articular damage in a joint of a living subject. The joint includes cartilage and/or bone on either side of the joint. The method includes obtaining a three-dimensional dataset of the joint that includes information on volume, thickness, shape, biochemical contents and/or relaxation time of said cartilage or bone. A normal or near normal outer cartilage surface is reconstructed over an area of cartilage loss or diseased cartilage.

In accordance with related embodiments of the invention, the reconstructed outer cartilage surface may be used to guide, devise or select a treatment for damaged or diseased cartilage or bone. The dataset may be transferred to a remote site.

Other aspects of the invention may be apparent upon further reading the specification and claims of the patent application.

BRIEF DESCRIPTION OF THE DRAWINGS

In the accompanying drawings:

FIG. 13A has the subject in supine position and FIG. 13B has the subject in an upright position.

FIGS. 9A-9C show patient position and application of imaging coil and tracker coil for kinetic MR imaging of the knee. Patient is in upright weight-bearing position for active flexion and extension study of the knee.

FIG. 10A is a baseline with a knee and neutral position. 10B is a follow-up with knee and external rotation with a 3D view that is the identical to the one used in 10A but the difference in knee rotation is apparent. In FIG. 10C, transformation and re-registration of Scan B into the object coordinate system of Scan A shows the anatomic match to A can be excellent.

FIGS. 15A and 15B show the marker names and locations for the standard point-cluster technique protocol.

FIG. 24A shows that a volume of interest (VOI) is selected. The cartilage volume within this VOI is measured. Two points $P_1$ and $P_2$ on the OCS are selected on either side of the defect. The distances $d_1$ and $d_2$ to the ICS are measured.

FIG. 24B shows that the ICS-OCS distance values between $P_1$ and $P_2$ can be determined by means of a linear interpolation.

FIG. 24C shows that the interpolated OCS can be constructed using the interpolated distance values.

DETAILED DESCRIPTION

Overview

Figure 1:
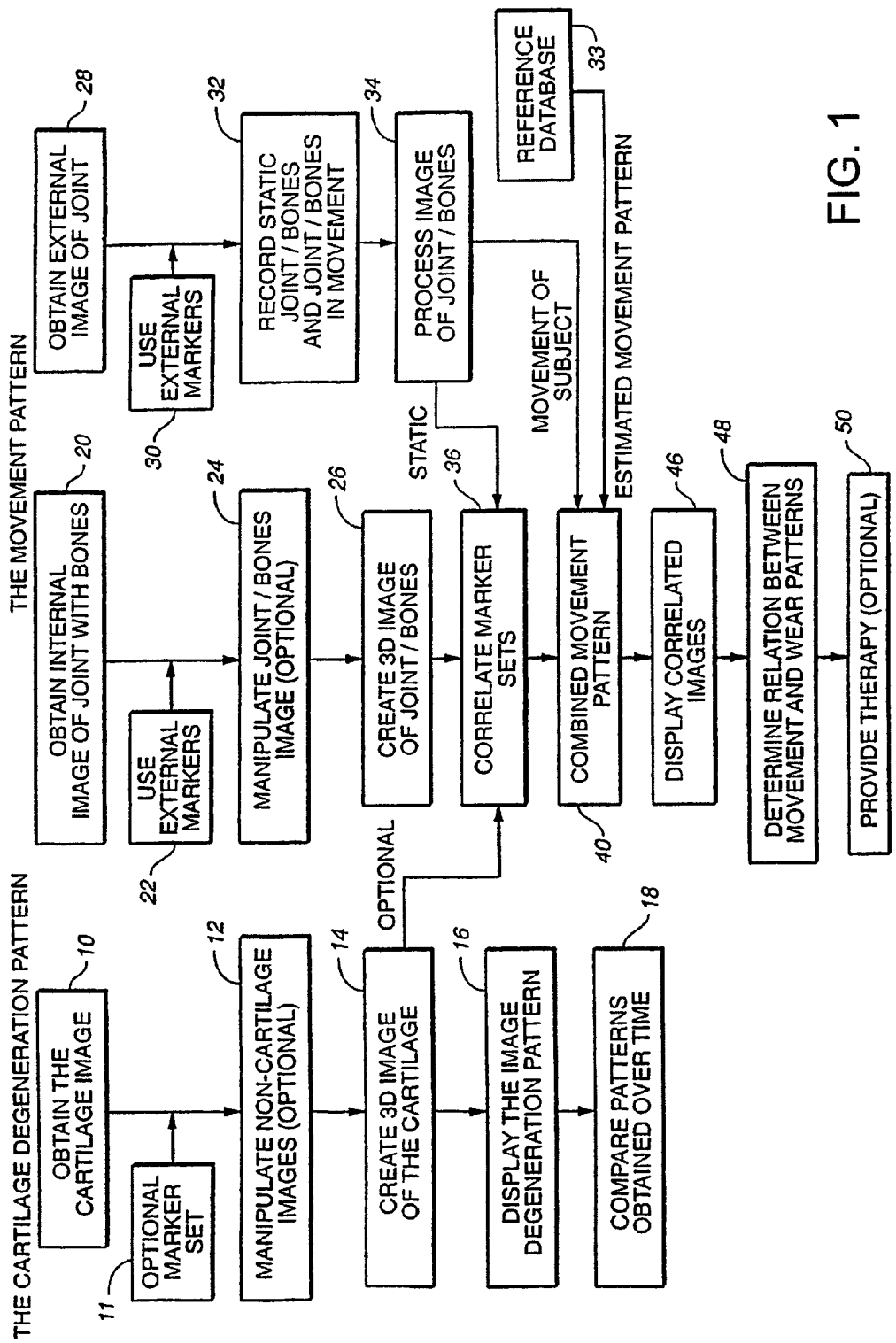
FIG. 1 shows an overview schematic representation of some aspects of the invention of this application.

FIG. 1 is a schematic overview of some of the various aspects of the invention. While a complete description of the many aspects of the invention is found in the specification and claims, the schematic overview gives some of the broad aspects of the invention.

This invention relates to assessing the condition of a joint in a mammal. One aspect is a method for such an assessment. The assessment can be done using internal images, or maps, of the cartilage alone or in combination with a movement pattern of the joint. If used alone, a map obtained at an initial time is compared with a map obtained at a later time to provide a view of the change in cartilage over time. Another aspect is a method is comparing the movement pattern for a joint of a subject being studied with the cartilage degeneration pattern of the subject, then determining the relationship between the movement pattern and the degeneration pattern. If, in determining the relationship between the two patterns, one finds that the movement pattern has caused the degeneration pattern or will continue to adversely affect the degeneration pattern, therapy can be prescribed to minimize the adverse effects, such as further degeneration or inflammation.

In overview, some of the systems and methods of this invention are illustrated by the flow chart in the attached FIG. 1. FIG. 1 is based on the full range of processes, preferably applied to a knee and surrounding cartilage.

In FIG. 1, the first step 10 represents obtaining an image of the cartilage itself. This is typically achieved using MRI techniques to take an image of the entire knee and then, optionally, manipulating (e.g., "subtracting out" or "extracting") the non-cartilage images as shown in step 12. Non-cartilage images typically come from bone and fluid. Preferably, the MRI is taken using external markers to provide reference points to the MRI image (step 11).

If the cartilage is imaged with a 2D MRI acquisition technique, the resulting stack of 2D images so obtained can be combined into a 3D image, as indicated in step 14. A preferred alternative is to use 3D MRI acquisition techniques to acquire a 3D image directly. In either case, the same "non-cartilage image extraction techniques referred to in step 12 can be used.

With a full 3D image captured, various "maps" or displays of the cartilage can be constructed to give a cartilage degeneration pattern. This is represented by step 16. One such display can, for example, be a color-coding of a displayed image to reflect the thickness for the cartilage. This will allow easy visual identification of actual or potential defects in the cartilage.

Together with or independently of the cartilage imaging, and as represented by parallel step 20, a 3D image of the knee joint is taken, again preferably using MRI. Many of the same techniques as applied in steps 10 to 14 are used to do this. However, as illustrated by sub-step 22, it is useful to define and register a skin-external frame of reference around the joint. This is achieved by placing fiduciary markers on the skin around the outside of the knee (step 22) prior to taking the image.

In addition to an image extraction technique (as described above in step 12), an image is manipulated to enhance the image of the position of the markers (step 24). The resulting manipulated image is used to give a 3D image of the joint and associated bones (step 26).

With the markers in place, and as shown by step 30, an additional set of markers is placed on the skin along the outside of the leg, and an external image of the limb is obtained. Using at least two cameras, images are then taken of the subject in a static state. In addition, images are also taken of the subject while moving. This is shown collectively by step 32. The images obtained are then processed to relate the movement of the skin relative to the bone. In addition, certain calculations are performed, for example, the center of mass is calculated. These manipulations are shown in Step 34. Further, as the fiduciary markers are still in place during the video image capture, a correlation between the fiduciary and the additional set of markers can be made. This is shown in step 36.

Once this marker-to-marker correlation is made, the static 3D image of the joint (with associated fiduciary markers) and the movement images of the leg bones (also with fiduciary markers in place) can be combined. The fiduciary markers, therefore, serve as baseline references. The combination (step 40) of 3D cartilage image (from step 14), 3D knee joint image (step 26), and the moving leg co-ordinates (step 34) will, after appropriate corrections, result in a displayable, 3D motion image of the joint moving as per step 46.

The moving images, showing the contact areas of the knee joint can be used in conjunction with the various "maps" or displays generated at step 16 to provide a visual indication of potential or actual cartilage defects and help in determining their relation between movement and degeneration patterns. This is shown in step 48.

Furthermore, as the various images are supported by actual mathematical quantification, real measurements (such as cartilage thickness) can be taken and compared with later or earlier measurements and/or imaging. This allows the tracking of the progression of a defect, or conversely, continued tracking of healthy cartilage. This aids a health worker in providing therapy for the patients. The method allows monitoring and evaluation of remedial actions as well as possible treatment prescriptions.

Thus, this invention discloses, for example, a method to examine the relationship between articular cartilage morphology and the functional load bearing areas of a knee joint measured during movement. The method includes enhanced imaging techniques to reconstruct the volumetric and biochemical parameters of the articular cartilage in three dimensions; and a method for in vivo kinematic measurements of the knee. The kinematic measurement permits direct in vivo measurements of complete six-degrees of freedom motion of the femur or the tibia or associated bones during normal activities. This permits the study of load bearing of articular cartilage during movement. In particular, this method can aid in locating cartilage defects relative to the changing load bearing areas of the knee joint during daily activities. While the various aspects of the invention are useful in mammals generally, they are particularly useful for human patients.

Obtaining the Cartilage Degeneration Pattern
Imaging Articular Cartilage

In general, the joint of a patient is that place of union, more or less movable, between two or more bones. A joint comprises cartilage and other elements such as the accompanying bones on either side of the joint, fluid, and other anatomical elements. Joints are classified into three general morphological types: fibrous, cartilaginous, and synovial. This invention is particularly useful for assessing synovial joints, particularly the knee.

In obtaining an image of the cartilage of a joint in a mammal, a number of internal imaging techniques known in the art are useful for electronically generating a cartilage image. These include magnetic resonance imaging (MRI), computed tomography scanning (CT, also known as computerized axial tomography or CAT), and ultrasound imaging techniques. Others may be apparent to one of skill in the art. MRI techniques are preferred.

MRI, with its superior soft tissue contrast, is the best technique available for assessing tissue and its defects, for example articular cartilage and cartilage lesions, to obtain a cartilage degeneration can provide morphologic information about the area of damage. Specifically, changes such as fissuring, partial or full thickness cartilage loss, and signal changes within residual cartilage can be detected.

The reason MR imaging techniques are particularly suitable for cartilage is because they can provide accurate assessment of cartilage thickness, demonstrate internal cartilage signal changes, evaluate the subchondral bone for signal abnormalities, and demonstrate morphologic changes of the cartilage surface.

MRI provides several important advantages over other techniques in this invention. One advantage is good contrast between cartilage, bone, joint fluid, ligaments, and muscle in order to facilitate the delineation and segmentation of the data sets. Another is the coverage of the entire region of interest in a single scan within acceptable acquisition times. For a brief discussion of the basic MRI principles and techniques, see MRI Basic Principles and Applications, Second Edition, Mark A. Brown and Richard C. Semelka, Wiley-Liss, Inc. (1999).

MRI employs pulse sequences that allow for better contrast of different parts of the area being imaged. Different pulse sequences are better fitted for visualization of different anatomic areas, for example, hyaline cartilage or joint fluid. More than one pulse sequence can be employed at the same time. A brief discussion of different types of pulse sequences is provided below.

High Resolution 3D MRI Pulse Sequences

Routine MRI pulse sequences available for imaging tissue, such as cartilage, include conventional T1 and T2-weighted spin-echo imaging, gradient recalled echo (GRE) imaging, magnetization transfer contrast (MTC) imaging, fast spin-echo (FSE) imaging, contrast enhanced imaging, rapid acquisition relaxation enhancement, (RARE) imaging, gradient echo acquisition in the steady state, (GRASS), and driven equilibrium Fourier transform (DEFT) imaging. As these imaging techniques are well known to one of skill in the art, e.g. someone having an advanced degree in imaging technology, each is discussed only generally hereinafter. While each technique is useful for obtaining a cartilage degeneration pattern, some are better than others.

Conventional T1 and T2-Weighted Spin-Echo Imaging

Conventional T1 and T2-weighted MRI depicts articular cartilage, and can demonstrate defects and gross morphologic changes. T1-weighted images show excellent intra-substance anatomic detail of hyaline cartilage. However, T1-weighted imaging does not show significant contrast between joint effusions and the cartilage surface, making surface irregularities difficult to detect. T2-weighted imaging demonstrates joint effusions and thus surface cartilage abnormalities, but since some components of cartilage have relatively short T2 relaxation times, these are not as well depicted as other preferred imaging.

Gradient-Recalled Echo Imaging

Gradient-recalled echo imaging has 3D capability and ability to provide high resolution images with relatively short scan times. Fat suppressed 3D spoiled gradient echo (FS-3D-SPGR) imaging has been shown to be more sensitive than standard MR imaging for the detection of hyaline cartilage defects in the knee.

Magnetization Transfer Contrast Imaging

Cartilage, as well as other ordered tissues, demonstrate the effects of magnetization transfer. Magnetization transfer imaging can be used to separate articular cartilage from adjacent joint fluid and inflamed synovium.

Fast Spin-Echo Imaging

Fast spin-echo imaging is another useful pulse sequence to evaluate articular cartilage. Incidental magnetization transfer contrast contributes to the signal characteristics of articular cartilage on fast spin-echo images and can enhance the contrast between cartilage and joint fluid. Sensitivity and specificity of fast spin-echo imaging have been reported to be 87% and 94% in a study with arthroscopic correlation.

Contrast Enhanced Imaging

The use of gadolinium for imaging of articular cartilage has been applied in several different forms. Direct magnetic resonance (MR) arthrography, wherein a dilute solution containing gadolinium is injected directly into the joint, improves contrast between cartilage and the arthrographic fluid. Indirect MR arthrography, with a less invasive intravenous injection, can also been applied. Gadolinium enhanced imaging has the potential to monitor glycosaminoglycan content within the cartilage, which may have implications for longitudinal evaluations of injured cartilage.

Driven Equilibrium Fourier Transform

Another 3D imaging method that has been developed is based on the driven equilibrium fourier transform (DEFT) pulse sequence (U.S. Pat. No. 5,671,741), and is specifically designed for cartilage imaging. DEFT provides an effective tradeoff between T2/T1 weighting and spin density contrast that delineates the structures of interest in the knee. Contrast-to-noise ratio between cartilage and joint fluid is greater with DEFT than with spoiled gradient echo (SPGR). DEFT is an alternative approach to SPGR. DEFT contrast is very well suited to imaging articular cartilage. Synovial fluid is high in signal intensity, and articular cartilage intermediate in signal intensity. Bone is dark, and lipids are suppressed using a fat saturation pulse. Hence, cartilage is easily distinguished from all of the adjacent tissues based on signal intensity alone, which will greatly aid segmentation and subsequent volume calculations.

Figure 2:
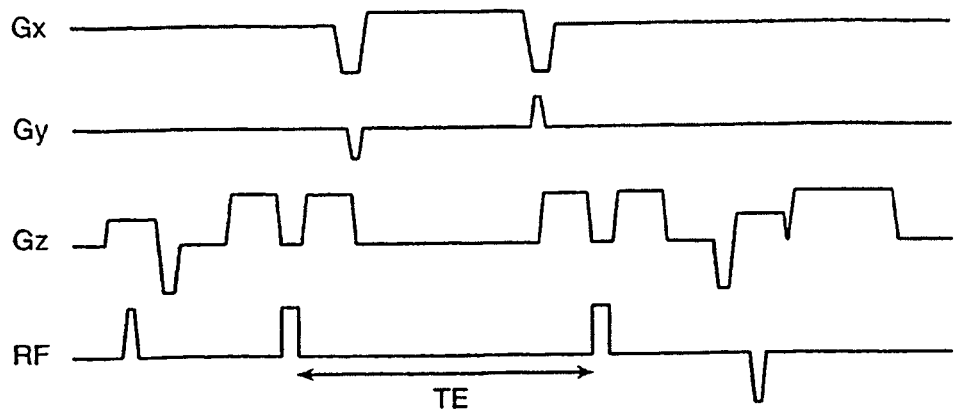
FIG. 2 shows a DEFT pulse sequence.
Figure 3A:
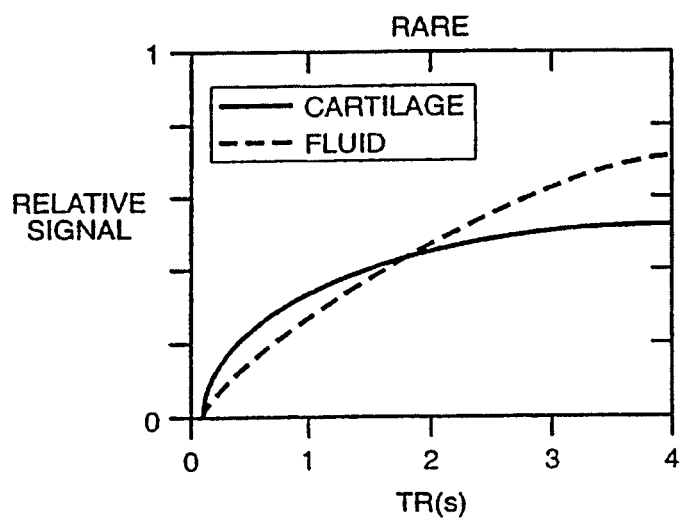
FIG. 3A shows the signal levels for cartilage and synovial fluid with RARE (FIG. 3A) and DEFT (FIG. 3B) pulse sequences, both TE=14 milliseconds.
Figure 3B:
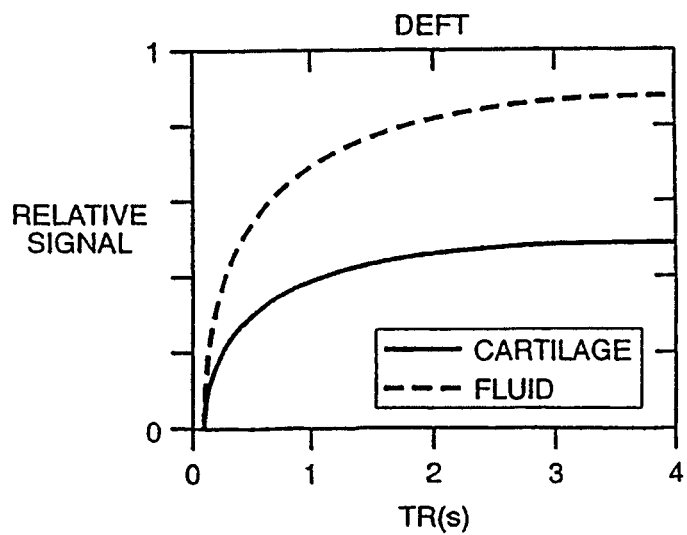

The basic DEFT pulse sequence is shown in FIG. 2. A conventional spin echo pulse sequence was followed by an additional refocusing pulse to form another echo, and then a reversed, negated, excitation pulse to return any residual magnetization to the +z axis. This preserved the magnetization of longer T2 species, such as synovial fluid. Typical MRI parameters for cartilage are a T1-relaxation time of 900 Milliseconds (ms) and a T2-relaxation time of 40 ms, while synovial fluid has a T1-relaxation time of 3000 ms and a T2-relaxation time of 200 ms. In addition, synovial fluid has a 30% greater proton density than cartilage. The signal levels of cartilage and synovial fluid were plotted in FIG. 3 for a RARE pulse sequence and for DEFT, and show that DEFT maintains excellent contrast for any relaxation time (TR). It achieves this contrast while maintaining a signal-to-noise ratio (SNR) efficiency (SNR)/($T_{acquisition}$)) that is equal to or better than other methods with much lower contrast, such as T1-weighted GRASS.

DEFT was compared with a fast spin-echo (FSE), a gradient-echo (GRE), and a spoiled gradient-echo (SPGR) sequence with parameters similar to the ones published by Disler et al. The patella was scanned in 10 normal volunteer knees using a 1.5 T whole-body system (GE Signa) with a 3 inch surface coil. All images were acquired with field of view (FOV) 10×10 cm, matrix 256×256 elements, slice thickness 4 mm using fat-saturation. DEFT (400/15 [TR/TE in msec], 2 NEX (number of excitations), FSE (3500/15, echo train length [ETL] 8, 2 NEX (number of excitations), FSE (3500/15, ETL 4, 2 NEX), GRE (400/20, 30°, 2 NEX), and SPGR (50/15, 30° [flip angle], 2 NEX) images were obtained. Contrast-to-noise ratios (CNR) between cartilage and joint fluid were calculated as:

$$CNR = |(SI_{Joint\ Fluid} - SI_{cartilage})/SI_{Background\ Noise}| \quad [Eq.\ 1]$$

Contrast (C) between cartilage and joint fluid was calculated as:

$$C = |[(SI_{joint\ Fluid} - SI_{cartilage})/SI_{Joint\ Fluid}] \times 100| \quad [Eq.\ 2]$$

Figure 4:
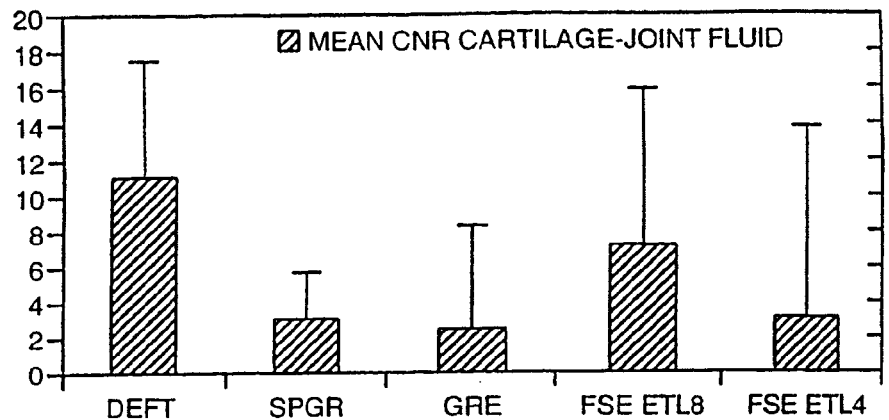
FIG. 4 shows the mean contrast to noise ratio (CNR) of cartilage to joint fluid for various MRI pulse sequences.
Figure 5:
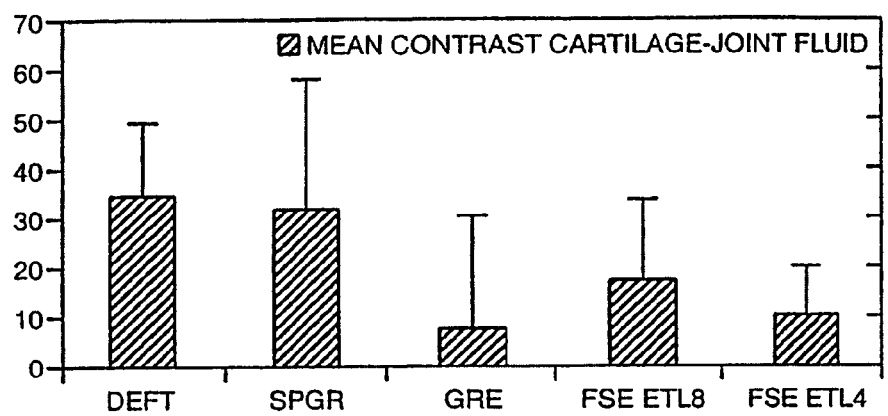
FIG. 5 shows the mean contrast for cartilage and joint fluid for various MRI pulse sequences.

In the equations SI is signal intensity. DEFT demonstrated greater contrast-to-noise ratio and contrast between cartilage and joint fluid than SPGR, GRE, and FSE sequences (FIGS. 4 & 5). Cartilage had intermediate signal intensity with DEFT, while joint fluid was high in signal intensity. The difference in CNR between DEFT and SPGR was statistically significant ($p<0.001$). Cartilage morphology, i.e. cartilage layers, were consistently best delineated with the DEFT sequence. At the resolution used in this study, FSE sequences suffered from image blurring. Blurring was improved with ETL 4 when compared to ETL8 nonetheless, even with ETL 4, cartilage morphology seen on FSE images was inferior to the DEFT sequence. In light of these results, DEFT imaging is a preferred MRI technique.

Another Application of DEFT

Figure 6:
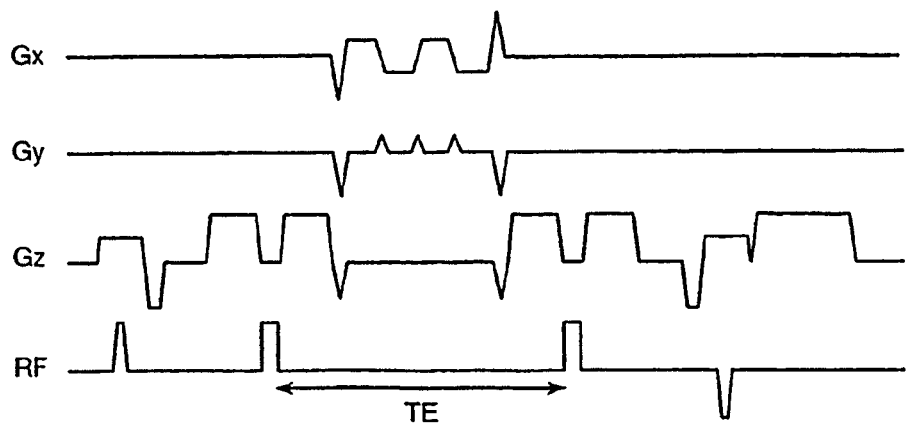
FIG. 6 shows a DEFT acquisition using non-selective refocusing pulses to maximize the SNR efficiency and a partial K-Echo-Plainer acquisition gradients in order to minimize the required scan time for 3D volume.

DEFT was combined with a partial k-space echo-planar data acquisition. This pulse sequence is illustrated in FIG. 6 above. A slab selective pulse in z defines the imaging volume, which is then resolved with phase-encoding gradients in the y and z axes, and an oscillating EPI gradient in the x axis.

Figure 7:
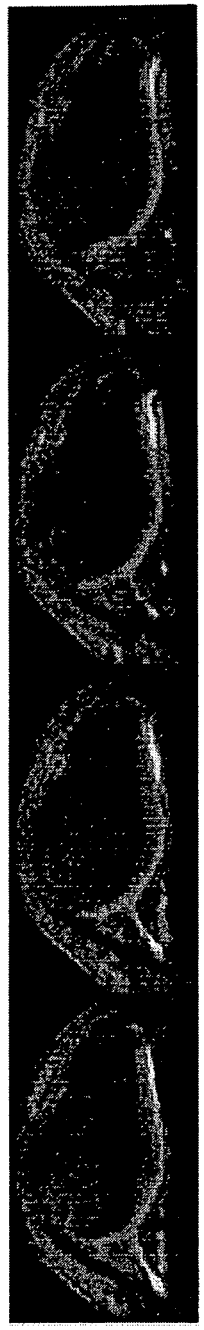
FIG. 7 shows four sample images acquired with a DEFT pulse sequence combined with a partial K-Echo-Plainer acquisition in order to provide efficient 3D coverage.

Example images acquired with this approach are shown in FIG. 7. This case was optimized for resolution, in order to image the patellar cartilage. The EPI readout acquired 5 echoes for each DEFT sequence. Partial k-space acquisition collected only 60% of the data along the x-axis. Correction for the missing data was performed using a homodyne reconstruction. The image matrix was 192×192×32, with a resolution of 0.5×0.5×2.5 mm, resulting in a 10×10×8 cm FOV. The echo time TE was 22 ms, and the TR was 400 ms. Fat was suppressed with a fat presaturation pulse. The total scan time for this acquisition was 5 minutes.

Additional image studies that can be performed using this approach may require greater spatial coverage, but one can permit slightly less spatial resolution, and a longer scan time similar to the one used with the 3D SPGR approach. If one relaxes the resolution to 0.75×0.75×1.5 mm, and doubles the z slab thickness and z phase encodes, the result will be a FOV of 15×15×16 cm, and a total scan time of approximately 15 minutes, which exactly fits the desired scan protocol. Similar to the 3D SPGR acquisition, one can acquire a first 3D DEFT scan in the sagittal plane with fat saturation. The 3D DEFT acquisition can then be repeated without fat saturation using the identical parameters and slice coordinates used during the previous acquisition with fat saturation. The resultant non-fat-saturated 3D DEFT images can be used for 3D rendering of the femoral and tibial bone contours.

In summary, Driven Equilibrium Fourier Transform is a pulse sequence preferred for cartilage imaging that provides higher contrast-to-noise ratios and contrast between cartilage and joint fluid than SPGR, GRE, and FSE sequences. Cartilage morphology is better delineated with DEFT sequences than with SPGR, GRE, and FSE images. The combination of high anatomic detail and high cartilage-joint fluid CNR and contrast may render this sequence particularly useful for longitudinal studies of cartilage in patients with osteoarthritis.

A Representative Example of MR Imaging is described below:

A MR image can be performed using a whole body magnet operating at a field strength of 1.5 T (GE Signa, for example, equipped with the GE SR-120 high speed gradients [2.2 Gauss/cm in 184 μsec risetimes]). Prior to MR imaging, external markers filled with Gd-DTPA (Magnevist®, Berlex Inc., Wayne, N.J.) doped water (T1 relaxation time approximately 1.0 sec) can be applied to the skin around the knee joint and optionally at the same positions used for gait analysis in a biomotion laboratory (discussed below). The external markers can be included in the field of view of all imaging studies. Patients can be placed in the scanner in supine position. After an axial scout sequence, coronal and sagittal T1-weighted images of the femur can be acquired using the body coil (spin-echo, TR=500 msec, TE=15 msec, 1 excitation (NEX), matrix 256×128 elements, field of view (FOV) 48 cm, slice thickness 7 mm, interslice spacing 1 mm). The scanner table can then be moved to obtain coronal and sagittal images of the knee joint and tibia using the same sequence parameters. These T1-weighted scans can be employed to identify axes through the femur and tibia which can be used later for defining the geometry of the knee joint. The knee can then be placed in the knee coil with the joint space located in the center of the coil. The knee can be secured in the coil with padding. Additionally, the foot and ankle region can be secured in neutral position to the scanner table using adhesive tape in order to minimize motion artifacts. A rapid scout scan can be acquired in the axial plane using a gradient echo sequence (GRASS, 2D Fourier Transform (2 DFT), TR=50 msec, TE=10 msec, flip angle 40°, 1 excitation (NEX), matrix 256×128 elements, field of view (FOV) 24 cm, slice thickness 7 mm, interslice spacing 3 mm). This scout scan can be used to demonstrate the position of the knee joint space in the coil and to prescribe all subsequent high resolution imaging sequences centered over the joint space. Additionally, using the graphic, image based sequence prescription mode provided with the scanner software, the scout scan can help to ensure that all external markers around the knee joint are included in the field of view of the high resolution cartilage sensitive MR sequences.

Figure 8B:
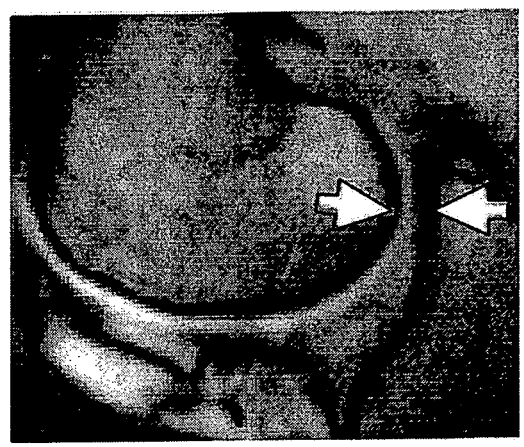
FIGS. 8A and 8B show a 3-point Dixon GRE image of the articular cartilage of medial fermorotibial compartment in a normal 35-year old volunteer.
Figure 8A:
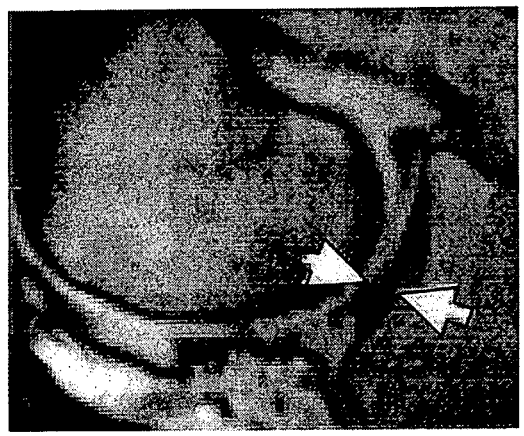

There are several issues to consider in obtaining a good image. One issue is good contrast between cartilage, bone, joint fluid, ligaments, and muscle in order to facilitate the delineation and segmentation of the data sets. Another is the coverage of both condyles of the knee in a single scan within acceptable acquisition times. In addition, if there are external markers, these must be visualized. One way to address these issues is to use a three-dimensional spoiled gradient-echo sequence in the sagittal plane with the following parameters (SPGR, 3 DFT, fat-saturated, TR=60 msec, TE=5 msec, flip angle 40°, 1 excitation (NEX), matrix 256×160 elements, rectangular FOV 16×12 cm, slice thickness 1.3 mm, 128 slices, acquisition time approximately 15 min). Using these parameters, one can obtain complete coverage across the knee joint and the external markers both in mediolateral and anteroposterior direction while achieving good spatial resolution and contrast-to-noise ratios between cartilage, bone and joint fluid (FIGS. 8 and 9). The fat-saturated 3D SPGR sequences can be used for rendering the cartilage in three dimensions (see description below). The 3D SPGR sequence can then be repeated in the sagittal plane without fat saturation using the identical parameters and slice coordinates used during the previous acquisition with fat saturation. The resultant non-fat-saturated 3D SPGR images demonstrate good contrast between low signal intensity cortical bone and high signal intensity bone marrow thereby facilitating 3D rendering of the femoral and tibial bone contours. It is to be understood that this approach is representative only and should not be viewed as limiting in any way.

Volumes of Interest (VOI)

The invention allows a health practitioner to determine cartilage loss in a reproducible fashion and thus follow the progression of a cartilage defect over time.

In one embodiment of the invention, one can use a 2D or a 3D surface detection technique to extract the surface of the joint, e.g. the femoral condyles, on both baseline and follow-up scans. For example, a T1-weighted spin-echo sequence can be used for surfaces extraction of the femoral condyles. The T1-weighted spin-echo sequence provides high contrast between low signal intensity cortical bone and high signal intensity fatty marrow. For detection of the surface of the femoral condyles, a step-by-step problem solving procedure, i.e., an algorithm, can convolve a data set with a 3D kernel to locate the maximum gradient location. The maximum gradient location corresponds to the zero crossing of a spatial location. When the kernel is designed properly, then there will be only one zero crossing in the mask. Thus, that zero crossing is the surface. This operation is preferably three-dimensional rather than two-dimensional. The surface of the joint, e.g. the femoral condyles, on the baseline scan can be registered in an object coordinate system A. The surface of the joint, e.g. the femoral condyles, on the follow-up scan can be registered in an object coordinate system B. Once these surfaces have been defined, a transformation B to B' can be performed that best matches B' with A. Such transformations can, for example, be performed using a Levenberg Marquardt technique. Alternatively, the transformations and matching can be applied to the cartilage only. The same transformation can be applied to the cartilage sensitive images on the follow-up scan in order to match the cartilage surfaces.

Using the 3D surface registration of the joint on the baseline scan and resultant object coordinate system A, one can place volumes of interest over the area of a cartilage defect seen on the cartilage sensitive images. For example, in the knee joint, the size of the targeted volumes of interest can be selected to exceed that of the cartilage defect in anteroposterior and mediolateral direction, e.g. by 0.5 to 1 cm. If the defect is located high on the femoral condyle or in the trochlear region, the targeted VOI can be chosen so that its size exceeds that of the cartilage defect in superoinferior and mediolateral direction. The third dimension of the targeted VOI (parallel to the surface normal of the cartilage) can be fixed, for example at 1 cm. VOI size and placement can be manual or automatic on the baseline study. Once the targeted VOI has been placed on the image using visual or automated computer control, the 3D coordinates of the targeted VOI relative to the 3D contour of the joint and object coordinate system A can be registered and saved. On follow-up studies, e.g. scans inadvertently obtained with slightly different patient position, the 3D surface of the joint is registered to match the orientation of the baseline scan and the targeted VOI is then automatically placed on the joint using object coordinate system B' and the coordinates saved on the baseline study. Cartilage volume within the targeted VOI on baseline and follow-up studies can, for example, be determined using standard thresholding and seed growing techniques.

Reference Markers

When obtaining the MR images for use in this invention, whether the MRI is of cartilage or of bone, external reference markers can be placed on the skin around the joint of the subject being imaged. The external marker can be designed not only to show up in the MRI, but also to show up if an external image of the joint is obtained. The importance and value of such unique reference markers will be discussed in more detail hereinafter.

Thus, one embodiment of the invention is a skin reference marker that can be used in the assessment of the condition of a joint of a human. Multiple skin reference markers can be placed upon one or more limbs of a patient prior to internal imaging and external imaging. Each skin reference marker comprises a material detectable by an imaging technique, a container for the material in which the container preferably has multiple surfaces, a means for affixing the container to the skin (e.g. an adhesive placed on at least one surface of the container in an amount sufficient to adhere the container to the skin of a human), and a reflective material (preferably retro-reflective) placed on another surface of the container located away from the adhesive. Several imaging techniques can be used that are able to detect the marker. For example, magnetic resonance imaging is preferred, but, ultrasound, or X-ray are also useful. In the case of X-ray, further manipulations must be performed in which multiple X-ray images are assimilated by a computer into a 2 dimensional cross-sectional image called a Computed Tomography (CT) Scan. The material detectable by an imaging can be either in a liquid form or a solid form. The material can be any imaging contrast agent or solution, e.g. a paramagnetic material. The material can be a lanthanide, such as one belonging to the yttrium group of rare earth metals. More specifically, the material can be gadolinium. The shape of the container can be any shape allowing it to be placed on the skin of a human. For example, it can be cubical, spherical, elliptical, discoid or cylindrical. The size of the container can be any size, but optimally a size allowing it to be recorded by an imaging machine. The longest dimension of the container can be up to 5.0 cm, but preferably is about 0.25 to 2.0 cm. The reflective or retro-reflective material can be any material that is able to reflect light directly back to the source of the light so that the position of the reference marker is captured by the optoelectrical recording means, e.g. a video camera. 3M Corporation makes several retro-reflective materials.

Manipulating Images

Once a magnetic resonance image is obtained, it can be manipulated to improve the image by reducing unwanted, non-cartilage images.

Segmentation

To prepare the data set for 3D rendering, the cartilage can be segmented image by image using a signal-intensity-based threshold combined with a seed growing technique. The femoral, tibial, and patellar cartilage can be segmented separately based on the fat-saturated 3D SPGR or 3D DEFT sequence. Manual disarticulation can be performed by outlining the cartilage contour in areas where the signal intensity of the articular cartilage is similar to that of adjacent structures. The contours of the femoral, tibial, and patellar bone can be segmented separately using the non-fat-saturated 3D SPGR or 3D DEFT sequence. Segmentation software can allow for manual editing of cartilage thickness maps and cartilage defects detected using the above embodiments. In this fashion, the operator can correct erroneous detection of cartilage defects in areas where the cartilage may be naturally thinner. Such software includes seed-growing algorithms and active-contour algorithms that are run on standard PC's. A sharp interface is present between the high signal intensity bone marrow and the low signal intensity cortical bone thereby facilitating seed growing. Fat-saturated and non-fat-saturated 3D sequences can be acquired with the same field of view, slice thickness and slice positions, thereby enabling superimposition and cross registration of any resultant 3D renderings of the femoral, tibial, and patellar cartilage and bone. External reference markers can aid in registering the 3D data in the same object coordinate system.

3D maps of cartilage thickness can be generated using several different techniques. One representative, but not limiting, approach uses a 3D surface detection technique which is based on a 2D edge detector (Wang-Binford) that has been extended to 3D. This surface detection technique can generate surface points and their corresponding surface normal. To smooth the contour, the program samples 25 percent of the surface points and fits a cubic spline to the sample points. The program can compute the curvature along sample spline points and find two sample points that have the maximum curvature and are separated by about half the number of voxels on the contour. These points partition the spline into two subcontours. For each subcontour, the program can compute the average distance between the points and the center of the mass. The program can designate the subcontour with the smaller average distance as the inner cartilage surface and the other subcontour as the outer cartilage surface (OCS). The intersect between the inner cartilage surface (ICS) (located at the subchondral bone interface) and the outer cartilage surface with the surface normal can be used to compute the 3D thickness of the articular cartilage on a pixel-by-pixel basis.

Creating a Three Dimensional (3D) Image of the Cartilage

Three Dimensional Geometric Model Generation

After the 3D image of cartilage and the 3D image of joint with bones (as discussed hereinafter), are obtained, for example, the set of segmented two dimensional MR images can be transformed to a voxel representation using a computer program developed in the AVS Express (Advanced Visual Systems, Inc., Waltham, Mass.). Every voxel has a value of zero if it is not within an object of interest or a value ranging from one to 4095, depending on the signal intensity as recorded by the MRI machine. An isosurface can then be calculated that corresponds to the boundary elements of the volume of interest. A tesselation of this isosurface can be calculated, along with the outward pointing normal of each polygon of the tesselation. These polygons are written to a file in a standard graphics format (Virtual Reality Modeling Language Version 1.0: VRML output language).

Visualization Software

One possible choice for the software program used to assess the cartilage degeneration pattern, the bones of the joint, and the motion pattern of the patient is a user controllable 3D visual analysis tool. The program can read in a scene, which scene consists of the various 3D geometric representations or "actors" (for example, VRML files of the tibia, tibia cartilage, femur, femoral cartilage), the static relationship transformations between these actors, and, if available, sequence of transformations describing how these actors move with respect to each other as the patient performs some activity, such as walking, jogging, etc.

The program can allow the user, through the use of the mouse and/or keyboard, the ability to observe the scene from arbitrary angles; to start and stop the animation derived from the motion profiles and to observe the contact line and any cartilage lesions while the animation is running. Additionally, the user can derive quantitative information on the scene through selecting points with the mouse.

The software program can be written in the CTT computer language and can be compiled to run on both Silicon Graphics Workstations and Windows/Intel personal computers.

Cartilage Thickness Maps

Cartilage thickness can be determined by several methods. One example is detecting the locations of the bone-cartilage and the cartilage-joint fluid interface along the surface normal using the same edge detector described below, and subtracting them. This procedure can be repeated for each pixel located along the bone-cartilage interface. The x, y, and z position of each pixel located along the bone-cartilage interface can be registered on a 3D map or multiple 2D maps and thickness values are translated into color values. In this fashion, the anatomic location of each pixel at the bone cartilage interface can be displayed simultaneously with the thickness of the cartilage in this location.

The edge detector can produce accurate surface points and their corresponding surface normal. The detector can be applied to the baseline and the follow-up data set. For the baseline data set, both the surface points and surface normals can be used to form locally supporting planes (for each voxel). These planes can form an approximated surface for the baseline skeletal site. As for the follow-up data set, the surface points can be matched in the registration procedure onto the surface of the baseline data set. One can use a newly developed 3D surface detection technique to extract the surface of the skeletal site on both the baseline scan and the follow-up scan. Once these surfaces are detected, one can use the Levenberg Marquardt procedure to find the transformation that best matches these two surfaces.

A possible approach for calculating the cartilage thickness is based on a 3D Euclidian distance transformation (EDT). After thresholding, the voxels on the edge of the cartilage structure can be extracted using a slice by slice 8-neighbor search, resulting in a binary volume with the voxels on the cartilage surface having a value of 1 and all others being 0. To classify these surface points as part of the ICS or OCS, a semi-automatic approach, which requires the user to enter a point that lies outside the cartilage structure and faces the ICS, can be useful. From this point, rays are cast in all directions of the volume using a modified Bresenham's line drawing algorithm. If a ray hits a voxel with a value of 1, this point is classified as part of the ICS: After a complete sweep of the volume, for initialization of the EDT the ICS voxels are given a value of 0, whereas all other voxels are set to 1.

For computation of the EDT, the following representative algorithm can be useful. It can decompose the calculation into a series of 3 one-dimensional transformations and can use the square of the actual distances, which accelerates the process by avoiding the determination of square roots.

First, for a binary input picture $F=\{f_{ijk}\}$ ($1 \leq i \leq L$, $1 \leq j \leq M$, $1 \leq k \leq N$) a new picture $G=\{g_{ijk}\}$ can be derived using equations (3-5) ($\alpha$, $\beta$, and $\gamma$ denote the voxel dimensions). Here F is a set of all voxels initially and G is a set of all voxels at the later time.

$$g_{ijk} = {}_x\min\{(\alpha(i-x))^2; f_{xjk}=0; 1 \leq x \leq L\} \quad \text{[Eq. 3]}$$

Thus, each point can be assigned the square of the distance to the closest feature point in the same row in i-direction. Second, G can be converted into $H=\{h_{ijk}\}$ using equation (4).

$$h_{ijk} = {}_y\min\{g_{iyk}+(\beta(j-y))^2; 1 \leq y \leq M\} \quad \text{[Eq. 4]}$$

The algorithm can search each column in the j-direction. According to the Pythagorean theorem, the sum of the square distance between a point (i, j, k) and a point (i, y, k) in the same column, $(\beta(j-y))^2$, and the square distance between (i, y, k) and a particular feature point, $g_{iyk}$, equals the square distance between the point (i, j, k) and that feature point. The minimum of these sums is the square distance between (i, j, k) and the closest feature point in the two-dimensional i-j-plane.

The third dimension can be added by equation (5), which is the same transformation as described in the equation for the k-direction (4).

$$s_{ijk} = {}_z\min\{h_{ijz}+(\gamma(k-z))^2; 1 \leq z \leq N\} \quad \text{[Eq. 5]}$$

After completion of the EDT, the thickness of the cartilage for a given point (a, b, c) on the OCS equals the square root of $s_{abc}$. The x, y, and z position of each pixel located along the bone-cartilage interface can be registered on a 3D map and thickness values are translated into color values. In this fashion, the anatomic location of each pixel at the bone cartilage interface can be displayed simultaneous with the thickness of the cartilage in this location.

Displaying the Degeneration Pattern

In an approach the cartilage thickness maps obtained using the algorithm described above display only a visual assessment of cartilage thickness along the articular surface. In another approach, in order to derive a true quantitative assessment of the location, size, and depth of a focal cartilage defect, one can use an iterative approach comparing cartilage thickness of neighboring pixels located along the bone cartilage interface.

For example, assuming an image resolution of 0.5×0.5×1.0 mm and an average thickness of the articular cartilage in the femoral condyles ranging between 2 to 3 mm, a 25% decrement in cartilage thickness will be the smallest change that can be observed with most current imaging sequences. Therefore, for example, pixels along the bone—cartilage interface that demonstrate a decrease exceeding the smallest change observable on a given MRI pulse sequence, in this example 25% or greater, in overlying cartilage thickness when compared to cartilage thickness at the neighboring bone—cartilage interface pixels, can be used to define the margins of a focal cartilage defect. Other criteria can be employed to define a cartilage defect based on comparisons of neighboring pixels. For example, a fixed value can be used. If the difference in cartilage thickness between neighboring pixels exceeds the fixed value, e.g. 1 mm, the pixel where this difference is observed can be used to define the margin of the cartilage defect. This comparison can be performed for each pixel located along the bone—cartilage interface for the entire data set. This comparison is preferably performed in three dimensions. Pixels that demonstrate a decrease in cartilage thickness exceeding defined criteria but that are completely surrounded by other pixels fulfilling the same criteria may not be considered to be part of the margin of the cartilage defect, but will typically be considered to lie inside the cartilage defect.

The invention provides for means for calculating the area covered by the cartilage defect $A_{cartilage\ defect}$ and the mean thickness of the cartilage in the region of the defect $D_{cartilage\ defect}$ as well as the mean thickness of a defined area of surrounding normal cartilage. The thickness of the cartilage previously lost in the defect can be estimated then as:

$$D_{cartilage\ loss} = D_{normal\ cartilage} - D_{cartilage\ defect} \quad \text{[Eq. 6]}$$

Since the area A of the cartilage defect is known, the volume of cartilage loss can be computed as:

$$V_{cartilage\ loss} = A_{cartilage\ defect} \times D_{cartilage\ loss} \quad \text{[Eq. 7]}$$

Thus, the invention provides for means of estimating the thickness, area or volume of cartilage tissue that has been lost.

Figure 24A:
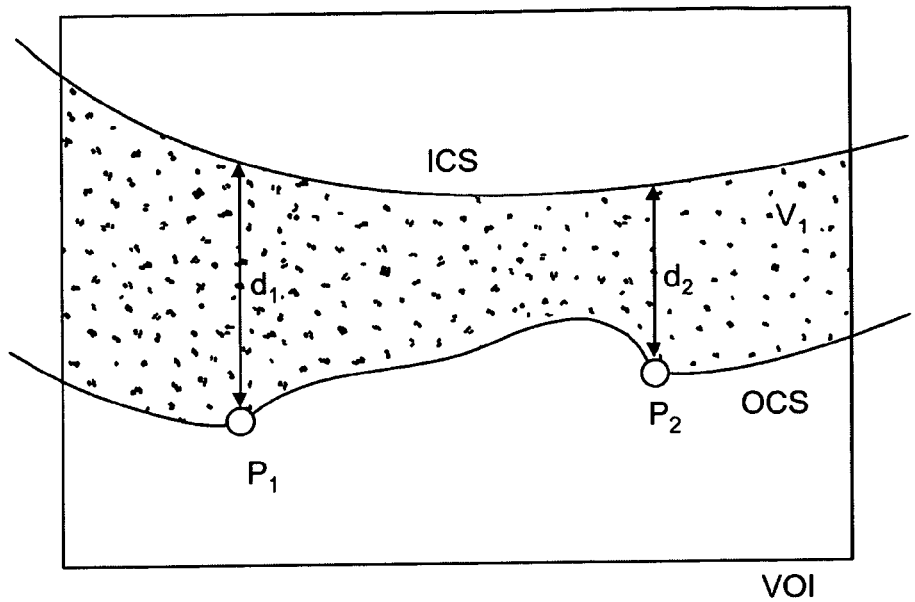
FIGS. 24A-C show interpolation of the outer cartilage (OCS) surface across a cartilage defect using the inner cartilage surface (ICS) as a template.
Figure 24B:
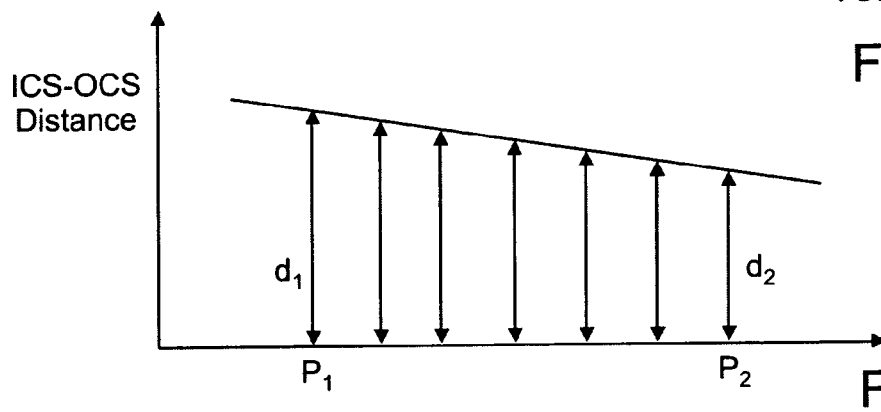
Figure 24C:
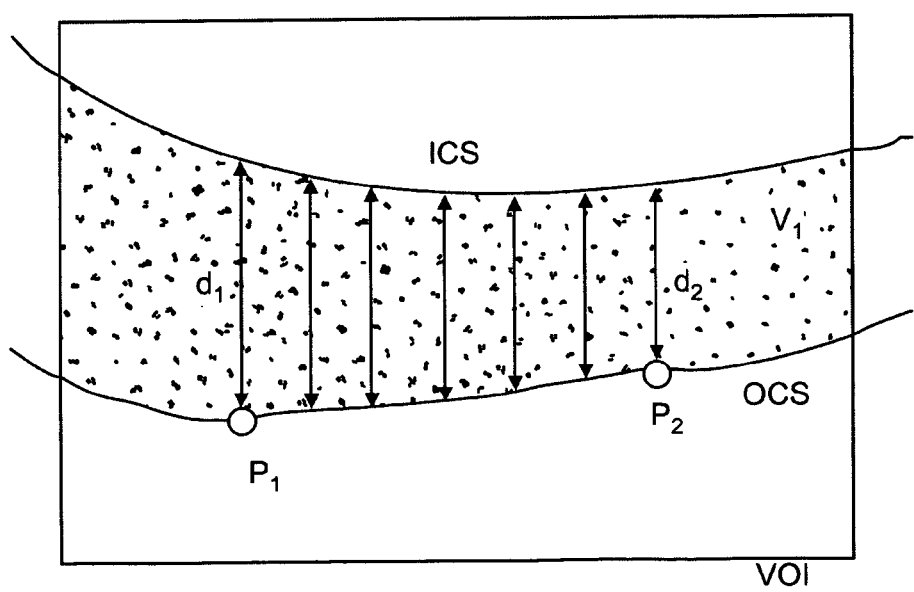

In another embodiment, the cartilage is segmented slice by slice from MR images. This can be achieved, for example, using the live wire method or snakes. After segmentation, a volume of interest (VOI) containing a single cartilage defect can be selected. The cartilage volume $V_1$ within this VOI can be determined. In each slice that contains the defect, two points $P_1$ and $P_2$ on the outer cartilage surface (OCS) can be selected on either side of the defect (FIG. 24, A). The OCS contour of the cartilage defect between $P_1$ and $P_2$ can be erased and interpolated using the inner cartilage surface (ICS) as a guiding line. For this purpose, the distances $d_1$ and $d_2$ between the OCS at $P_1$ and $P_2$ and the ICS can be measured. For OCS reconstruction the OCS-ICS distance can be determined by linear interpolation between $d_1$ and $d_2$ (FIG. 24, B). The interpolated distance values can be used to determine a set of interpolated surface points for the reconstructed OCS (FIG. 24, C). The surface contour between $P_1$ and $P_2$ can be determined with a spline curve that interpolates this set of OCS points. Subsequently, the cartilage volume $V_2$ can be measured, using the same VOI as for VI. The difference $V_2-V_1$ between the two volumes can yield the volume of the cartilage defect.

The depth of the cartilage defect can, for example, be determined as follows: for all points on the interpolated OCS in all the slices containing the defect contour the distance to the closest point of the original OCS can be measured by means of a 3-dimensional Euclidean distance transform. The longest distance value resulting from this computation is typically the depth of the cartilage defect.

The area of the cartilage defect can, for example, be determined as follows: for all the slices that contain the defect, the length of the interpolated OCS can be computed. The sum of these length values, multiplied by the slice thickness, can yield an estimation of the total area of the interpolated OCS contour and thus the area of the cartilage defect.

In another embodiment, the invention provides for means to directly compare the volume, depth, and area of an articular cartilage defect between different MR examinations without having to register the data sets. Thus, the invention can be used to monitor the progression of osteoarthritis. As an additional example of how this technique can be applied, the invention can be used to monitor the effect of disease therapy. In another embodiment, the invention can be used to collect epidemiological data on the volume, depth, and area of articular cartilage defects in different locations of the femur, tibia, and patella.

The invention provides means to accurately measure the volume, depth, and area of a cartilage defect. Furthermore, the comparison between the values for different MR examinations can be performed without registration of the data sets.

Figure 22A:
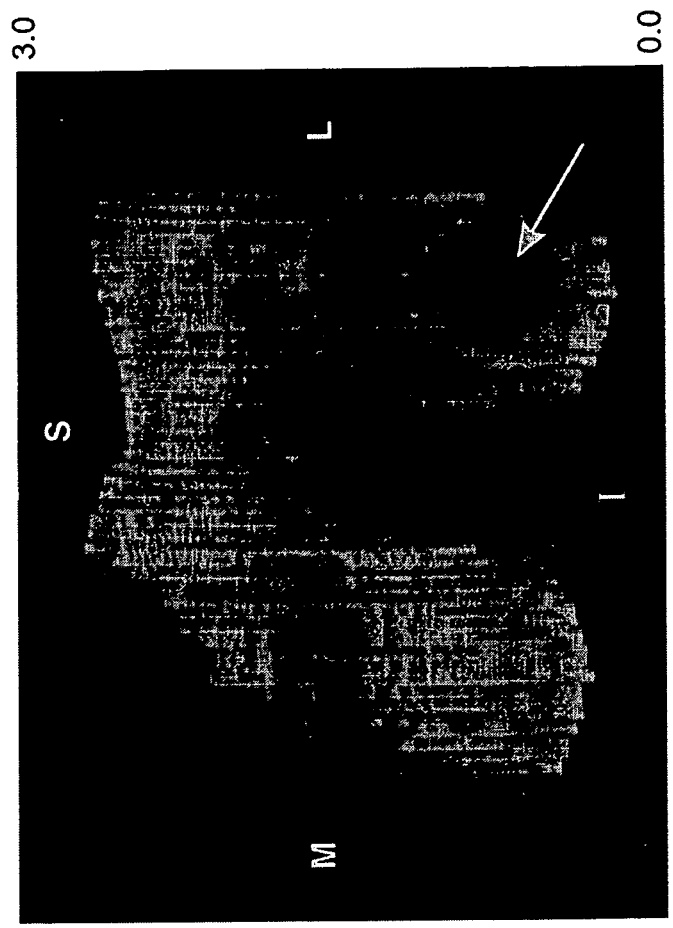
FIGS. 22A and 22B show a 2D MRI (3D SPGR) and 3D cartilage thickness map.
Figure 22B:
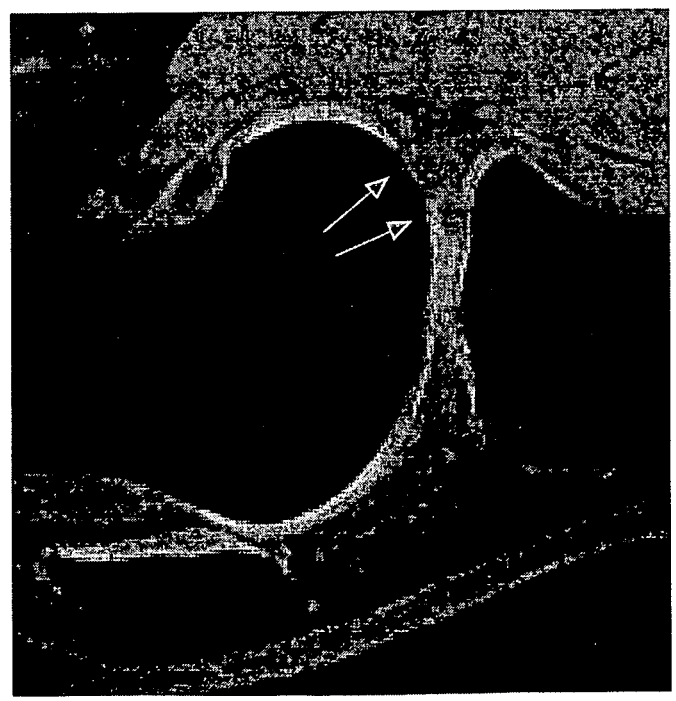
Figure 23E:
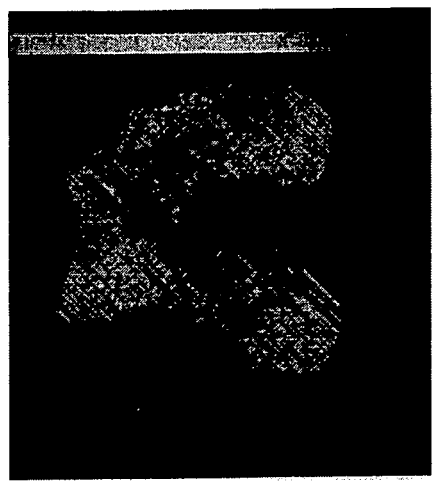
FIGS. 23A-E show the matching of 3D thickness maps generated from MR images obtained with a knee neutral position and external rotation.
Figure 23B:
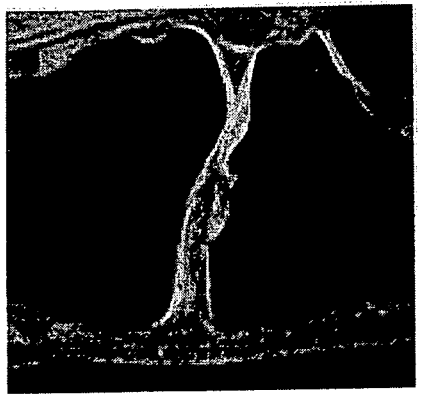
Figure 23D:
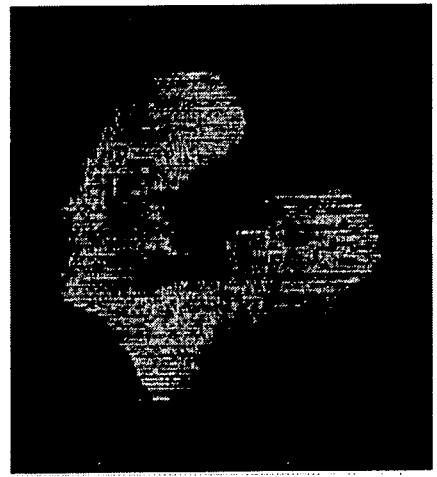
Figure 23A:
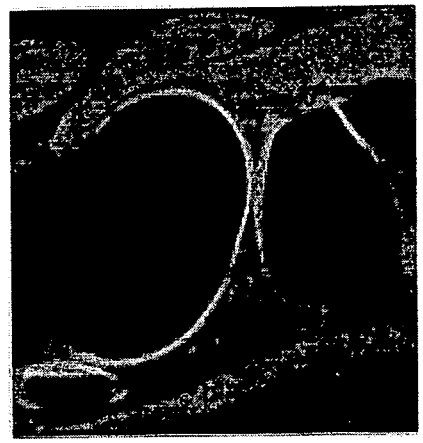
Figure 23C:
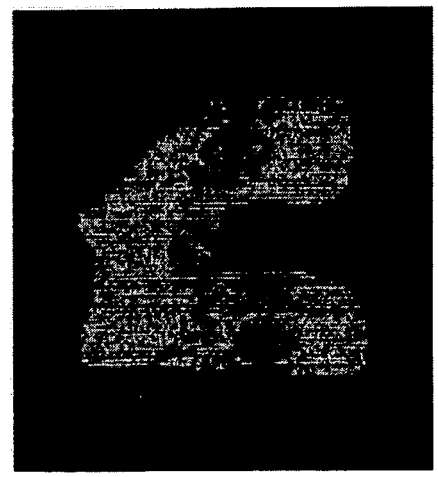

Turning now to FIGS. 22A and 22B, one can see a 2D MRI (3D SPGR) and 3D cartilage thickness map. In A, the 2D MRI demonstrates a full thickness cartilage defect in the posterior lateral femorl condyle (arrows). FIG. 22B shows a 3D cartilage thickness map generated using a 3D Euclidian distance transformation. The thickness of the articular cartilage is color encoded and displayed on a pixel-by-pixel basis along the 3D surface of the articular cartilage. The cartilage defect is black reflecting a thickness of zero (arrows) (M: medial, L: lateral, S: superior, I: inferior).

In FIGS. 23A-23E, one can see the matching of 3D thickness maps generated from MR images obtained with the knee in neutral position and in external rotation. A. Sagittal baseline MR image (3D SPGR) with the knee in neutral position. B. Sagittal follow-up MR image of the same volunteer obtained two weeks later with the knee in 40 degree external rotation (note the artificially widened appearance of the femur resulting from the rotation). C. 3D thickness map generated based on baseline MRI in neutral position. D. 3D thickness map generated based on follow-up MRI in external rotation (note segmentation error between condyles in trochlear region). E. Transformation of D into the object coordinate system of C. Despite extreme differences in joint orientation between baseline and follow-up MRI scans and despite segmentation errors, the thickness distribution on the matched follow-up scan demonstrates great similarity with that seen on the baseline scan in neutral position (in C).

Having now described how to obtain an image of a cartilage of a joint, both with and without external reference markers; how to enhance the image by manipulating non-cartilage images, and creating and displaying 3-D images of the cartilage, ie. a 3-D map, certain aspects of the invention are apparent.

One aspect is a method of estimating the loss of cartilage in a joint. The method comprises
  (a) obtaining a three-dimensional map of the cartilage at an initial time and calculating the thickness or regional volume of a region thought to contain degenerated cartilage so mapped at the initial time,
  (b) obtaining a three-dimensional map of the cartilage at a later time, and calculating the thickness or regional volume of the region thought to contain degenerated cartilage so mapped at the later time, and
  (c) determining the loss in thickness or regional volume of the cartilage between the later and initial times.

Preferably, this aspect of the invention is directed to a volume of interest in the cartilage, i.e., a region of the cartilage that includes a cartilage defect. Such a defect may be the result of a disease of the cartilage (e.g., osteoarthritis) or the result of degeneration due to overuse or age. This invention allows a health practitioner to evaluate and treat such defects. The volume of interest may include only the region of cartilage that has the defect, but preferably will also include contiguous parts of the cartilage surrounding the cartilage defect.

Another aspect of the invention is a method for assessing the condition of cartilage in a joint of a human, which method comprises
  (a) electronically transferring an electronically-generated image of a cartilage of the joint from a transferring device to a receiving device located distant from the transferring device;
  (b) receiving the transferred image at the distant location;
  (c) converting the transferred image to a degeneration pattern of the cartilage; and
  (d) transmitting the degeneration pattern to a site for analysis.

Another aspect of the invention is a method for determining the volume of cartilage loss in a region of a cartilage defect of a cartilage in joint of a mammal. The method comprises (a) determining the thickness, DN, of the normal cartilage near the cartilage defect; (b) obtaining the thickness of the cartilage defect, DD, of the region; (c) subtracting DD from DN to give the thickness of the cartilage loss, DL; and (d) multiplying the DL value times the area of the cartilage defect, AD, to give the volume of cartilage loss. The method is useful for situations wherein the region of cartilage defect is limited to the defective cartilage and preferably wherein the region of the cartilage defect includes a portion of the cartilage contiguous to the defect. Alternatively, for step (a) the normal thickness of the defect area could be estimated. It may be estimated from measurements of cartilage of other subjects having similar characteristics such as gender, age, body type, height, weight, and other factors. It may be estimated from measurements of a similar "normal" cartilage from another corresponding joint (e.g., if the right knee has the defect, measure the normal left knee). It may have been measured at an initial time $T_1$ when the cartilage was normal to provide a baseline. Other means of determining the normal thickness may be available to one of skill in the art. Once the thickness $D_N$ is obtained and the thickness $D_D$ is obtained the two are subtracted to give the $D_L$. The $D_L$ is multiplied by the area of the defect $A_D$ to give the volume of cartilage loss. By determining the volume of cartilage loss at an initial $T_1$ and again at a later time $T_2$, one can determine the change in volume loss over time.

Still another aspect of the invention is a method of estimating the change of a region of cartilage in a joint of a mammal over time. The method comprises (a) estimating the thickness or width or area or volume of a region of cartilage at an initial time $T_1$, (b) estimating the thickness or width or area or volume of the region of cartilage at a later time $T_2$, and (c) determining the change in the thickness or width or area or volume of the region of cartilage between the initial and the later times. The method is particularly useful for regions of degenerated cartilage or diseased cartilage.

Still another aspect of the invention is a method of estimating the loss of cartilage in a joint. The method comprises (a) defining a 3D object coordinate system of the joint at an initial time, $T_1$; (b) identifying a region of a cartilage defect within the 3D object coordinate system; (c) defining a volume of interest around the region of the cartilage defect whereby the volume of interest is larger than the region of cartilage defect, but does not encompass the entire articular cartilage; (d) defining the 3D object coordinate system of the joint at a second timepoint, $T_2$; (e) placing the identically-sized volume of interest into the 3D object coordinate system at timepoint $T_2$ using the object coordinates of the volume of interest at timepoint $T_1$; (f) and measuring any differences in cartilage volume within the volume of interest between timepoints $T_1$ and $T_2$.

Therapeutic Planning, Devising New Therapies

In another embodiment of the invention, thickness of the articular cartilage can be estimated using an imaging test. This imaging test can be an x-ray, ultrasound, CT scan or MRI scan. Thickness can be determined using a 3D Euclidian distance transformation as well as other techniques feasible for this purpose. Thickness can be determined in selected regions or across the entire cartilage of a joint. Thickness can be determined in areas adjacent to diseased cartilage, in areas of diseased cartilage and in areas of normal cartilage.

Furthermore, the curvature of the cartilage can be determined. For this purpose, the curvature of the inner cartilage surface, i.e. the surface facing the subchondral bone, or the outer cartilage surface, i.e. the surface facing the joint cavity, can be determined. Preferably, the inner cartilage surface at the interface with the subchondral bone will be used, since the outer cartilage surface may be subject to fraying, fissuring or more advanced stages of cartilage loss. Alternatively, the curvature of the subchondral bone can be determined. In this case, the curvature of the subchondral bone can serve as an approximation of the curvature of the articular cartilage. Curvature can be determined from an imaging test, typically an ultrasound, a CT or an MRI scan. Curvature can be determined from a three-dimensional model of the cartilage. The three-dimensional model of the cartilage can be determined using the 3D Euclidian distance transformation mentioned above. Curvature can be determined in selected regions or across the entire cartilage of a joint. Curvature can be determined in areas adjacent to diseased cartilage, in areas of diseased cartilage and in areas of normal cartilage.

Using information on thickness and curvature of the cartilage, a physical model of the surfaces of the articular cartilage and of the underlying bone can be created. This physical model can be representative of a limited area within the joint or it can encompass the entire joint. For example, in the knee joint, the physical model can encompass only the medial or lateral femoral condyle, both femoral condyles and the notch region, the medial tibial plateau, the lateral tibial plateau, the entire tibial plateau, the medial patella, the lateral patella, the entire patella or the entire joint.

In another embodiment, the location of a diseased area of cartilage can be determined, for example using a 3D coordinate system or a 3D Euclidian distance transformation in combination with some of the techniques outlined above. In another embodiment of the invention, the anteroposterior, mediolateral or superoinferior dimension of an area or multiple areas of diseased cartilage can be determined. Furthermore, the area, depth and volume of a cartilage defect can be determined, for example using a 3D Euclidian distance transformation in combination with some of the techniques outlined above In one embodiment of the invention, information on thickness of the cartilage, information on curvature of the cartilage, information on curvature of the subchondral bone or information on the location, dimensions, area, depth and volume of a defect or combinations thereof can be used to devise a treatment. For example, the dimensions of a defect determined in this manner can be used to determine the dimensions of a cartilage transplant, a cartilage graft, a cartilage implant, a cartilage replacement material, a cartilage scaffold or a cartilage regenerating material or any cartilage repair system. Additionally, the curvature of the inner cartilage surface or the subchondral bone can be measured and this information can be used to determine the shape of a cartilage transplant, a cartilage graft, a cartilage implant, a cartilage replacement material, a cartilage scaffold or a cartilage regenerating material or any cartilage repair system. Additionally, the thickness of normal cartilage adjacent to the defect can be measured and the thickness values measured in this fashion can be used to determine the optimal thickness for a cartilage transplant, a cartilage graft, a cartilage implant, a cartilage replacement material, a cartilage scaffold or a cartilage regenerating material or any cartilage repair system. Alternatively, the thickness of the cartilage can be measured in the contralateral joint, e.g. the knee joint, in an area corresponding to the area of diseased cartilage in the affected joint. Using any of these techniques or, preferably, a combination thereof, an optimal fit can be achieved between the surrounding normal cartilage and a cartilage transplant, a cartilage graft, a cartilage implant, a cartilage replacement material, a cartilage scaffold or a cartilage regenerating material or any cartilage repair system thereby minimizing incongruity at the joint surface and improving the therapeutic result.

The invention provides for means to create a cast or a mold for shaping a cartilage transplant, a cartilage graft, a cartilage implant, a cartilage replacement material, a cartilage scaffold or a cartilage regenerating material or any cartilage repair system. This can be generated using computer devices and automation, e.g. computer assisted design (CAD) and, for example, computer assisted modeling (CAM).

In another embodiment, the invention provides for means to measure and visualize the curvature of the surfaces of cartilage and bone. In another embodiment, the invention provides for means to compare the thickness and the curvatures of surfaces of a cartilage transplant and a transplantation site, a cartilage graft and a graft site, a cartilage implant and an implantation site, a cartilage replacement material and an implantation site, a cartilage scaffold and a cartilage defect, a cartilage regenerating material and an area of diseased cartilage, or a cartilage repair system and an area of diseased cartilage.

The invention is useful for determining the shape, dimensions and thickness of a cartilage transplant, a cartilage graft, a cartilage implant, a cartilage replacement material, a cartilage scaffold or a cartilage regenerating material or any cartilage repair system prior to treatment. For example, the shape, dimensions and thickness of a cartilage transplant, a cartilage graft, a cartilage implant, a cartilage replacement material, a cartilage scaffold or a cartilage regenerating material or any cartilage repair system can be designed to follow the physical shape and thickness of the cartilage adjacent to an area of diseased cartilage determined using the imaging test.

The invention is applicable to a host of current and future treatments of arthritis including but not limited to cartilage transplants, cartilage implants, cartilage grafts, cartilage replacement materials, cartilage scaffolds, cartilage regenerating materials, auto-, allo- and xeno-transplants, osteochondral allo- and autografting, stem cell based repair systems and transfer systems, and, principally, any other current and future treatments and devices for cartilage repair or regeneration.

The example described below shows one possibility how aspects of the invention can be implemented. It demonstrates one possible way how the invention can be practiced. It is in no way meant to limit the invention. One skilled in the art will easily recognize other means of practicing the invention.

In a first step, the cartilage and bone contours can be segmented from the MR images using for example a modified live wire technique [Steines D, Cheng C, Wong A, Berger F, Napel S, Lang P. CARS—Computer-Assisted Radiology and Surgery, p. 578-583, San Francisco, 2000].

From the segmented data, a 3-dimensional surface representation can be created, which yields a triangular tesselation of the surface. For this calculation, a 3-dimensional Wang-Binford edge detector [Yan C H: *Measuring changes in local volumetric bone density: new approaches to quantitative computed tomography*, Ph.D. thesis, 1998, Dept. of Electrical Engineering, Stanford University] or the marching cubes algorithm [Lorensen W E, Cline H E. Comput Graph 1987; 21: 163-169] can be used. This surface representation can be imported into a CAD system, which is used to generate a physical model or a cast by means of rapid prototyping techniques.

The segmented data can also be used for measuring the surface curvature at the surface points. The curvature is calculated according to formula xx. If $\alpha:(a,b) \rightarrow \mathbb{R}^2$ is a curve defined over the parameter interval (a,b) by $\alpha(t)=(x(t),y(t))$, then the curvature K is given by [Gray A: *Modern Differential Geometry of Curves and Surfaces.* 1993; CRC Press]:

$$\kappa(t)=[x'(t)y''(t)-x''(t)y'(t)]/[(x'^2(t)+y'^2(t))^{3/2}] \quad [\text{Eq. 8}]$$

For the digitized contours that result from the segmentation, smooth derivatives for equation (8) can be obtained by convolution with differentiated Gaussian kernels [Worring M, Smeulders A W M. CVGIP: Image Understanding, 1993. 58(3): p. 366-382].

The curvature values can be calculated for each pixel on the segmented surface in each slice. They can subsequently be color-mapped onto a 3-dimensional rendering of the surface for visualization purposes.

For full curvature information this procedure can be repeated for a direction perpendicular to the imaging plane. Of the remaining two main directions the one with the lower degree of parallelism to the surface can be chosen, and reformatted slices of the MR data set can be obtained for this direction. For instance, when curvature values for the femoral condyles are calculated from sagittal MR images of the knee, the data set would typically be reformatted for a coronal slicing plane.

The procedure of segmentation and curvature calculation can then be repeated for the reformatted images. A second curvature map can be calculated, yielding complementary information to the first one.

In order to compare curvature values for different surface patches, these can be manually or automatically registered, overlaying one surface patch on top of the other. Corresponding curvature values that are calculated in the same directions can now be subtracted from each other, thereby yielding a measure of how well curvatures of two surfaces match.

An example how aspects of the invention can be practiced clinically in a patient is given below. It demonstrates one possible way how the invention can be practiced. It is in no way meant to limit the invention. One skilled in the art will easily recognize other means of practicing the invention.

A patient with arthritis of the knee joint is referred for an MRI scan. The MRI scan is performed using a cartilage sensitive MRI pulse sequence such as a fat saturated spoiled gradient echo sequence or a water selective 3D gradient echo sequence using a spectral spatial pulse. The MR images are transferred via a local network or, for example, the internet into a computer workstation. The computer workstation uses software to extract or segment the articular cartilage from the surrounding tissue. Such software can include snake algorithms, livewire algorithms, signal intensity based thresholding, or seed growing algorithms as well as any other technique useful for this purpose. The software can then generate a three-dimensional map of cartilage thickness across the femoral condyles, the tibial plateau, or the patella. This can be achieved using a 3D Euclidian distance transformation. Additionally, the software can provide information on cartilage curvature or curvature of the subchondral bone as described above. Furthermore, the software can determine the location, dimensions, size, area, depth, or volume of areas of diseased cartilage.

The information generated in this fashion can be used to generate a physical model of the area of diseased cartilage. For example, a bone replacement material can be formed with a CAD/CAM system using the above information. One of the surfaces of the bone replacement material can be shaped so that it matches the 3D curvature of the subchondral bone subjacent to the area of diseased cartilage. Additionally, the anteroposterior, mediolateral or superoinferior dimensions of this surface of the bone replacement material can be such that it matches the dimensions of the area of diseased cartilage. Cartilage cells can be affixed to the bone replacement material and can be grown on the bone replacement material until the thickness of the resultant cartilage matches that of the thickness of the cartilage adjacent to the area of diseased cartilage measured on the 3D cartilage thickness map. Alternatively, a layer of cartilage of known thickness can be applied to the bone replacement material whereby the thickness can be chosen to match the thickness of the cartilage adjacent to the area of diseased cartilage measured on the 3D cartilage thickness map.

Alternatively, an artificial non-human material with properties similar to cartilage can be applied to the bone replacement material whereby the thickness of this material can be chosen to match the thickness of the cartilage adjacent to the area of diseased cartilage measured on the 3D cartilage thickness map.

Alternatively, cartilage can be grown on a mold matching the curvature of the subchondral bone in an area of diseased cartilage whereby the dimensions of the surface of the mold on which the cartilage is grown matches the dimensions of an area of diseased cartilage. Cartilage can then be grown on the mold until its thickness matches the thickness of cartilage adjacent to the area of diseased cartilage as measured, for example, on a 3D cartilage thickness map. At this point, for example, an orthopedic surgeon can excise the area of diseased cartilage and can implant the cartilage or cartilage replacement material. Since the curvature of the cartilage or cartilage replacement material matches that of the underlying subchondral bone and since the thickness of the cartilage or cartilage replacement material matches that of the cartilage adjacent to the area of excised diseased cartilage, normal or near normal joint congruity can be achieved with a resultant decrease in wear on the implanted cartilage or cartilage replacement material and also a decrease in wear on the adjacent cartilage or the cartilage of the opposing joint surface.

Display of Biochemical Information

In addition to providing a 2D or 3D representation of the morphological properties of cartilage, the invention provides for techniques to represent one or more biochemical components of articular cartilage.

A biochemical component includes, but is not limited to, glycosaminoglycan, water, sodium, or hyaluronic acid. Biochemical data can be generated with other magnetic resonance based techniques including the use of signal intensity measurements, relaxation time measurements, paramagnetic and other contrast media and sodium rather than proton MR imaging. Other imaging tests such as positron emission tomography scanning can also be used for this purpose. Thus, one aspect of this invention is a method for providing a biochemically-based map of joint cartilage. The method comprises (a) measuring a detectable biochemical component throughout the cartilage,
(b) determining the relative amounts of the biochemical component throughout the cartilage;
(c) mapping the amounts of the biochemical component through the cartilage; and
(d) determining the areas of cartilage deficit by identifying the areas having an altered amount of the biochemical component present.

Once a map is obtained, it can be used in assessing the condition of a cartilage at an initial time and over a time period. Thus, the biochemical map may be used in the method aspects of the invention in a manner similar to the cartilage thickness map.

For example, one aspect is a method of estimating the loss of cartilage in a joint. The method comprises (a) obtaining a relaxation time or biochemical map of the cartilage at an initial time and analyzing the relaxation time or biochemical content of a region thought to contain degenerated cartilage so mapped at the initial time,
(b) obtaining a relaxation time or biochemical map of the cartilage at a later time, and time analyzing the relaxation time or biochemical content of the region thought to contain degenerated cartilage so mapped at the later time, and
(c) determining the change in relaxation time or biochemical content of the cartilage between the later and initial times.

Preferably, this aspect of the invention is directed to a volume of interest in the cartilage, i.e., a region of the cartilage that includes a cartilage defect. Such a defect may be the result of a disease of the cartilage (e.g., osteoarthritis) or the result of degeneration due to overuse or age. This invention allows a health practitioner to evaluate and treat such defects. The volume of interest may include only the region of cartilage that has the defect, but preferably will also include contiguous parts of the cartilage surrounding the cartilage defect.

As discussed herein before, another aspect of the invention is a method for assessing the condition of cartilage in a joint using a relaxation time or the biochemical map. The method comprises (a) electronically transferring an electronically-generated relaxation time or biochemically based image of a cartilage of the joint from a transferring device to a receiving device located distant from the transferring device;
(b) receiving the transferred image at the distant location;
(c) converting the transferred image to a degeneration pattern of the cartilage; and
(d) transmitting the degeneration pattern to a site for analysis.

Another aspect of the invention is a method for determining the change of biochemical content in a region of a cartilage defect of a cartilage in joint of a mammal. The method comprises (a) determining the biochemical content ($BC_N$) of the normal cartilage near the cartilage defect; (b) obtaining the biochemical content of the cartilage defect (BC D) of the region; and (c) subtracting $BC_D$ from $BC_N$ to give the value of the cartilage change, $BC_D$. The method is useful for situations wherein the region of cartilage defect is limited to the defective cartilage and preferably wherein the region of the cartilage defect includes a portion of the cartilage contiguous to the defect.

Alternatively, for step (a) the normal content of the defect area could be estimated. It may be estimated from measurements of cartilage of other subjects having similar characteristics such as gender, age, body type, height, weight, and other factors. It may be estimated from measurements of a similar "normal" cartilage from another corresponding joint (e.g., if the right knee has the defect, measure the normal left knee). It may have been measured at an initial time $T_1$ when the cartilage was normal to provide a baseline. Other means of determining the normal content may be available to one of skill. in the art. Once $BC_N$ is obtained and $BC_D$ is obtained the two are subtracted to give the Δ. By determining the change of content at an initial $T_1$ and again at a later time $T_2$, one can determine the change in biochemical content over time.

Once a relaxation time or biochemically-based map is provided, morphological maps of articular cartilage obtained with MR imaging can be superimposed, merged or fused with the biochemical map or data. Several different techniques can be applied in order to superimpose, merge, or fuse morphological data with biochemical data. For example, 2D or 3D morphological data of articular cartilage can be acquired with the same object coordinates as the biochemical data. Morphological data and biochemical data can then be easily displayed simultaneously using different colors, opacities, and or gray scales. Alternatively, 2D or 3D morphological data or articular cartilage can be acquired with different object coordinates as the biochemical data. In this case, a 3D surface registration can be applied in order to superimpose, merge, or fuse the morphological data and the biochemical data. As an alternative to 3D object coordinates, anatomic landmarks can be used to register the morphological data and subsequently the biochemical data in a 3D object coordinate system. 3D object coordinate systems can then be matched by matching the landmarks obtained from the morphological data with those obtained from the biochemical data.

Thus, another aspect of this invention is a method for assessing the condition of a subject's cartilage in a joint, the method comprises obtaining a three dimensional biochemical representation of the cartilage, obtaining a morphological representation of the cartilage, and merging the two representations, and simultaneously displaying the merged representations on a medium. The merged representations are then used to assess the condition of a cartilage, estimate the loss of cartilage in a joint, determining the volume of cartilage loss in a region of cartilage defect, or estimating the change of a region of cartilage at a particular point in time or over a period of time. One can see that similar steps would be followed as spelled out for the use of a thickness map or biochemical map.

Simultaneous display of morphological data with biochemical data provides a useful tool to assess longitudinal changes in morphology or articular cartilage and biochemical composition of articular cartilage, for example during treatment with chondroprotective and chondroregenerative agents.

Part of the unique aspect of this technology is that it lends itself to assessment of a patient from a distant position after an image is taken of the joint under evaluation. Thus one aspect of this invention is a method for assessing the condition of cartilage in a joint from a distant location. The method comprises (a) electronically transferring an electronically-generated image of a cartilage of the joint from a transferring device to a receiving device located distant from the transferring device;
(b) receiving the transferred image at the distant location;
(c) converting the transferred image to a degeneration pattern of the cartilage; and
(d) transmitting the degeneration pattern to a site for analysis.

The degeneration pattern includes a measure of cartilage thickness or regional cartilage volume.

The electronically generated image of the cartilage preferably is an MR image and the degeneration pattern can be displayed as a three-dimensional image as a thickness pattern, a biochemical content pattern or a merged thickness biochemical pattern. The electronically generated image is transmitted via Dicom, using the international standards for transmission of such images.

Another aspect of the invention is a kit for aiding in assessing the condition of cartilage in a joint of a mammal, which kit comprises a software program, which that when installed and executed on a computer reads a cartilage degeneration pattern presented in a standard graphics format and produces a computer readout showing a cartilage thickness map of the degenerated cartilage.

The software can be installed in a PC, a Silicon Graphics, Inc. (SGI) computer or a Macintosh computer. Preferably, the software calculates the thickness or regional volume of a region of degeneration of the cartilage which does not include the entire volume of the articular cartilage.

The Movement Pattern

To acquire a movement pattern of a joint in accordance with this invention, one obtains an internal image of the bones in a joint, preferably using MRI techniques, and obtains an external image of the bones in motion. The images are correlated, preferably through the use of external marker sets, to give a pattern that shows a static or moving condition. The correlated images are then displayed and the relation between the movement and degeneration patterns is determined.

Obtaining an Internal Image of Joint with Bones

To obtain an internal image of a joint with the associated bones, one preferably uses MRI techniques that provide an image of the bones on either side of the joint. Here, it is important to use the imaging technique that gives the best image of the bones and how they interact. Because the internal image of the bones can be combined with the image of the bones obtained by external measurements, it is particularly useful, and therefore preferred, to use external reference markers that can be similarly-positioned to the markers used in obtaining the external measurements. The external markers can be placed at any landmarks about the joint of interest. At least three markers are used for each limb being imaged. Preferably the markers will be made of a material that not only will be detected by MRI imaging techniques, but also will be detected by external imaging techniques. The markers will be associated with a means to affix them to the skin and preferably have an adhesive portion for adhering to the skin and a detectable entity that will show up on the MRI image.

The preferred MRI imaging technique useful for obtaining an internal image is a spoiled 3D gradient echo, a water selective 3D gradient echo or a 3D DEFT sequence. A further discussion may be found hereinbefore or in the $2^{nd}$ Edition of Brown and Semelka's book entitled "MRI Basic Principles and Applications."

Once an MRI image is obtained the image is manipulated to enhance the image of the bones. Procedures similar to those discussed hereinbefore for cartilage may be used, but modified for application to bone images.

Creating Three-Dimensional (3D) Image of Joint/Bones

Three-Dimensional Geometric Model Generation

After the 3D image of a joint with bones, the set of segmented two dimensional MR images can be transformed to a voxel representation inside AVS Express (Advanced Visual Systems, Inc., Waltham, Mass.). Every voxel has a value of zero if it is not within an object of interest or a value ranging from one to 4095, depending on the signal intensity as recorded by the 1.5 T MR. An isosurface can then be calculated that corresponds to the boundary elements of the region of interest. A tesselation of this isosurface can be calculated, along with the outward pointing normal of each polygon of the tesselation. These polygons can then be written to a file in a standard graphics format (Virtual Reality Modeling Language Version 1.0).

As discussed hereinbefore, the use of reference markers on the skin around the joint and the bones can provide an image that can later be matched to the reference markers for the cartilage image and the bone images obtained from external measurements.

Alternatively, a semi-automated, 3D surface-based registration technique that does not require the use of an external frame or fiducial markers can be used. This 3D surface-based registration technique can be used to match the anatomic orientation of a skeletal structure on a baseline and a follow-up CT or MRI scan. We extended a robust and accurate 2D edge detector (Wang-Binford) to 3D. This detector is described hereinbefore.

Figure 10C:
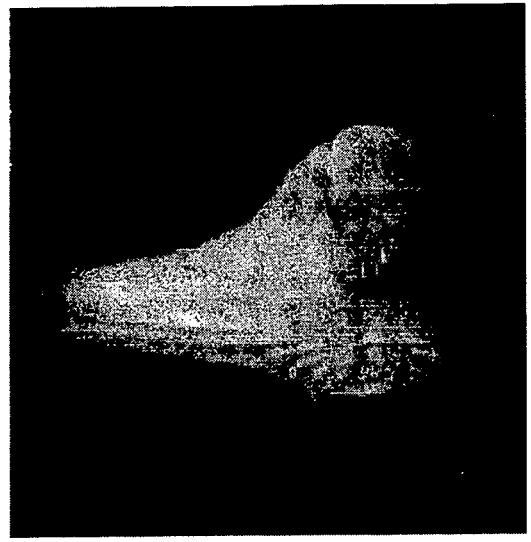
FIGS. 10A-10C show a 3D surface registration of femoral condyles based on T1-weighted spin-echo MR images.
Figure 10B:
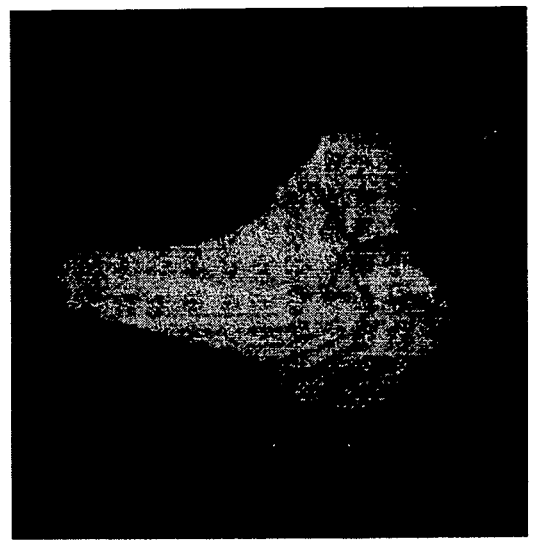
Figure 10A:
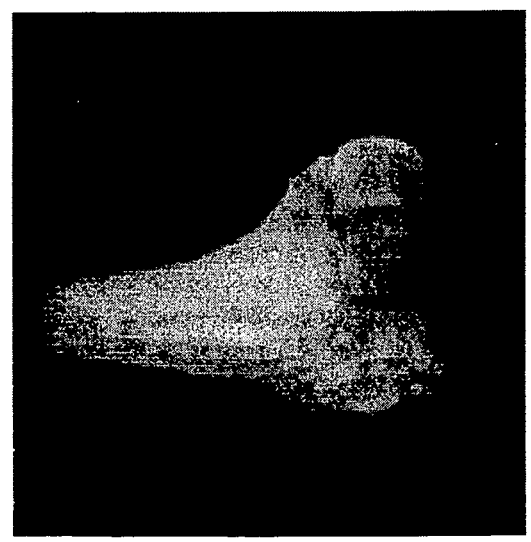

A registration technique for the femoral condyles and the tibial plateau is shown in FIG. 10. It shows an example where 3D surfaces of the femoral condyles were extracted from two differently oriented T1-weighted spin-echo MRI scans (baseline A and follow-up B, respectively) obtained in the same patient in neutral position (A) and in 40 degree external rotation (B). The 3D surfaces were used to derive a coordinate transformation relating the two scans. FIG. 10C demonstrates the use of the derived transformation to re-register scan B in the object coordinate system of scan A. Such a transformation relating two T1-weighted scans can then be used to register DEFT cartilage-sensitive scans that are acquired in the same respective orientations as the A and B T1-weighted scans.

We performed the registration using a Sun Sparc 20 workstation with 128 MBytes of memory. The surface detection algorithm extracted approximately 12,000 surface patches from each data set. The surface extraction and registration routines took about 1 hour in total.

Figure 11A:
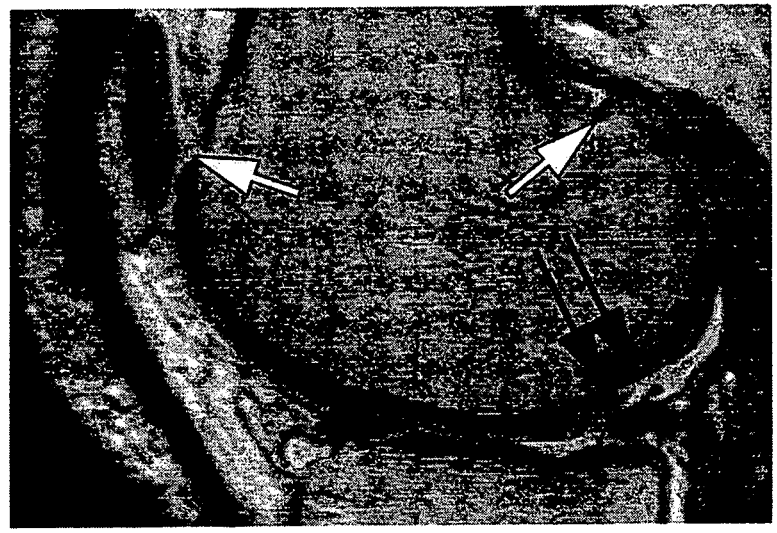
FIG. 11A shows a 2D cartilage thickness map where a proton density fast spin-echo MR image demonstrates a focal cartilage defect in the posterior lateral fermoral condyle (black arrows). White arrows indicate endpoints of the thickness map.
Figure 11B:
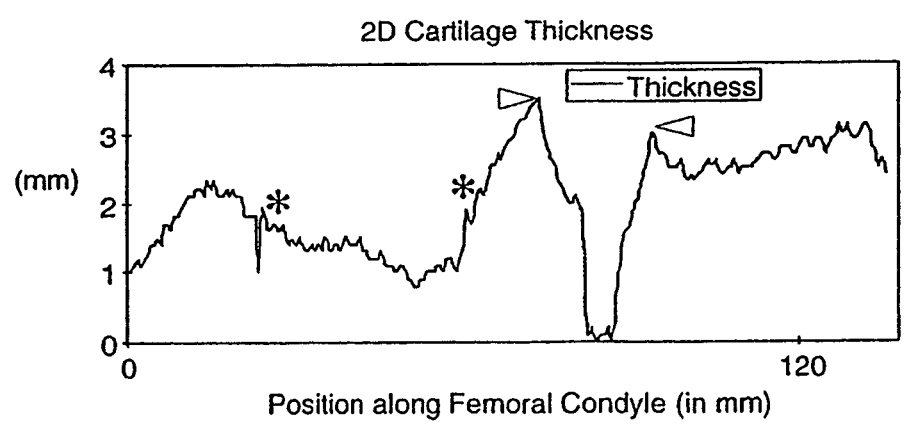
FIG. 11B is a 2D cartilage thickness map demonstrating abrupt decrease in cartilage thickness in the area of the defect (arrows). The A thickness between the neighboring pixels can be use to define the borders of the cartilage defect. Note defused cartilage thinning in the area enclosed by the asterisks(*).

Since the algorithm for 3D surface registration of the femoral condyles also computes the surface normals for the medial and lateral femoral condyles on a pixel-by pixel basis, it can form the basis for developing maps of cartilage thickness. FIG. 11 shows an example of a 2D map of cartilage thickness derived from the surface normals of the lateral femoral condyle. FIG. 11A shows a proton density fast spin-echo MR image that demonstrates a focal cartilage defect in the posterior lateral femoral condyle (black arrows). White arrows indicate endpoints of thickness map. FIG. 11B is a 2D cartilage thickness map that demonstrates abrupt decrease in cartilage thickness in the area of the defect (arrows). The A thickness between neighboring pixels can be used to define the borders of the cartilage defect. Note diffuse cartilage thinning in area enclosed by the astericks (*).

In another embodiment, cartilage sensitive images can be used instead of T1-weighted or T2-weighted scans and the surface match can be performed based on the cartilage contour.

Alternatively, anatomic landmarks present on both baseline and follow-up scans can be used to match the data obtained during the baseline and those obtained during the follow-up scan. Another alternative for matching the baseline and the follow-up scan includes the use of external or internal fiducial markers that can been detected with MR imaging. In that case, a transformation is performed that matches the position of the markers on the follow-up scan with the position of the markers on the baseline scan or vice versa.

Obtaining an External Image of Joint/Bones

Before merging or superimposing morphological maps of articular cartilage obtained by MR imaging with biomechanical data, one must obtain the biomechanical data. Such biomechanical data include, but are not limited to, estimations of static loading alignment in standing or weight-bearing position and lying or non-weight-bearing position, as well as during joint motion, e.g., the movement of load-bearing pathway on the cartilage in the knee joint during gait. Biomechanical data may be generated using theoretical computations, based on data stored in a database that can be accessed by calling up and screening for certain characteristics. Alternatively, gait analysis may be performed for an individual and data obtained during gait analysis may be merged or fused with morphological MRI data. Morphological data and biomechanical data can then be easily displayed simultaneously using different colors, opacities, and or gray scales. Additionally, the load-bearing pathway, for example around a cartilage defect, can be plotted or superimposed onto morphological maps.

Preferably, reference markers or fiducial markers can be applied to the external surface on the skin overlying the joint. These markers adhere to the skin are typically made of materials that can be detected with MRI and that can be used to register joint motion during biomechanical analysis, e.g. gait analysis. These markers can then be used to correlate the morphological with the biomechanical data.

Simultaneous display of morphological data with biomechanical data provides a useful tool to assess the load pathway applied to articular cartilage and inside and around cartilage defects. Estimation of load pathway applied in and around a cartilage defect can be used to assess a cartilage defect and to guide the choice of therapy, e.g. treatment with chondroprotective or chondroregenerative agents, osteochondral allografting, cartilage transplantation, femoral or tibial osteotomy, or joint replacement surgery.

Recording Static Joint/Bones and Joint/Bones in Movement

In obtaining an external image of the bones on either side of a joint, one must record a static image as well as a moving image of the subject joint and bones. For analysis of the knee joint, gait analysis techniques have been shown to be very effective in generating accurate, reproducible data on the six degree of freedom motion of the knee. The motion of the knee joint can be quantified in terms of flexion, rotation and displacement. Fidelity in the dynamic visualizations of subject specific MR generated knee geometry and subsequent contact surface determination call for a high degree of accuracy for the motion capture portion of the studies.

Gait Analysis Activities

In performing a gait analysis, a subject is tested standing still, laying down, walking or running on a level surface, flexing a leg in a standing position, ascending and descending stairs, flexing the leg in a seated position, and the like. The level walking measurements can include, but is not limited to, six stride cycles for each side over a range of walking speeds. The subject can be instructed to walk at a comfortable speed (normal), slower than normal and faster than normal. Typically, this protocol produces gait measurements over a range of walking speeds. The standing and laying portions of the protocol can be used in the cross registration to the MR data. The instrumentation preferably includes, at least a two camera, video-based opto-electronic system for 3-D motion analysis, a multi-component force plate for measurement of foot-ground reaction force and a computer system for acquisition, processing and analysis of data.

Anatomic Coordinate Systems

Figure 12A:
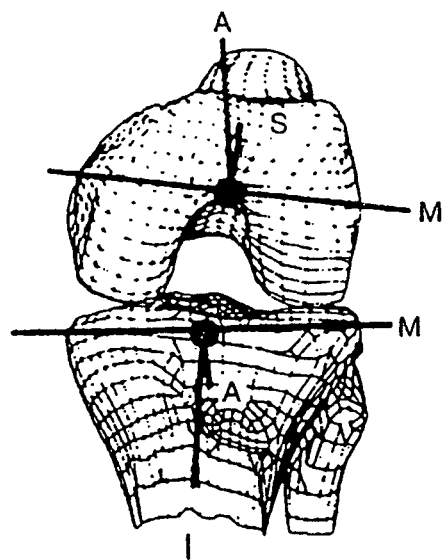
FIGS. 12A and 12B show the anatomic coordinate system in the femur and in the tibia.
Figure 12B:
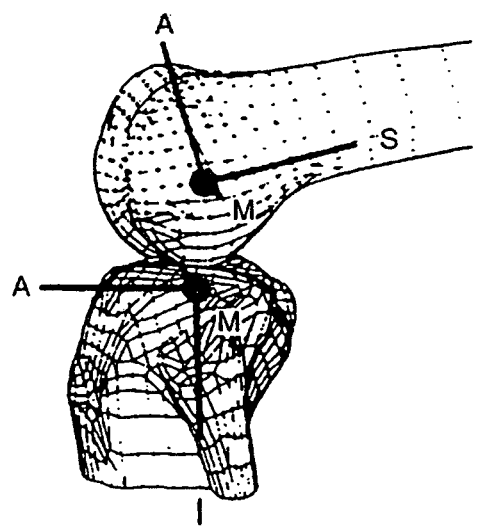
Figure 13:
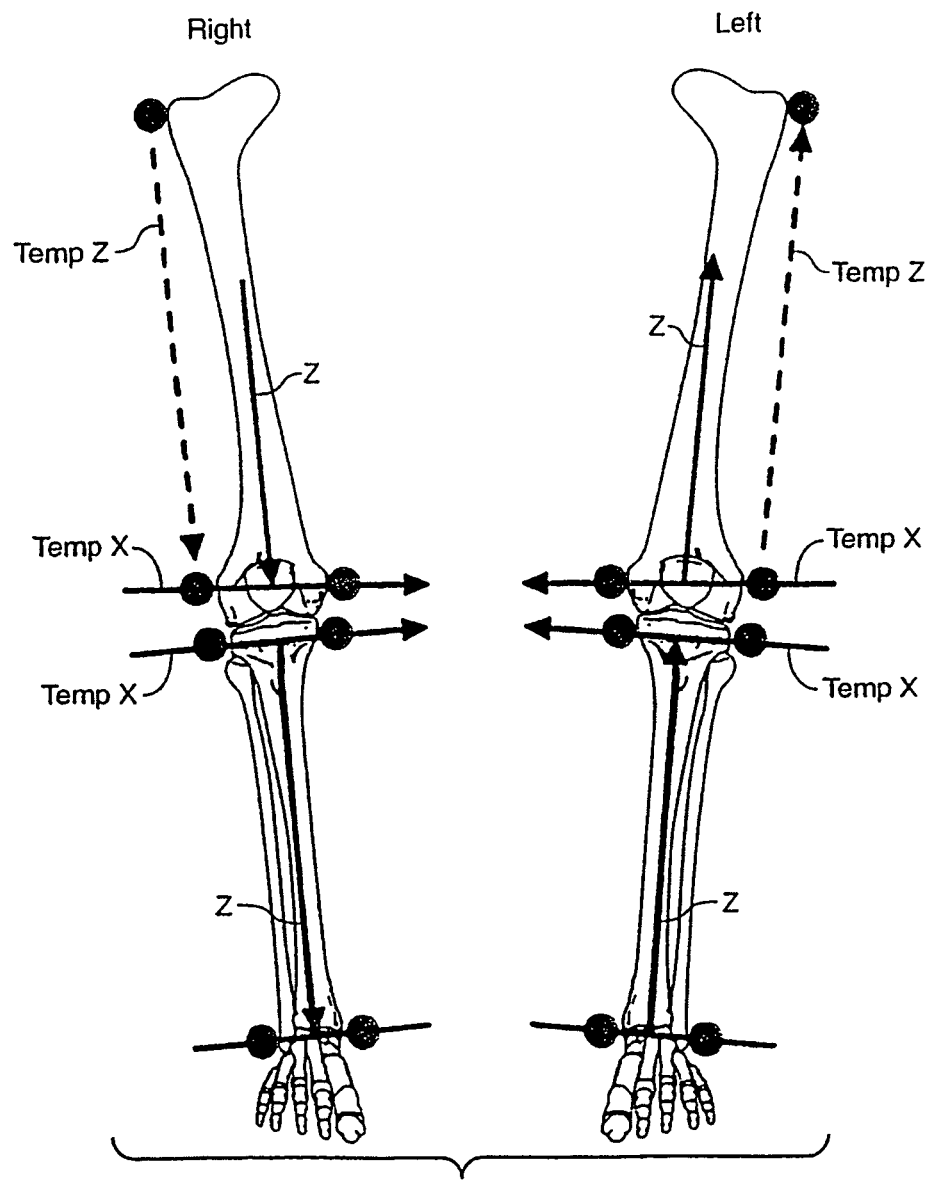
FIG. 13 shows calculation of the anatomic coordinate system from palpable bony landmarks.

Currently, the anatomic coordinate systems are defined through bony landmarks which can be identified through palpation. To describe the motion of the underlying bones in terms of the global coordinate system a subset of the markers in a point cluster technique (discussed hereinafter) are referenced to bony landmarks on the femur and tibia. Techniques described previously by Hopenfeld and Benedetti can be used to locate these bony landmarks. The anatomic coordinate systems used can be similar to that previously described by LaFortune with the exception of the origin of the femoral coordinate system. For the thigh segment, a coordinate system is located in the femoral condyles. The femoral condyles medial (M)-lateral (L) axis (FIG. 12) runs through the trans-epicondylar line (a line drawn between the medial-lateral femoral epicondyles). The midpoint of this axis is the origin. The inferior (I)-superior (S) axis runs parallel to the long axis of the femur, passing through the midpoint of the trans-epicondylar line. The anterior (A)-posterior (P) axis is the cross product of the medial-lateral and inferior-superior axes. The final position of the inferior-superior axis is made orthogonal to the anterior-posterior and medial-lateral axis through a cross product operation (FIG. 13). For the shank segment, the tibial coordinate system begins with the medial-lateral axis running through the most medial and lateral edges of the plateau. The inferior-superior axis is perpendicular to the medial-lateral axis passing through the tibial eminence. The anterior-posterior axis is the cross product of the medial-lateral and inferior-superior axes.

Placement of Markers Prior to Activity

Figure 14B:
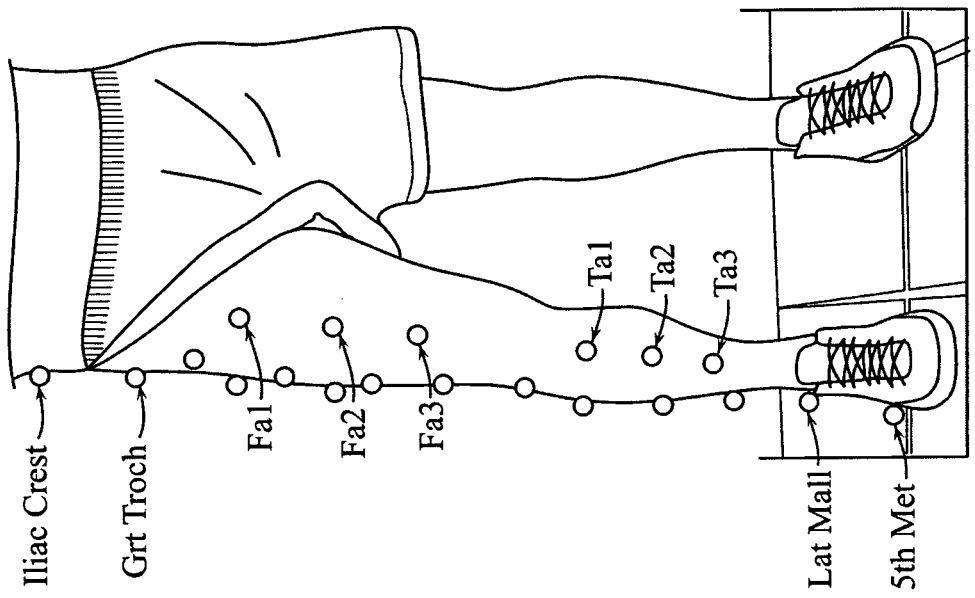
FIGS. 14A and 14B show additional marker names and locations for MR to optical cross registration.
Figure 14A:
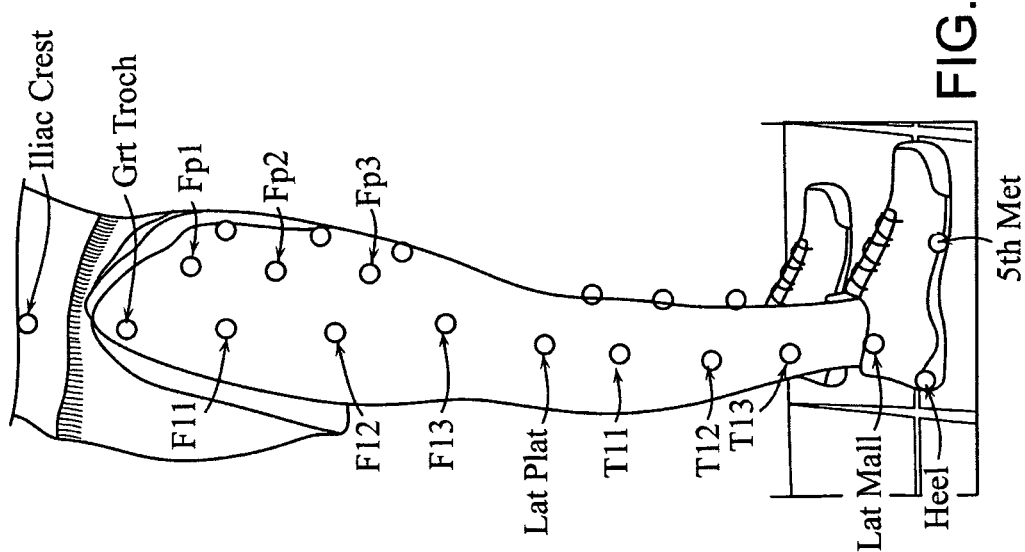
Figure 16A:
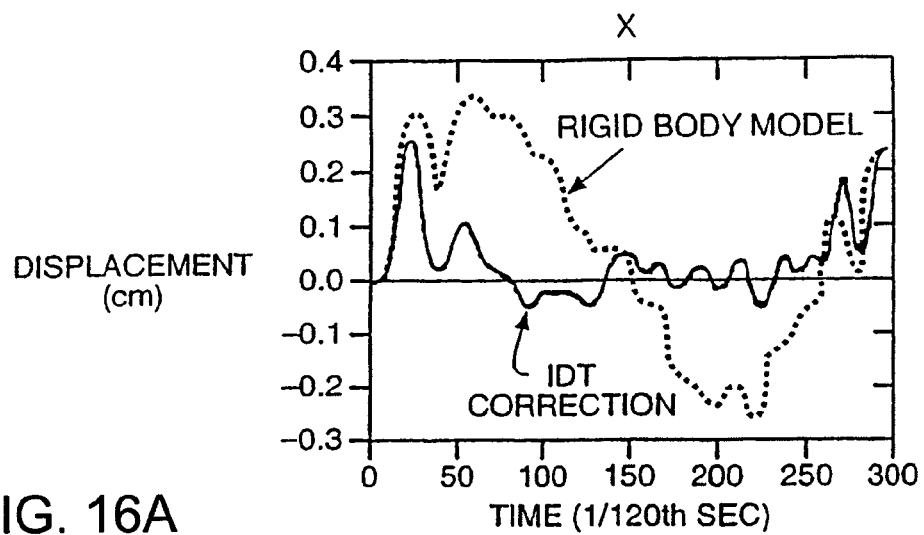
FIGS. 16A-C show the error in the tibial location estimate for the rigid body model and the intrical deformation correction technique.
Figure 16B:
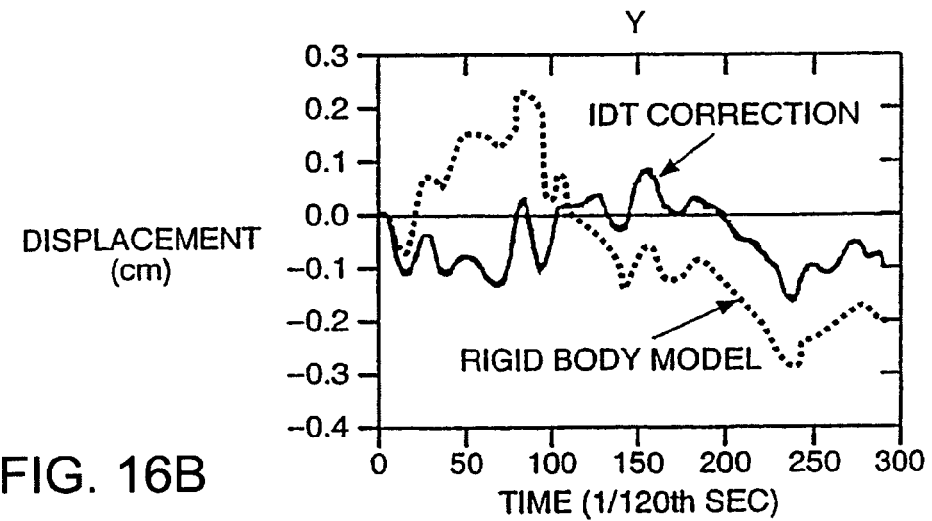
Figure 16C:
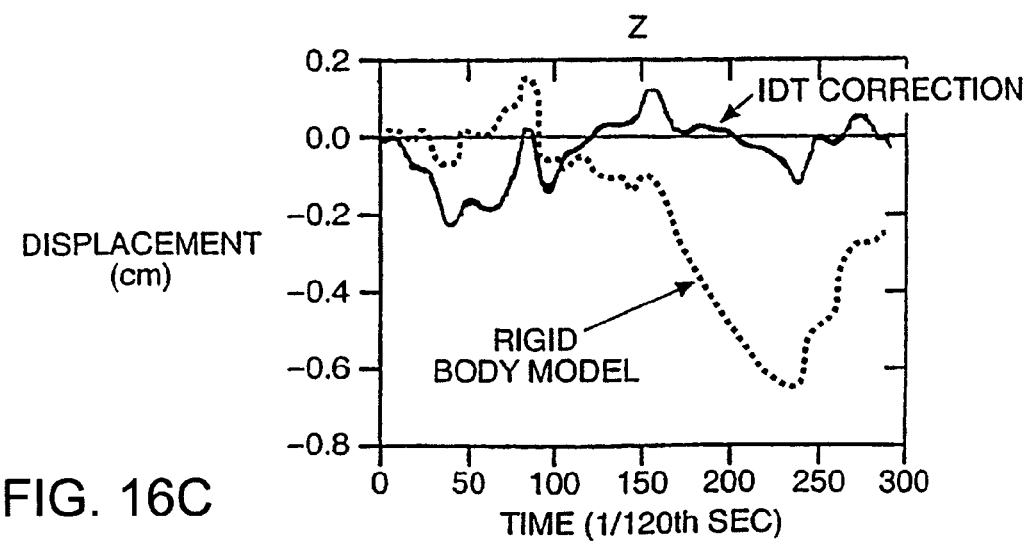
Figure 17A:
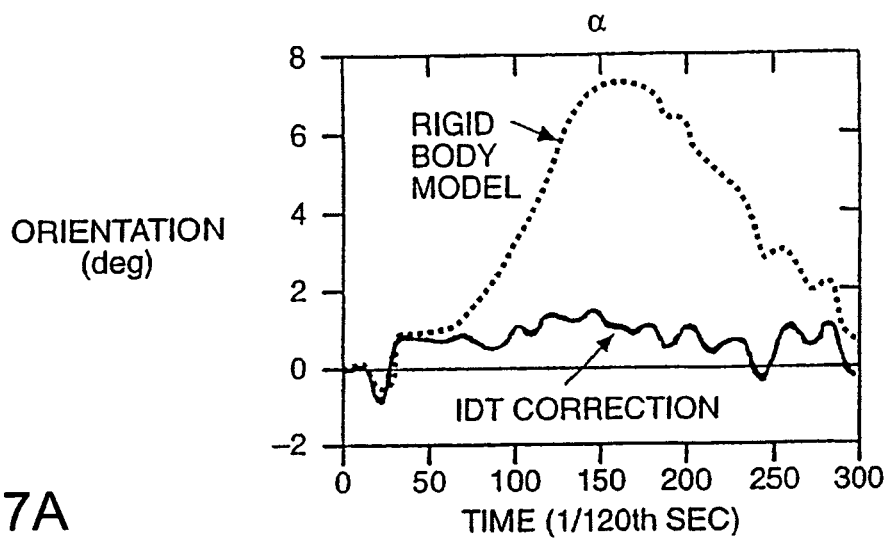
FIGS. 17A-C shows the error in tibial orientation estimate for the rigid body model and the interval deformation correction technique.
Figure 17B:
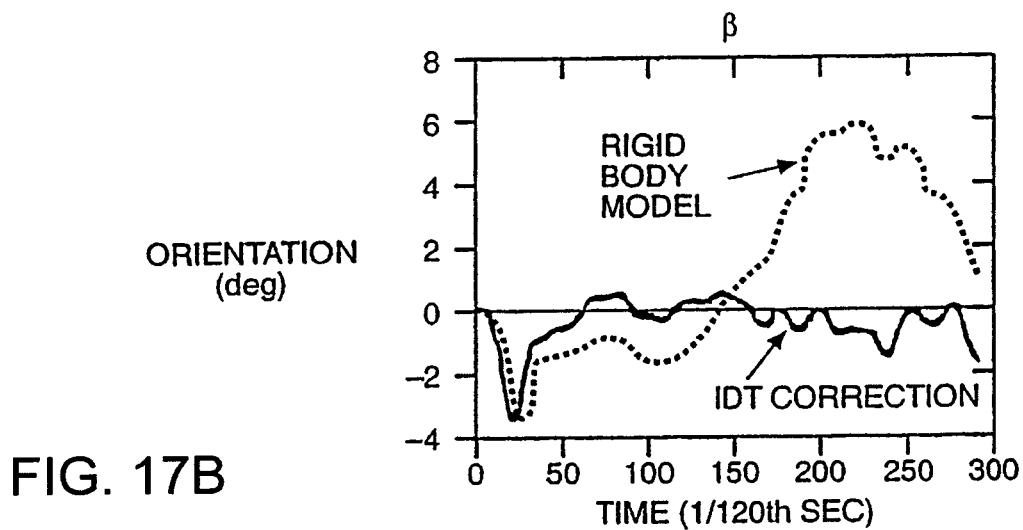
Figure 17C:
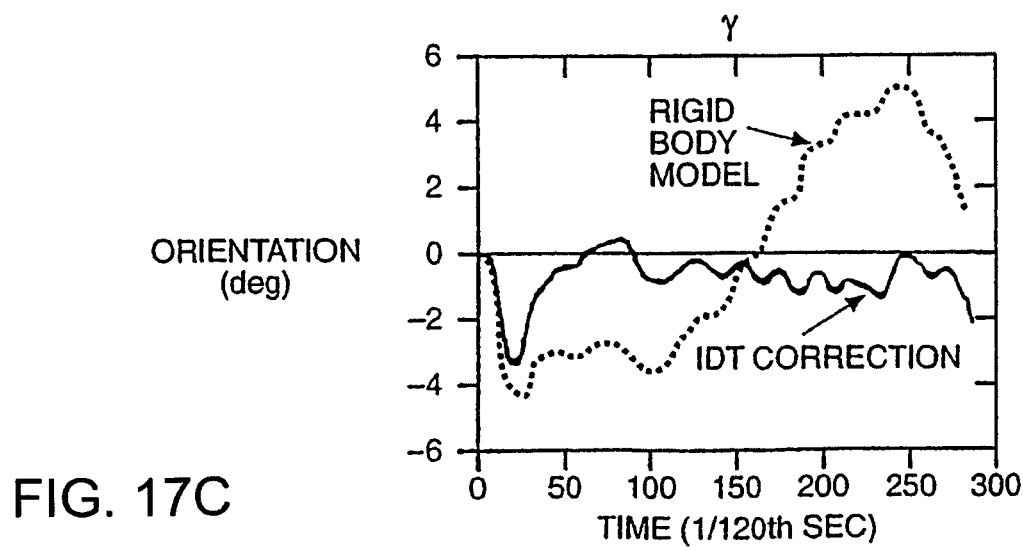

In assessing a joint, the lower extremity can be idealized as 3 segments with six degree-of-freedom joints at the knee and ankle. For the mobile activities described above, at least 3 markers per segment are used. FIG. 14 shows 21 passive retro-reflective markers located on the leg: some at bony prominences (greater trochanter, lateral malleolus, lateral epicondyle, lateral tibial plateau), some clustered on the thigh and shank (Fa1-3, 11-3, Fp1-3 Ta 1-3, T11-13). Additionally, two markers are placed on the foot at the lateral aspect of the calcaneus and base of the fifth metatarsal and one on the pelvis at theiliac crest). During the static activities (standing still, laying down) 7 additional markers are placed: medial malleolus, medial epicondyle, medial tibial plateau, medial and lateral superior patella, medial and lateral inferior patella. The eight markers nearest to the knee joint can be filled with Gadolinium, and can be replaced at these same locations prior to the MR images (FIG. 15). The locations can be marked with a non-toxic marker-pen.

Reference Database

The reference database is typically a compendium of demographic and motion analysis data for all subjects whose data has been processed by a central processing site. This database can contain fields describing each of the subject's name, age, height, weight, injury types, orthopedic medical history, other anatomic measurements (thigh length, shank length, shoe size, etc.). The database can also contain the results of any and all gait analysis run on these patients. This can include, for all activities tested (walk, run, jog, etc.), a number of peak valves (peak knee flexing, peak hip adduction movement; toe-out, angle, etc). along with the motion trajectories of the limb segments while the subjects are performing different activities.

In order to obtain a typical motion profile, the sex, age, height, weight, limb length, and type of activity desired can be entered as an average into the database. The database searches for a set of subjects most closely watching the input average. From this set of data, a typical motion pattern is distilled and a data set is output. This data set can include, over a time interval, the motion characteristics: hip/knee/ankle/flexion/extension angles, knee/hip/ankle adduction/abduction angles, movement, stride length, cadence, etc. This data can then be used to drive an animation of the motion of the desired joint.

Process Image of Joint/Bones

Calculation of Limb Segment Parameters

Each limb segment (thigh, shank and foot) can idealized as a rigid body with a local coordinate system defined to coincide with a set of anatomical axes (the assumption of rigidity is dropped in calculating the location of the femur and tibia). The intersegmental moments and forces can be calculated from the estimated position of the bones, the ground reaction force measurements, and the limb segment mass/inertia properties. The moment at the knee can be resolved into a coordinate system fixed in a tibial reference system with axes defining flexion-extension, abduction-adduction, and internal-external rotation.

This approach provides results in a range of patients in a highly reproducible manner. Typically the magnitudes of the moments are dependent on walking speed. To control for the influence of walking speed, the walking speed closest to 1 meter/second is used. This speed is within the normal range for the type of patients for which the invention is particularly useful. In addition to the gait trial collected at 1 meter/second, self-selected speeds can also be evaluated to give a good correlation between gait-quantitative estimates of joint load lines and other measures when using self-selected speeds. In order to test patients under their typical daily conditions, medications should not be modified prior to gait analyses.

Point Cluster Technique

The Point Cluster Technique (PCT) movement analysis protocol is an extensible and accurate approach to bone motion estimation. Basically, a number of retro-reflective markers (e.g. retro-reflective material from 3M, Corp.) are attached to each limb segment under observation. Multiple video cameras can acquire data with the subject standing still and during activities of interest. An over-abundance of markers on each limb segment is used to define a cluster coordinate system, which is tied to an anatomically relevant coordinate system calculated with the subject at rest.

The standard PCT transformations are described below. In short, each marker is assigned a unit mass and the inertia tensor, center of mass, principal axes and principal moments of inertia are calculated. By treating the center of mass and principal axes as a transformation, local coordinates are calculated. Another set of coordinate systems is established; limb segment specific anatomic landmarks are identified through palpation and a clinically relevant coordinate system defined. For the femur and tibia, these anatomic coordinate systems are shown in FIG. 12. The transformation from the reference cluster coordinate system to the anatomic coordinate system is determined with the subject at rest by vector operations. During an activity, the transformation from the global coordinate system to the cluster coordinate system is calculated at each time step. To place the anatomic coordinate in the global system during the activity, the reference coordinate system to anatomic system transformation is applied, followed by the inverse global coordinate system to cluster coordinate system transformation for each time step.

In the Point Cluster Technique (PCT) a cluster of N markers can be placed on a limb segment of the subject. The location vector of each marker in the laboratory coordinate system is denoted as G(i,t) for marker i, (i=1, 2, ..., N) at time t, $t_o \le t \le t_f$. A unit weight factor is assigned to each marker for the purpose of calculating the center of mass, inertia tensor, principal axes and principal moments of inertia of the cluster of markers. The cluster center of mass and principal axes form an orthogonal coordinate system described as the cluster system. The local coordinates of each of the markers relative to this coordinate system are calculated. Then $$G(i,t) = C(t) + E(t) \cdot L(i,t) = T_c(t) \cdot L(i,t) \quad i=1 \ldots N$$

where G(t) is a matrix of all marker coordinate vectors, C(t) is the center of mass of G(t), E(t) is the matrix of eigenvectors of the inertia tensor of G(t), and L(i,t) are the local coordinates of marker i.

These markers are observed by opto-electronic means while the subject performs activities and while standing completely still in a reference position. With the subject in this same reference position, a subset of the markers is observed relative to the underlying bones by other techniques, which might include x-rays, CT scan, or palpation.

The measured marker locations are defined with respect to the unobservable location and orientation of the bone by $$G(i,t) = P(t) + O(t) \cdot R(i,t) = T_b(t) \cdot R(i,t) \quad i=1 \ldots N$$

where P(t) is the location and O(t) is the orientation of a coordinate system embedded in the bone and R(i,t), also unobservable, are the trajectories of the markers relative to the underlying rigid body coordinate system at time t. The bone and cluster systems are each orthogonal systems, related by the rigid body transformation $T_{bc}(t)$:

$$L(i,t) = T_{bc}(t) \cdot R(i,t)$$

substituting and eliminating R(i,t) yields $$T_b(t) = T_c(t) * T_{cb}(t)$$

To maintain physical consistency, $T_{cb}(t) = T_{bc}(t)^{-1}$ must be the inertia tensor eigendecomposition transformation of R(i, t). Once R(i,t) are specified, $T_{cb}(t)$ and subsequently $T_b(t)$ are calculable.

Point Cluster to Anatomic Coordinate System Transformation

From these equations one can also relate the global coordinate system with respect to a limb segment system. As an example of how these systems can be used to describe joint motion, one can consider the tibio-femoral joint. The motion that is of interest is how the femoral condyles move with respect to the tibial plateau. This is done by first defining a set of coordinate axes in the femoral condyles and the tibial plateau.

A coordinate system is located in both the femoral condyles and the tibial plateau. The femoral condyles medial-lateral (ML) axis runs through the trans-epicondylar line (TEL), a line drawn between the ML femoral epicondyles. The midpoint of this axis is the origin. The inferior-superior (IS) runs parallel to the long axis of the femur, passing through the midpoint of the TEL. The anterior-posterior (AP) is the cross product of the ML and IS axes. The tibial coordinate system begins with the ML axis running through the most medial and lateral edges of the plateau. The IS axis is perpendicular to the ML axis passing through the tibial eminence. The AP axis is the cross product of the ML and IS axes. These are known as the anatomic coordinate system $(A(t)_{thigh}, A(t)_{shank})$.

Relating the cluster system to the anatomic coordinate system is done by use of another transformation matrix. This is done by relating the thigh cluster to a cluster of markers, a sub cluster, that is related to the femoral condyles and femur (cluster to anatomic transformation).

$$R(t)_{thigh} = U(t)_{high} A(t)_{thigh}$$

The tibia has a similar transformation matrix.

$$R(t)_{shank} = U(t)_{shank} A(t)_{shank}$$

Therefore, from a cluster of markers in the global system, motion of the femur with respect to the tibia can be determined by:

$$TS(t) = A(t)_{thigh} \cdot G(t)_{thigh} \cdot R(t)_{shank} \cdot A(t)_{shank}$$

Here TS(t) is the motion of the thigh with respect to the shank.

Angles are calculated by a projection angle system, an axis from the femoral anatomic system and one from the tibia are projected onto a plane in the tibial coordinate system. For example, flexion/extension can be determined by projecting the IS axis of the femur and tibia onto the sagittal plane (AP-IS plane) of the tibia.

Validation of the Point Cluster Technique

The point cluster technique was evaluated as a method for measuring in vivo limb segment movement from skin placed marker clusters. An Ilizarov device is an external fixture where 5 mm diameter pins are placed directly into the bone on either side of a bony defect. The rigid external struts affixed to these pins form a rigid system fixed in the underlying bone. Two subjects were tested with Ilizarov fixation devices. One subject had the Ilizarov device placed on the femur and second subject had the device placed on the tibia. Each subject was instrumented with point clusters placed on the thigh and shank segment. In addition, markers were placed on the Ilizarov device to establish a system fixed in the underlying bone.

The relative angular movement and translational displacement between the system affixed in the bone and the point cluster coordinate system were calculated while ascending a 20-cm step (Step Test). Angular changes between the three orthogonal axes fixed in the bone versus three axes in the point cluster were calculated. The average difference over the trials for three axes were $0.95 \mp 1.26$, $2.33 \pm 1.63$, and $0.58 \pm 0.58$ degrees. Similarly, the average error for the distance between coordinate systems was $0.28 \pm 0.14$ cm. The second subject with the Ilizarov device placed on the femur could not perform the Step-Test, but was able to perform a weight-bearing flexion test where his knee flexed to approximately 20° from a standing position. The average change between the coordinate origin was $0.28 \pm 0.14$ cm. The changes in axis orientation were $1.92 \pm 0.42$, $1.11 \pm 0.69$ and $1.24 \pm 0.16$ degrees.

The simultaneously acquired motion for a coordinate system embedded in bone (Ilizarov system) and a set of skin-based markers was compared. At every time instant the location and orientation of the Ilizarov system, the rigid body model skin marker system, and the interval deformation technique skin marker system were determined. The change in the transformation from the Ilizarov system to one of the skin marker systems over time is a measure of the deformation unaccounted for in the skin marker system.

The interval deformation technique produced a substantial improvement in the estimate of the location and orientation of the underlying bone. For perfectly modeled motion there would be no relative motion between the Ilizarov system and the skin marker system over the time interval. The change in the transformation from the Ilizarov system to the skin marker systems are shown in FIGS. 14 and 15, for location and orientation respectively, for both a rigid body model and the interval deformation technique. For this single data set, the location error was reduced from 7.1 cm to 2.3 cm and the orientation error from 107 degrees to 24 degrees, with the error summed over the entire time interval. The subject performed a 10 cm step-up; the marker deformation was modeled as a single Gaussian function.

Deformation Correction

There are a number of algorithmic alternatives available to minimize the effects of skin motion, soft tissue deformation, or muscle activation that deform the externally applied markers relative to the underlying bone. The Point Cluster Technique decreases the effects of marker movement relative to the underlying bone through averaging. If more correction is required, one of a number of deformation correction techniques may be added. In order of increasing computational complexity and deformation correction ability, these are rigid body linear least square error correction, global optimization correction, anatomic artifact correlation correction and interval deformation correction.

An overview of the Interval Deformation Correction Technique is given below. In short, the technique provides a maximum likelihood estimate of the bone pose, assuming that each marker on a limb segment deforms relative to the underlying bone in some functional form. The technique parameterizes these functional forms and then performs a multi-objective non-linear optimization with constraints to calculate these parameters. This is an extremely computationally intensive technique, with the current instantiation of the algorithm requiring 6-8 hours per limb segment of running time on 266 MHz Pentium 2 computer.

Interval Deformation Technique

Since Tc can be calculated directly from the global coordinates of the markers, the remainder of this development only examines the determination of R(i,t) and subsequently $T_{cb}(t)$. For this reduced problem, the input data is the local coordinates in the cluster system L(i,t) for all i, $T_o \leq t \leq t_f$. It can be assumed that each marker has some parameterized trajectory, $d(a_{ij}, t)$, relative to the underlying bone at each time step, with independent and identically distributed noises v(i, j, t)

$$R_j(i,t) = d(a_{ij},t) + v(ij,t) \, j=1\ldots 3 \, i=1\ldots N$$

or, equivalently $$R(i,t) = F(a_i,t) + v(i,t) \, i=1\ldots N$$

where $a_{ij}$ is a vector of parameters for marker i, ordinate j; $a_i$ is a vector of parameters combining all of the parameters for all of the ordinates of marker i. Then the estimate of the data, M(i,t), can be given by $$M(i,t) = T_{bc}(t) \cdot R(i,t)$$

Without further restrictions the problem is indeterminate, as the locations of the markers in the bone system R(i,t) are never observable with the opto-electronic system. The indeterminate problem can be converted to a chi-squared estimate problem through a series of steps. An observation of the truly unobservables at the time boundaries is inferred; that is, it is assumed that $T_{cb}(t \leq t_o)$ and $T_{cb}(t \geq t_f)$ are observed. The value of $T_{cb}$ can be selected depending on the activity being studied. For example, consider the step up activity, where the subject starts and stops in the reference position. For this activity the body is not deforming outside the estimation interval; that is, the markers are not moving with respect to the bone:

$$T_{cb}(t<t_o) = T_{cb}(t=t_o) \text{ and } T_{cb}(t>t_f) = T_{cb}(t_f)$$

It can now be assumed that the noise functions v(i, j, t) are normal distributions with individual standard deviations σ(i, j, t), the probability P(ij,t) of the data for ordinate j, marker i, time t being a realization of the stochastic process is given by:

$$P(i, j, t) \propto \exp\left(-\frac{1}{2}\left(\frac{L(i, j, t) - M(i, j, t)}{\sigma(i, j, t)}\right)^2\right)$$

Provided the noise functions v(i, j, t) are independent of each other, the probability of the entire data set being a realization is a product of each of the individual probabilities:

$$P(i, j, t) \propto \prod_{i=1}^{N} \prod_{j=1}^{3} \prod_{t=t_0}^{f_i} \exp\left(-\frac{1}{2}\left(\frac{L(i, j, t) - M(i, j, t)}{\sigma(i, j, t)}\right)^2\right)$$

Maximizing this probability can be equivalent to minimizing the negative of its logarithm, yielding the familiar chi-square criteria. As an intermediate step the following error matrices can be defined:

$$X(a, t) \ni X(a, t)_{i,j} = \left(\frac{L(i, j, t) - M(i, j, t)}{\sigma(i, j, t)}\right)^2 \quad i = 1\ldots N \quad j = 1 \ldots 3$$

$$X(a) = \sum_{t=t_0}^{t_f} X(a, t)$$

and seek a which in some sense minimizes X(a), a matrix whose elements represent the error over the entire time interval for each ordinate of each marker. If the normal noise distribution assumption is true, then this minimization results in the maximum likelihood estimate of the parameterization, and by inference maximum likelihood estimate of the transformation from the bone system to the cluster system. If the normal noise assumption is not true, the chi-squared estimate is still appropriate for parameter estimation; the results cannot be interpreted as a maximum likelihood estimate, but, for example, confidence regions on the estimate or the formal covariance matrix of the fit can be determined.

Obtaining the parameter set a is a computationally complex operation. The approach taken was to define a scalar to represent this entire error matrix, $$f(a) = \sum_{i=1}^{N} \sum_{j=1}^{3} X(a)_{i,j}$$

and seek a that minimizes f(a).

The limits on marker motion previously discussed can now be converted into deformation constraints, which allow the formulation of the problem as a general non-linear programming problem. The constraints arise from two sources; human limb segments do not deform outside a small range, and the locations of the markers are chosen with specific properties in mind. For computational purposes, the deformation constraints are selected to be:

1. The axes of the cluster system moves by less than 15 degrees relative to the bone system.
2. The center of mass of the cluster system moves by less than 3 cm relative to the bone system.
3. The markers move by less than 4 cm relative to the bone system.
4. Each of the principal moments of inertia of the cluster system change by less than 25 percent from the reference values.

The Point Cluster Technique marker set was designed to ensure that the cluster of points is non-coplanar and possess no axes of rotational symmetry. These properties ensure a local coordinate system that is well defined and unambiguous over the entire time interval. The constraints are then:

5. The ratio of the smallest principal moment of inertia of the cluster system to the largest is more than 5 percent; the magnitude of the smallest principal moment of inertia of the cluster system is greater than some small positive value.
6. The principal moments of each axis are different from each other by at least 5 percent.

The general problem can then be formulated:

Minimize f(a)

$a \in R^D$

Subject to:

$g_i(a) = 0 \; i = 1 \ldots m_e$ $g_i(a) \square 0 \; i = m_e+1 \ldots M$ $a_l \leq a \leq a_u$ where D is the total number of parameters; $m_e$, the number of equality constraints, is 0; and m, the total number of constraints, is 10.

The approach taken to verify the operation of the algorithm implementation began with generating a set of 50 synthetic data sets with known characteristics. The program was then applied to all of the data sets. The program results were then compared to the known, generated deformation. Error results were calculated for both the interval deformation technique descried herein and for the standard rigid body model formulation.

The 50 trial data sets were processed through the algorithm. The results over all of the trial sets are summarized in Table I, where the center of mass and direction cosine error of the interval deformation technique and the rigid body model are compared. After processing by the interval deformation algorithm the center of mass error has been reduced to 29% and the direction cosine error has been reduced to 19% of the rigid body model error. In a t-test for paired samples, both of these decreases were significant at p<0.001.

Validation of the Interval Deformation Correction Technique

A subject fitted with an Ilizarov external fixation was observed with the optoelectronic system. The Point Cluster Marker set was affixed to the subject's shank (6 markers), along with a set of four markers rigidly attached to the Ilizarov device, which is rigidly connected to the tibia with bone pins. These four markers define a true bone embedded coordinate system. Data were acquired by GaitLink software (Computerized Functional Testing Corporation) controlling four Qualisys cameras operating at a video frequency of 120 Hz. Three dimensional coordinates were calculated using the modified direct linear transform.

The subject was a 46 year old male (height 1.75 m, weight 84.1 kg) fitted with a tibial Ilizarov external fixation device. The device was rigidly attached to the tibia with nine bone pins, located in three sets (top, middle, and bottom) of three (medial, anterior, and lateral). The clinical purpose of the device was tibial lengthening; the test on the subject was performed two days prior to final removal of the device. The subject exhibited a limited range of motion and was tested performing a 10 cm step-up onto a platform.

The simultaneously acquired motion for a coordinate system embedded in bone (Ilizarov system) and a set of skin-based markers was compared. At every time instant the location and orientation of the Ilizarov system, the rigid body model skin marker system, and the interval deformation technique skin marker system was determined. The change in the transformation from the Ilizarov system to one of the skin marker systems over time is a measure of the deformation unaccounted for in the skin marker system.

The interval deformation technique produced a substantial improvement in the estimate of the location and orientation of the underlying bone. For perfectly modeled motion there would be no relative motion between the Ilizarov system and the skin marker system over the time interval. The change in the transformation from the Ilizarov system to the skin marker systems are shown in FIGS. 14 and 15 for location and orientation respectively, for both a rigid body model and the interval deformation technique. For this single data set, the location error was reduced from 7.1 cm to 2.3 cm and the orientation error from 107 degrees to 24 degrees, with the error summed over the entire time interval. The subject performed a 10 cm step-up; the marker deformation was modeled as a single Gaussian function.

Correlating Results from Gait Analysis and Geometrical Representations of the Bone In correlating the load pattern obtained from a gait analysis using, e.g. the PCT, with the geometrical representation of the bone from the segmented MRI data, one can be guided by the general process as described below. The process allows for dynamic visualization (i.e. animations) of high-resolution geometrical representations derived from MRI scans (or other imaging techniques). The motion of the subject specific anatomic elements is generally driven by data acquired from the motion (gait) lab. Fidelity of these animations requires calculation and application of a sequence of rigid body transformations, some of which are directly calculable and some of which are the result of optimizations (the correction for skin marker deformation from rigidity does not use the rigid body assumption, but generates a correction that is applied as a rigid body transform).

The process comprises:
a) acquiring data from MRI (or other imaging techniques), and PCT gait protocols;
b) directly calculating a set of transformations from the data;
c) calculating a set of transformations from optimizations, as needed;
d) generating a 3D geometric representation of the anatomic element from the MR data; and
e) applying the transformations of (b) and (c) to the 3D geometric representation.

Each of these steps are described in detail below.

Acquiring the Data from MRI (or Other Imaging Techniques) and PCT Gait Protocols In the Point Cluster Technique (PCT) protocol, a patient can have a number of retro-reflective markers attached to each limb segment under observation. Multiple video cameras acquire data with the subject standing still and during activities of interest.

In addition, in order to correspond activities in the gait lab with the MRI scans, another reference data set (subject standing still, prescribed posture) can be acquired using 8 additional markers clustered about the knee. These markers are filled with gadolinium-DTPA and covered with a retro-reflective material to allow for correlation between the MRI image and the video data.

Directly Calculating a Set of Transformations from the Data

The transformations are described in detail in [Andriacchi T P, Alexander E J, Toney M K, Dyrby C O, Sum J. J Biomech Eng 1998; 120(12): 743-749]. In short, each marker can be assigned a unit mass and the inertia tensor, center of mass, principal axes and principal moments of inertia can be calculated. By treating the center of mass and principal axes as a transformation, local coordinates arcan be e calculated. Another set of coordinate systems can also be required for this technique; limb segment specific anatomic landmarks can be identified through palpation and a clinically relevant coordinate system can be defined. The required transformations are summarized in Table 1 below.

Calculating a Set of Transformations from Optimizations

There are three required transformations:

Optimization 1. One can calculate the linear least square error rigid body transformation from the MRI common local coordinate system to the VID common local coordinate system.

Optimization 2. For each limb segment, one can calculate the linear least square rigid body transformation from the MRI limb segment anatomic coordinate system to the video limb segment anatomic coordinate system (obtained from the gait analysis), using a subset of common markers appropriate for each segment.

Optimization 3. One can calculate a correction for the deviation of the limb segment from rigidity during each time step of the activity, using the PCT with either the mass redistribution [Andriacchi T P, Alexander E J, Toney M K, Dyrby C O, Sum J. J Biomech Eng 1998; 120(12): 743-749] or interval deformation algorithms [Alexander E J, Andriacchi T P: Correcting for deformation in skin-based marker systems. Proceedings of the 3rd Annual Gait and Clinical Movement Analysis Meeting, San Diego, Calif., 1998].

Generating a 3D Geometric Representation of the Anatomic Element from the MR Data The MR slices are segmented for the multiple anatomic and fiducial elements. The slices are combined to a voxel representation. An isosurface can be calculated from the boundary voxel elements. A tessellation of the isosurface can be calculated, along with the outward pointing normal for each surface element. This data can then be stored in a standard 3D graphic format, the Virtual Reality Modeling Language (VRML).

Appling the Transformation Sequence to the Geometric Representation

The transformation sequence is provided below in Table 1. This transformation sequence can be applied to each of the anatomic elements over each time step of the activity, starting with sequence 6.

TABLE 1

| SEQ | FROM SYSTEM | TO SYSTEM | $X_{FORM}$ |
|---|---|---|---|
| 1 | MR Global | MR Local | ED1 |
| 2 | MR Local | Common Local | OPT1 |
| 3 | Common Local | MR Anatomic | ANA2 |
| 4 | MR Anatomic | VID Anatomic | OPT2 |
| 5 | VID Anatomic | VD Ref | ANA3 |
| 6 | VID Ref | VID Deformed(t) | ED3 |
| 7 | VID Deformed(t) | VID Bone(t) | OPT3 |
| 8 | VID Bone(t) | VD Global(t) | ED4 |

Correlating Marker Sets

As pointed out at numerous places in the specification, the use of external reference markers that are detectable by both MRI and optical techniques can be an important and useful tool in the method of this invention. The use of the reference markers can form the basis for an aspect of this invention that is a method for correlating cartilage image data, bone image data, and/or opto-electrical image data for the assessment of the condition of a joint of a human. This method comprises, obtaining the cartilage image data of the joint with a set of skin reference markers placed externally near the joint, obtaining the bone image data of the joint with a set of skin reference markers placed externally near the joint, obtaining the external bone image data opto-eletrical image data of the joint with a set of skin reference markers placed externally near the joint. Using the skin reference markers, one can then correlate the cartilage image, bone image and opto-electrical image with each other, due to the fact that each skin reference marker is detectable in the cartilage, bone and opto-electrical data. The cartilage image data and the bone image data can be obtained by magnetic resonance imaging, positron emission tomography, single photon emission computed tomography, ultrasound, computed tomography or X-ray. Typically, MRI will be preferred. In the case of X-ray, further manipulations must be performed in which multiple X-ray images are assimilated by a computer into a 2 dimensional cross-sectional image called a Computed Tomography (CT) Scan. The opto-electrical image data can be obtained by any means, for example, a video camera or a movie camera. Multiple skin reference markers can be placed on one or more limbs of the patient prior to imaging. The skin reference markers are described hereinbefore.

By a sequence of calculations a set of transformations that will take the subject specific geometric representation of anatomic elements determined from the MR image set to the optical reference coordinate system. From the optical reference coordinate system, the standard Point Cluster Technique transformation sequence is applied to generate dynamic visualizations of these anatomic elements during activities previously recorded in the motion lab. Fidelity of these dynamic visualizations (and subsequent contact surface determination) requires the calculation and application of a sequence of rigid body transformations. Some of these are directly calculable and some are the result of optimizations (the correction for skin marker deformation from rigidity does not use the rigid body assumption, but generates a correction that is applied as a rigid body transform).

The first required transformation can be from the MR global coordinate system to the MR center of mass/principal axis coordinate system. This can be done by calculating the center of mass of each of the individual markers, resulting in a set of eight three dimensional points. Each of these points can be assigned a unit mass, and the center of mass, inertia tensor, and principal axes can be calculated. The same procedure can be performed on these markers as determined by the optical system, providing a transformation from the optical global system to a center of mass/principal axis system.

If the relative orientation of the tibia and femur as determined by the MR system and the optical system are identical, it is only necessary to apply the optical reference system to the anatomic system transformation of the MR local data. If this is not the case, an optimization calculation can be performed to determine the rotation and translation of, for example, the femur with respect to the tibia. One then can calculate the linear least square rigid body transformation from the MR limb segment anatomic coordinate system to the video limb segment anatomic coordinate system prior to applying the Point Cluster Transformations.

Figure 18A:
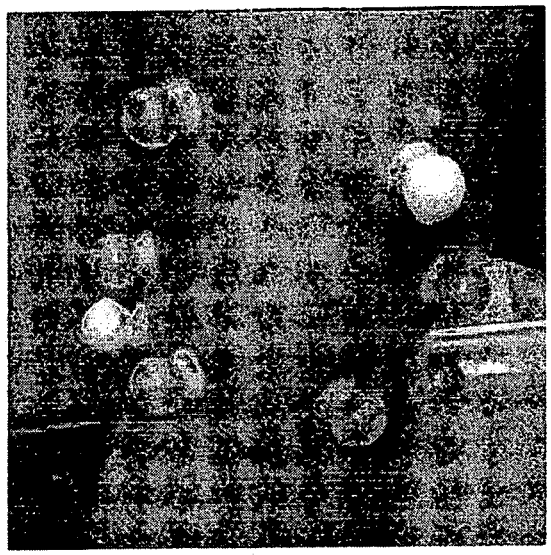
FIGS. 18A-18I show functional joint imaging.
Figure 18B:
Figure 18C:
Figure 18F:
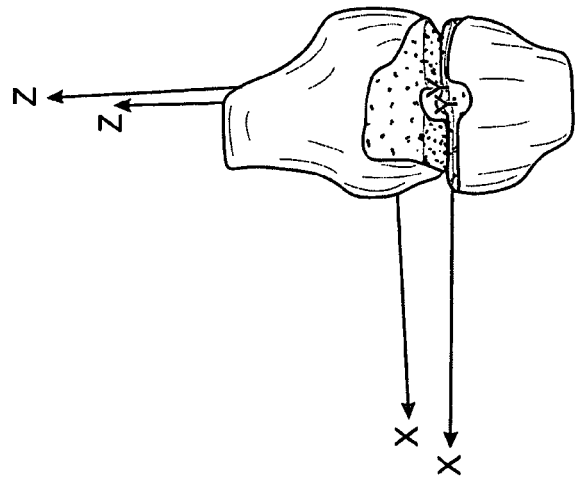
Figure 18E:
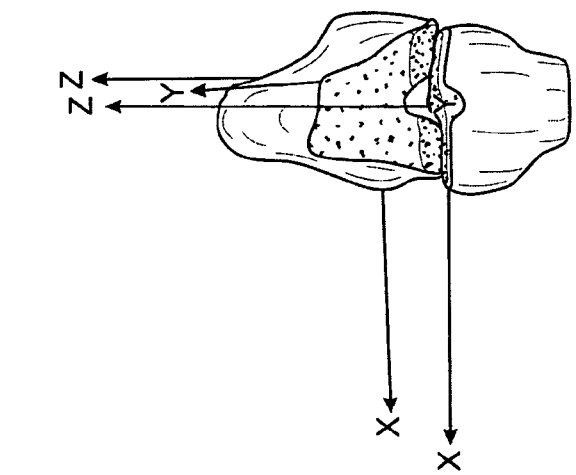
Figure 18D:
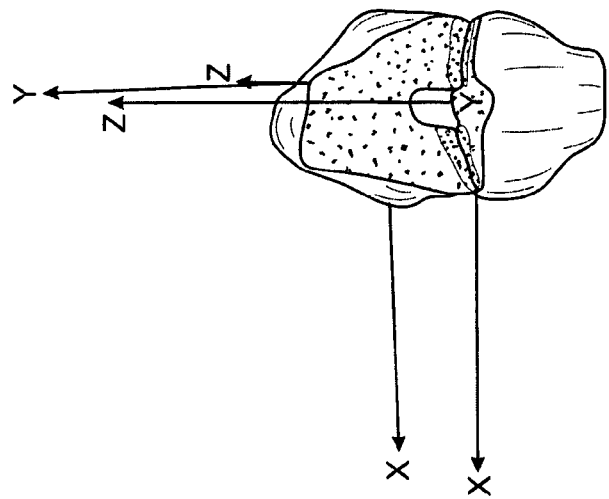
Figure 18I:
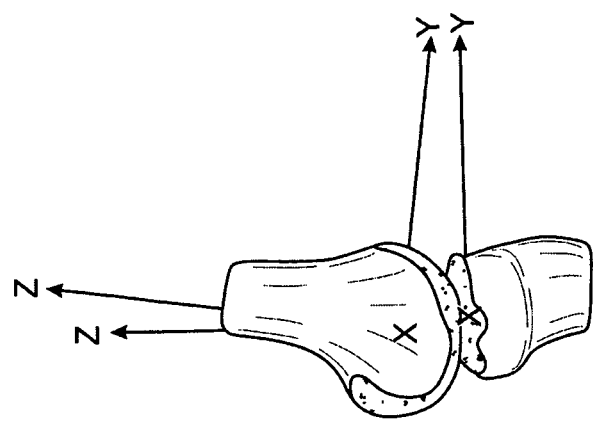
Figure 18H:
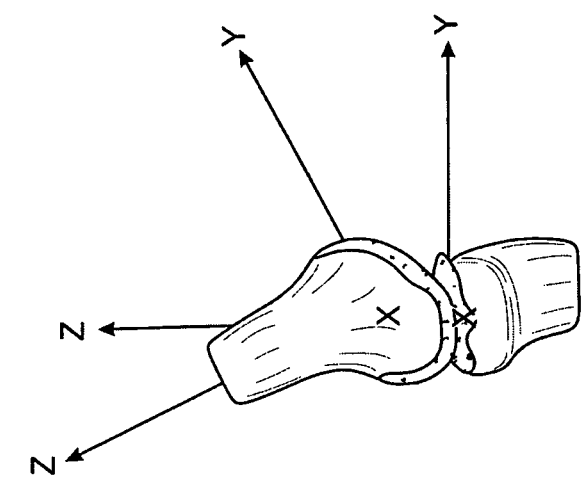
Figure 18G:
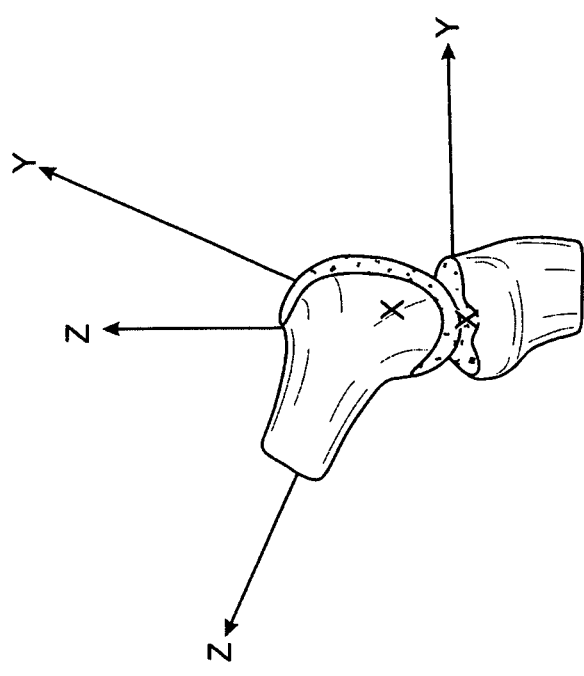

For visualization or contact surface determination, one can examine the relative motion of one segment to the other, for example the motion of the femur relative to a fixed tibial frame. This can be accomplished by applying the global to tibial anatomic system transform to all of the elements. An example of this type of visualization is given in FIG. 18. The Figure shows what can be referred to as functional joint imaging. FIG. 18A is a photograph demonstrating the position of the external markers positioned around the knee joint. The markers are filled with dilute Gd-solution. B is Sagittal 3D SPGR image through the medial femorotibial compartment. Two of the external markers are seen anteriorly as rounded structures with high signal intensity. C is 3D reconstruction of femoral and tibial bones (light grey), external markers (dark grey), femoral cartilage (red), and tibial cartilage (blue) based on the original SPGR MR images. D-I show a functional joint imaging sequence at selected phases of leg extension from a seated position, D-F, anterior projection. The vectors represent the relative location and orientation of the femur with respect to the tibia. G-I is a lateral projection. These dynamic visualizations can be used to demonstrate tibiofemoral contact areas during various phases if gait or other physical activities.

Figure 19:
FIG. 19 shows the superimposition of the tibiofemoral contact line onto the 3D cartilage thickness map.

Superimposition of Cartilage Thickness Map onto Subject Specific Anatomic Model and Determination of Distance of Cartilage Defect from Load Bearing Line Superimposing the cartilage thickness maps onto the subject specific geometric models can follow the same approach taken to bring the MR generated geometries into the optical reference system. Since the thickness maps and the geometric models are initially in the same coordinate system; one possible approach is to perform a simple surface mapping of the thickness map onto the geometric model. Another alternative approach is to convert the thickness map directly into a geometric representation (FIG. 19).

Once the thickness map is embedded in the femoral geometry, one can define a scalar metric that characterizes the location of any cartilage lesions relative to the point of contact line. One approach is a simple 3D distance along the surface from the center of the cartilage lesion to the point of closest approach of the contact line. Another metric that could be useful would be to multiply the area of the lesion by the adduction moment at that time instant, then divide by the distance from lesion center to point of closest approach. This could result in a metric that increases with lesion area, adduction moment, and closeness of approach.

Display Correlated Images

Determination of Anatomic and Natural Reference Lines

There are two alternative approaches one can consider for determining a reference line on the cartilage surfaces. One skilled in the art will easily recognize other approaches that can be suitable for this purpose. The first approach is based on anatomic planes; the second is a natural approach building on the three dimensional cartilage thickness map.

The location of the pathway of loading relative to the femoral and tibial anatomy and geometry can be assessed by defining sagittal planes bisecting the medial femoral condyle, the lateral femoral condyle, the medial tibial plateau, and the lateral tibial plateau. For the medial femoral condyle, the operator can manually delete surface points located along the trochlea. Then, a sagittal plane parallel to the sagittal midfemoral plane can be defined through the most medial aspect of the medial femoral condyle followed by a sagittal plane parallel to the sagittal midfemoral plane through the most lateral aspect of the medial femoral condyle. The sagittal plane that is located halfway between these two planes can be defined as the "midcondylar sagittal plane". The intersection between the midcondylar sagittal plane and the external cartilage surface yields the "anatomic midcondylar cartilage line". The location of the pathway of loading can be assessed relative to the anatomic midcondylar cartilage line of the medial femoral condyle. The identical procedure can be repeated for the lateral femoral condyle.

The following method can be used for the medial tibial plateau: A plane parallel to the sagittal tibial plateau plane can be defined through the most medial point of the medial tibial plateau. A parallel plane located halfway between this plane and the sagittal tibial plateau plane can yield the "midsagittal plane of the medial tibial plateau." The intersection of the midsagittal plane of the medial tibial plateau and the external cartilage surface can yield the "anatomic midtibial plateau cartilage line" of the medial tibial plateau. The identical procedure can be repeated for the lateral tibial plateau.

Figure 20:
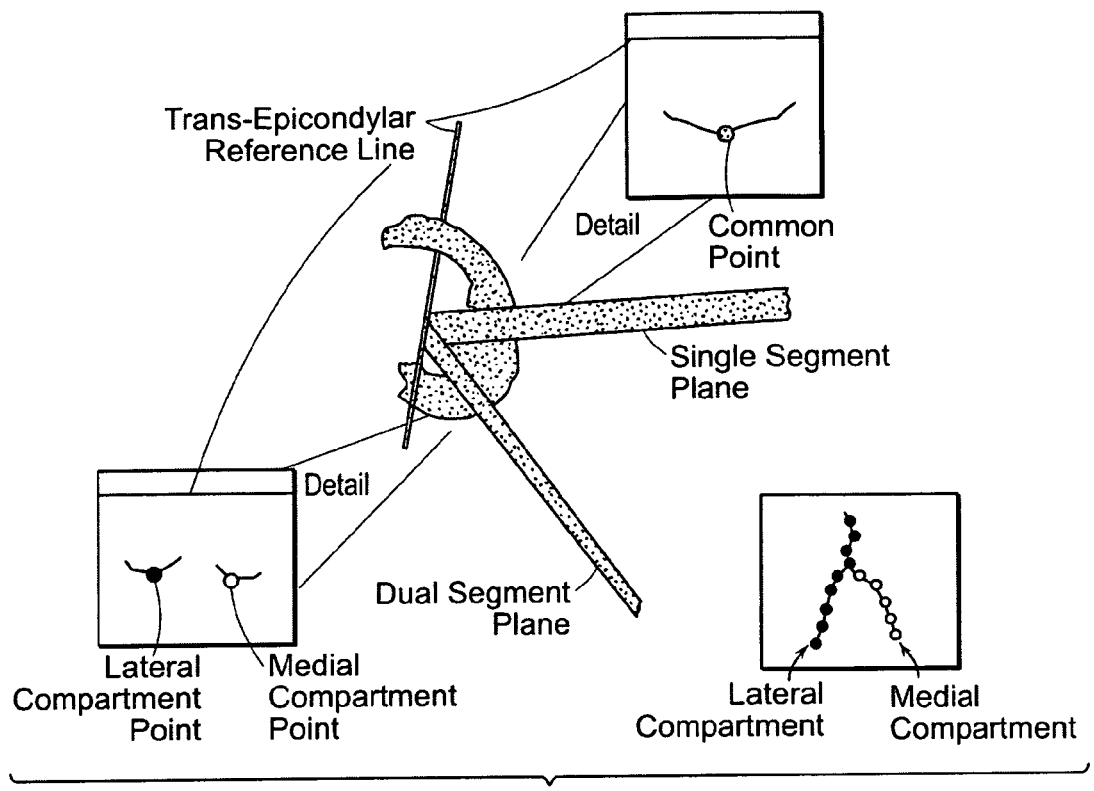
FIG. 20 shows the determination of the natural line of curvature as the cutting plain is rotated about the transepicondyear reference, the cartilage-plain intersection results in a curve.

In the second approach, one can calculate a "natural" line of curvature for each femoral cartilage component (FIG. 20). Intuitively, if one could roll the femoral condyles along a hard, flat surface, the line of contact with the flat surface would be the natural line of curvature. One can compare the actual tibiofemoral contact line to this reference line. Since one cannot physically remove the femur and roll it around, one can apply some geometric calculations to estimate this reference line. One can begin with the trans-epicondylar reference line previously described. One can then generate a plane coincident with this line oriented in an arbitrary initial position. The intersection of this plane and the external surface of the cartilage will produce a curve. One can then take the point furthest from the trans-epicondylar reference line as the natural contact point for this plane location. The next step is to rotate the plane by some increment, for example by one degree, and repeat the procedure. The operator can identify the rotation angles where the plane is intersecting the distinct medial—lateral compartments of the cartilage, and two points can be chosen, one from the medial femoral condyle and one from the lateral femoral condyle. If cartilage defects are present, in which case a compartment will not intersect in a curve but in a set of points, one can fit a spline through the points, then take the peak point of the spline as the contact point.

This can be repeated for the entire extent of the cartilage, resulting in a set of points that branch at the intercondylar notch. One can treat these points as two lines, and fit them with two splines. These can be the "natural" lines of curvature for each compartment.

Load Bearing Line Determination

The calculations in this section can begin with the relative motion of the subject specific femoral anatomy with respect to the subject specific tibial anatomy, and end with a line describing the point of closest approach between the femur and tibia during some activity of daily living. A number of approaches to this problem have been described in the literature; Crosset, Dennis, Stiehl, and Johnson have all described techniques which might be applicable. One can implement a proximity detection and approach algorithm (PDAA) as it was specifically designed to work with the Point Cluster Technique (albeit with prosthetic knee joint components).

Figure 21:
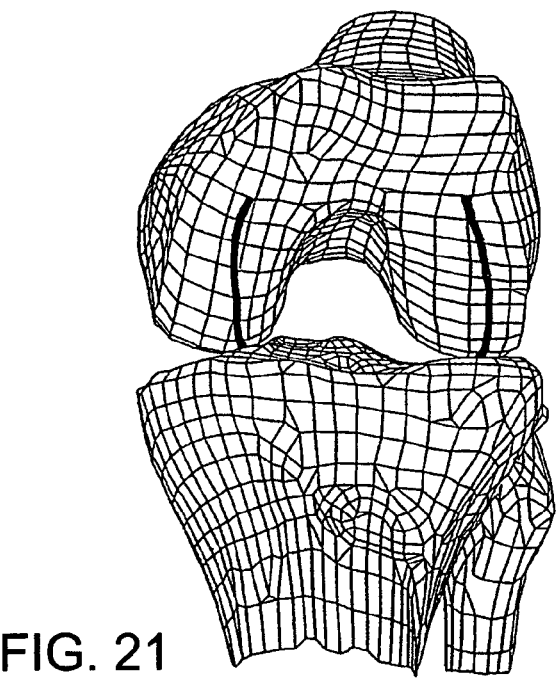
FIG. 21 shows the determination of the tibiofemoral contact line through the proximity detection and approach algorithm.

Physically, the tibial and femoral cartilage components deform under load, leading in general to a contact patch between opposing surfaces. As the geometric models are rigid, they will not deform under this load, but will instead intersect in a non-realizable manner. The PDAA has been designed to incrementally displace and rotate one of the surfaces until a realizable contact is achieved. It is understood that this is not a true point contact line, but rather a reproducible representation of contact location (FIG. 21).

The MR generated subject specific geometries can be used to detect rigid body contact proximity when the subject is in full extension. The femoral component can then be incrementally displaced until simultaneous medial and lateral condyle contact occur. This is a first order approximation to the location of the contact point; slip velocity calculations can then be used to determine the final estimate of the contact point. The next time step in the activity can now be examined, using the previous time step solution as a starting point for the calculation. The full extension time step can be chosen to match with the static reference posture; should it be necessary, one can add in other reference postures.

Once the contact points have been determined for all time steps of the activity, one can map the locations of these points onto the femoral cartilage. A coordinate system can be defined on the surface of the femoral cartilage, choosing as a reference line the point of contact the femoral component would have had were it rolled along a flat plane. This allows one to determine a contact line relative to the subject specific anatomy.

Assessing Cartilage Loss/Gain by Subtracting Images Acquired at Two Different Times Cartilage loss can be assessed by subtracting two images of the same individual that were acquired at different times $t_1$ and $t_2$. The same technique can be used to measure cartilage gain for example when a patient is undergoing chondro-regenerative treatment. Typically, the images are three-dimensional data sets (e.g. magnetic resonance images) and will have similar contrast (e.g. cartilage is shown in bright, bone is shown in dark). For each voxel, the difference of the intensities (gray values) at times $t_1$ and $t_2$ is computed. The difference image is then composed of the absolute values of the differences for each voxel.

The difference image cancels out structures that are the same in both images and enhances differences between the two images. This way, changes in the cartilage (loss or gain) are emphasized. In a subsequent step, the enhanced voxels can be extracted (e.g. using a thresholding or seed growing technique) and counted. The number of extracted voxels, multiplied by the volume of each voxel, yields the volume of the cartilage loss or cartilage gain.

The following variations of the technique are possible, where two or more variations can be combined:

The computation of the difference can be limited to a certain volume of interest (VOI) rather than the entire image, for example to assess the cartilage loss or gain at the site of a particular cartilage defect.

Prior to the calculation of the difference, a potential misalignment of the two images, that can for example be caused by differences in the positioning of the patient in the image acquisition unit, can be compensated. Possible ways to achieve this are, for example, surface-based or volume-based registration methods.

Variations in the intensities of two corresponding structures in the two images can be compensated prior to calculating the difference image. For example, if cartilage in the image taken at $t_1$ has a lower intensity than the cartilage in the image taken at $t_2$, the voxel gray values in the first image can be adjusted so that they match the ones of corresponding structures in the second image.

Instead of calculating the absolute value of the differences for all the voxels to create the difference image, only a certain range of the differences is considered. For example, only those voxel differences that are negative or only those that are positive are used in the composition of the difference image. This can help in differentiating between a gain and a loss of cartilage Provide Therapy A 2D or 3D surface registration technique can be used as an aid to providing therapy to match the anatomic orientation of the cartilage thickness map of a baseline and follow-up scan of a patient. The re-registered cartilage thickness map of the follow-up scan can then be subtracted from the baseline scan. This will yield the thickness difference, i.e. cartilage loss, as a function of x, y, and z. This can also be expressed as percentage difference.

The invention provides for techniques to assess biomechanical loading conditions of articular cartilage in vivo using magnetic resonance imaging and to use the assessment as an aid in providing therapy to a patient. In one embodiment, biomechanical loading conditions can be assessed in normal articular cartilage in various anatomic regions. In the knee joint, these anatomic regions include the posterior, central, and anterior medial femoral condyle, the posterior, central, and anterior medial tibial plateau, the posterior, central, and anterior lateral femoral condyle, the posterior, central, and anterior lateral tibial plateau, the medial and lateral aspect of the trochlea, and the medial and lateral facet and the median ridge of the patella. Since biomechanical loading conditions are assessed in vivo based on the anatomic features of each individual patient, a risk profile can be established for each individual based on the biomechanical stresses applied to cartilage. In this fashion, patients who are at risk for developing early cartilage loss and osteoarthritis can be identified. For example, patients with a valgus or varus deformity of the knee joint will demonstrate higher biomechanical stresses applied to the articular cartilage in the medial femorotibial or lateral femorotibial or patellofemoral compartments than patients with normal joint anatomy. Similarly, patients with disturbances of joint congruity will demonstrate higher biomechanical stress applied to certain regions of the articular cartilage. Such disturbances of joint congruity are often difficult to detect using standard clinical and imaging assessment. The amount of stress applied to the articular cartilage can be used to determine the patient's individual prognosis for developing cartilage loss and osteoarthritis. In another embodiment, biomechanical loading conditions can be assessed in normal and diseased articular cartilage. An intervention that can alter load bearing can then be simulated. Such interventions include but are not limited to braces, orthotic devices, methods and devices to alter neuromuscular function or activation, arthroscopic and surgical procedures. The change in load bearing induced by the intervention can be assessed prior to actually performing the intervention in a patient. In this fashion, the most efficacious treatment modality can be determined. For example, a tibial osteotomy can be simulated in the manner and the optimal degree of angular correction with regard to biomechanical loading conditions of normal and diseased cartilage can be determined before the patient will actually undergo surgery.

Estimation of biomechanical forces applied to normal cartilage can be used to determine a patient's risk for developing cartilage loss and osteoarthritis. Estimation of forces applied in and around a cartilage defect can be used to determine the prognosis of a cartilage defect and to guide the choice of therapy, e.g. treatment with chondroprotective or chondroregenerative agents, osteochondral allografting, cartilage transplantation, femoral or tibial osteotomy, or joint replacement surgery.

Having now provided a full discussion of various aspects of the technology relating to this invention, several further aspects of the invention can be seen.

One aspect of the invention is a method of assessing the condition of a joint in a mammal. The method comprises:
 (a) comparing the movement pattern of the joint with the cartilage degeneration pattern of the joint; and
 (b) determining the relationship between the movement pattern and the cartilage degeneration pattern Another aspect of the invention is a method for monitoring the treatment of a degenerative joint condition in a mammal. The method comprises
 (a) comparing the movement pattern of the joint with the cartilage degeneration pattern of the joint;
 (b) determining the relationship between the movement pattern and the cartilage degeneration pattern;
 (c) treating the mammal to minimize further degeneration of the joint condition; and
 (d) monitoring the treatment to the mammal.

Still another aspect of the invention is a method of assessing the rate of degeneration of cartilage in the joint of a mammal, wherein the joint comprises cartilage and the bones on either side of the cartilage, which method comprises
 (a) obtaining a cartilage degeneration pattern of the joint that shows an area of greater than normal degeneration,
 (b) obtaining a movement pattern of the joint that shows where the opposing cartilage surface contact,
 (c) comparing the cartilage degeneration pattern with the movement pattern of the joint, and
 (d) determining if the movement pattern shows contact of one cartilage surface with a portion of the opposing cartilage surface showing greater than normal degeneration in the cartilage degeneration pattern.

Another aspect of the specification is a method for assessing the condition of the knee joint of a human patient, wherein the knee joint comprises cartilage and associated bones on either side of the joint. The method comprises
 (a) obtaining the patient's magnetic resonance imaging (MRI) data of the knee showing at least the cartilage on at least one side of the joint,
 (b) segmenting the MRI data from step (a),
 (c) generating a geometrical or biochemical representation of the cartilage of the joint from the segmented MRI data,
 (d) assessing the patient's gait to determine the cartilage surface contact pattern in the joint during the gait assessment, and
 (e) correlating the contact pattern obtained in step (d) with the geometrical representation obtained in step (c).

Still another aspect of this invention is a method for assessing the condition of the knee joint of a human patient, wherein the knee joint comprises cartilage and associated bones on either side of the joint. The method comprises
 (a) obtaining the patient's magnetic resonance imaging (MRI) data of the knee showing at least the bones on either side of the joint,
 (b) segmenting the MRI data from step (a),
 (c) generating a geometrical representation of the bone of the joint from the segmented MRI data,
 (d) assessing the patient's gait to determine the load pattern of the articular cartilage in the joint during the gait assessment,
 (e) correlating the load pattern obtained in step (d) with the geometrical representation obtained in step (c).

Another aspect of this invention is a method for deriving the motion of bones about a joint from markers placed on the skin, which method comprises
- (a) placing at least three external markers on the patient's limb segments surrounding the joint,
- (b) registering the location of each marker on the patient's limb while the patient is standing completing still and while moving the limb,
- (c) calculating the principal axis, principal moments and deformation of rigidity of the cluster of markers, and
- (d) calculating a correction to the artifact induced by the motion of the skin markers relative to the underlying bone.

Another aspect of the invention is a system for assessing the condition of cartilage in a joint of a human, which system comprises
- (a) a device for electronically transferring a cartilage degeneration pattern for the joint to receiving device located distant from the transferring device;
- (b) a device for receiving the cartilage degeneration pattern at the remote location;
- (c) a database accessible at the remote location for generating a movement pattern for the joint of the human wherein the database includes a collection of movement patterns for human joints, which patterns are organized and can be accessed by reference to characteristics such as type of joint, gender, age, height, weight, bone size, type of movement, and distance of movement;
- (d) a device for generating a movement pattern that most closely approximates a movement pattern for the human patient based on the characteristics of the human patient;
- (e) a device for correlating the movement pattern with the cartilage degeneration pattern; and
- (f) a device for transmitting the correlated movement pattern with the cartilage degeneration pattern back to the source of the cartilage degeneration pattern.

In each of these aspects of the invention it is to be understood that a cartilage degeneration pattern may be, e.g., a 2D or 3D thickness map of the cartilage or a biochemical map of the cartilage.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of creating a cast, a physical model, or a mold for use with all or a portion of a diseased or damaged joint of a patient, the method comprising:
    electronically evaluating a cartilage degeneration pattern derived from image data of the diseased or damaged joint of the patient to obtain at least one of volume, area, thickness, curvature, geometry, shape, biochemical contents, signal intensity and relaxation time of normal, diseased, or both normal and diseased tissue including at least a portion of an articular surface of said diseased or damaged joint;
    evaluating at least one movement pattern of said diseased or damaged joint; and
    designing at least one of a cast, a physical model, and a mold based on said at least one movement pattern and said cartilage degeneration pattern.

2. The method of claim 1, wherein said evaluating of said at least one movement pattern includes testing said diseased or damaged joint in one or more flexion angles.

3. The method of claim 1, wherein said evaluating of said at least one movement pattern includes testing said diseased or damaged joint in one or more extension angles.

4. The method of claim 1, wherein said evaluating of said at least one movement pattern includes testing said diseased or damaged joint in one or more abduction angles.

5. The method of claim 1, wherein said evaluating of said at least one movement pattern includes testing said diseased or damaged joint in one or more adduction angles.

6. The method of claim 1, wherein said evaluating of said at least one movement pattern includes testing said diseased or damaged joint in one or more rotation angles.

7. The method of claim 1, wherein said physical model is an implant.

8. The method of claim 1, wherein said image data includes image data selected from the group consisting of x-ray data, MRI data, CT data, ultrasound data, and any combination thereof.

9. The method of claim 1, wherein said evaluating the at least one movement pattern occurs prior to surgery on the diseased or damaged joint.

10. A method of creating a cast, a physical model, or a mold for use with all or a portion of a diseased or damaged joint of a patient, the method comprising:
    electronically evaluating a cartilage degeneration pattern derived from image data of the diseased or damaged joint of the patient to obtain information concerning normal, diseased, or both normal and diseased cartilage including at least a portion of an articular surface of said diseased or damaged joint; and
    designing at least one of a cast, a physical model, and a mold based on said information concerning normal, diseased, or both normal and diseased cartilage.

11. The method of claim 10, wherein said physical model is an implant.

12. The method of claim 10, wherein said image data includes image data selected from the group consisting of x-ray data, MRI data, CT data, ultrasound data, and any combination thereof.

13. The method of claim 10, wherein the method further comprises determining a mechanical axis related to said diseased or damaged joint, and designing said cast, physical model, and mold based on said mechanical axis.

* * * * *